United States Patent [19]
Takayama et al.

[11] Patent Number: 5,624,380
[45] Date of Patent: Apr. 29, 1997

[54] MULTI-DEGREE OF FREEDOM MANIPULATOR

[75] Inventors: Shuichi Takayama; Takeaki Nakamura; Tatsuya Yamaguchi; Akio Nakada; Yasuhiro Ueda; Hideyuki Adachi; Katsunori Sakiyama; Yasukazu Tatsumi; Koji Fujio; Masaaki Hayashi; Shinji Kaneko; Yasuo Hirata; Toshimasa Kawai, all of Tokyo, Japan

[73] Assignee: Olympus Optical Co., Ltd., Tokyo, Japan

[21] Appl. No.: 396,347

[22] Filed: Feb. 28, 1995

Related U.S. Application Data

[63] Continuation of Ser. No. 29,904, Mar. 11, 1993, abandoned.

[30]   Foreign Application Priority Data

| Mar. 12, 1992 | [JP] | Japan | 4-053643 |
| Mar. 13, 1992 | [JP] | Japan | 4-055735 |
| Mar. 13, 1992 | [JP] | Japan | 4-055739 |
| Mar. 16, 1992 | [JP] | Japan | 4-272370 |

[51] Int. Cl.$^6$ .................................................. A61B 1/008
[52] U.S. Cl. ............................ 600/146; 600/151; 600/141
[58] Field of Search .................. 128/4–10; 307/37–40; 604/281

[56]   References Cited

U.S. PATENT DOCUMENTS

| 4,298,260 | 11/1981 | Takayama | 354/62 |
| 4,884,557 | 12/1989 | Takehana et al. | 128/4 |
| 4,930,494 | 6/1990 | Takehana et al. | 128/4 |
| 5,060,632 | 10/1991 | Hibno et al. | 128/6 |
| 5,235,964 | 8/1993 | Abenaim | 128/4 |
| 5,289,043 | 2/1994 | Marshall et al. | 307/38 |

Primary Examiner—Richard J. Apley
Assistant Examiner—John P. Leubecker
Attorney, Agent, or Firm—Frishauf, Holtz, Goodman, Langer & Chick

[57]   ABSTRACT

A multi-degree-of-freedom manipulator includes a flexible tube having a plurality of flex portions provided therealong, a plurality of actuators made of shape memory alloy and respectively provided near the flex portions to correspond to the flex portions, for flexing the flex portions, two common energy transmission paths, extending along the flexible tube, for transmitting an energy to the actuators, and selective energy supply members, provided between the common energy transmission paths and the actuators in series, for controlling the energy supplied from the common energy transmission path to the actuators, thereby respectively independently driving the actuators to bend the flexible tube.

12 Claims, 44 Drawing Sheets

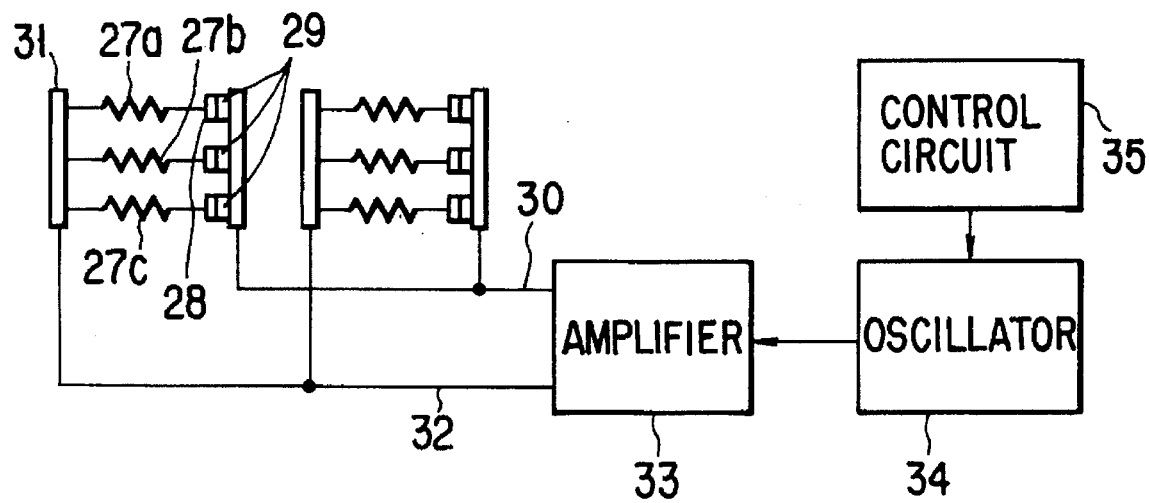
F I G. 7
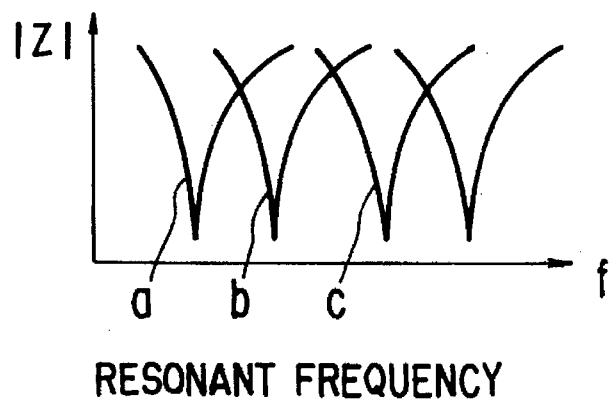
RESONANT FREQUENCY
F I G. 8

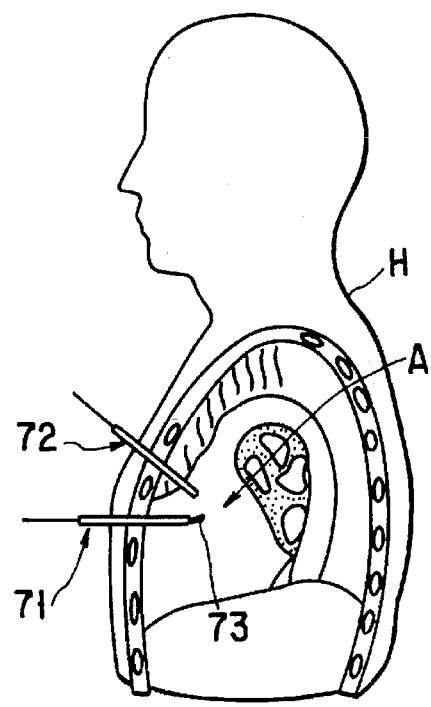
F I G. 13
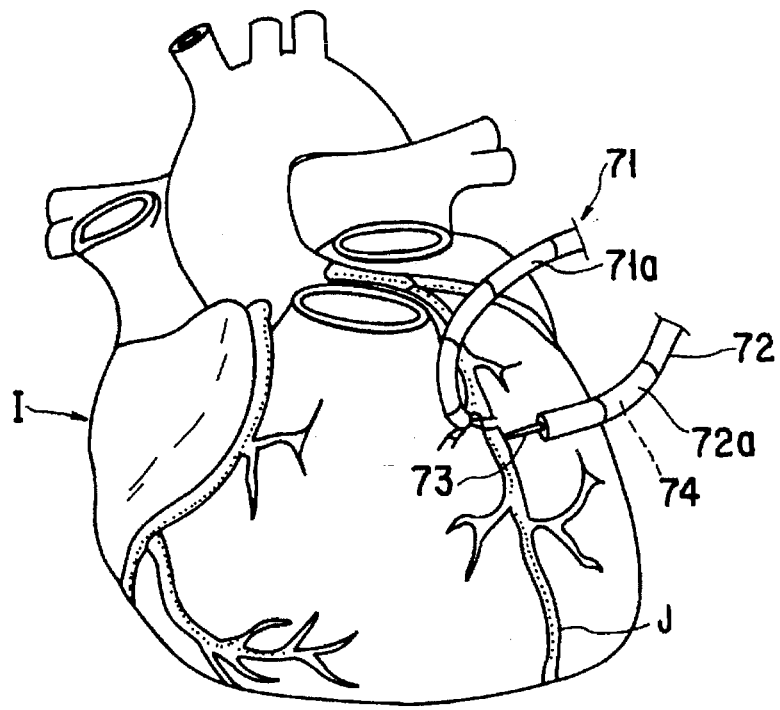
F I G. 14

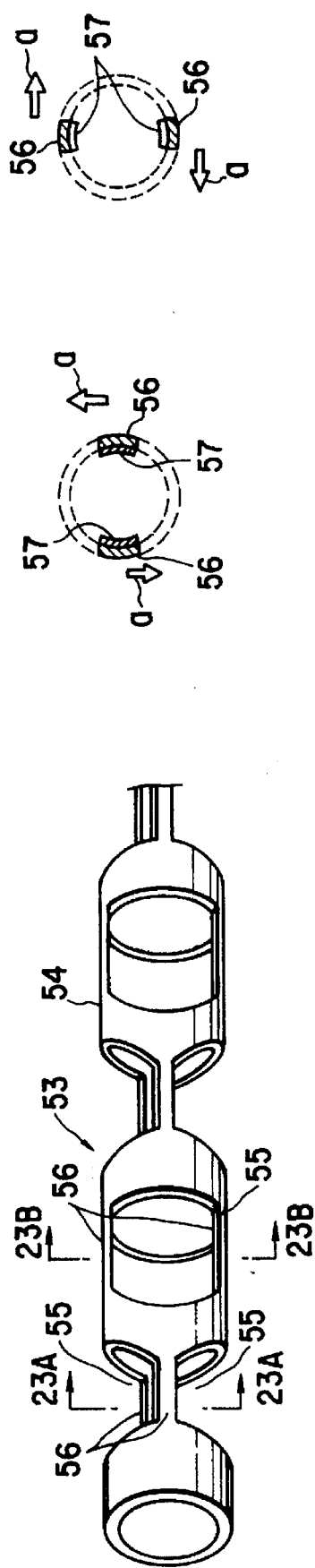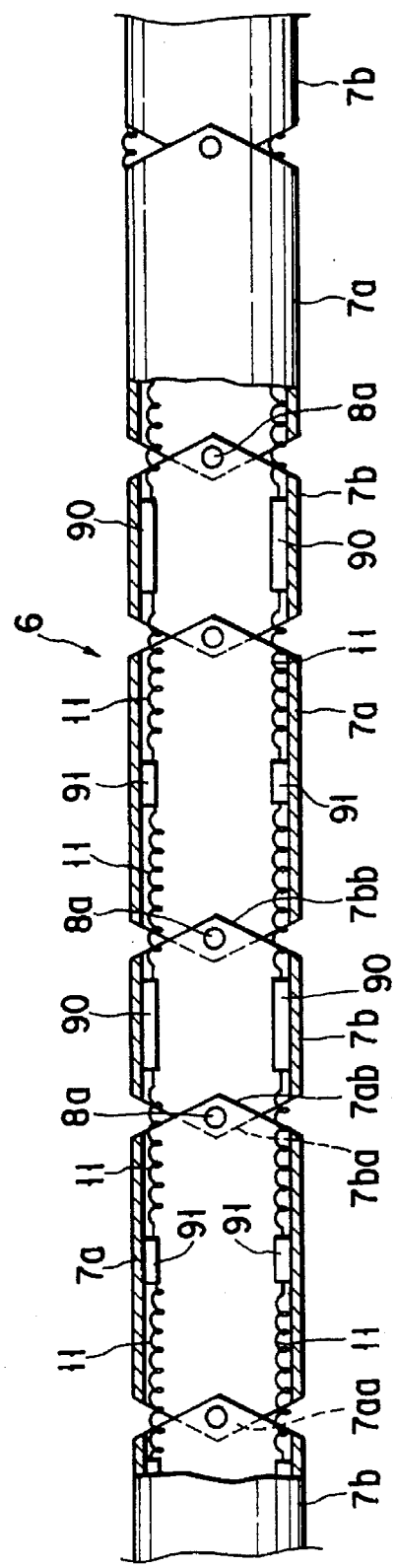

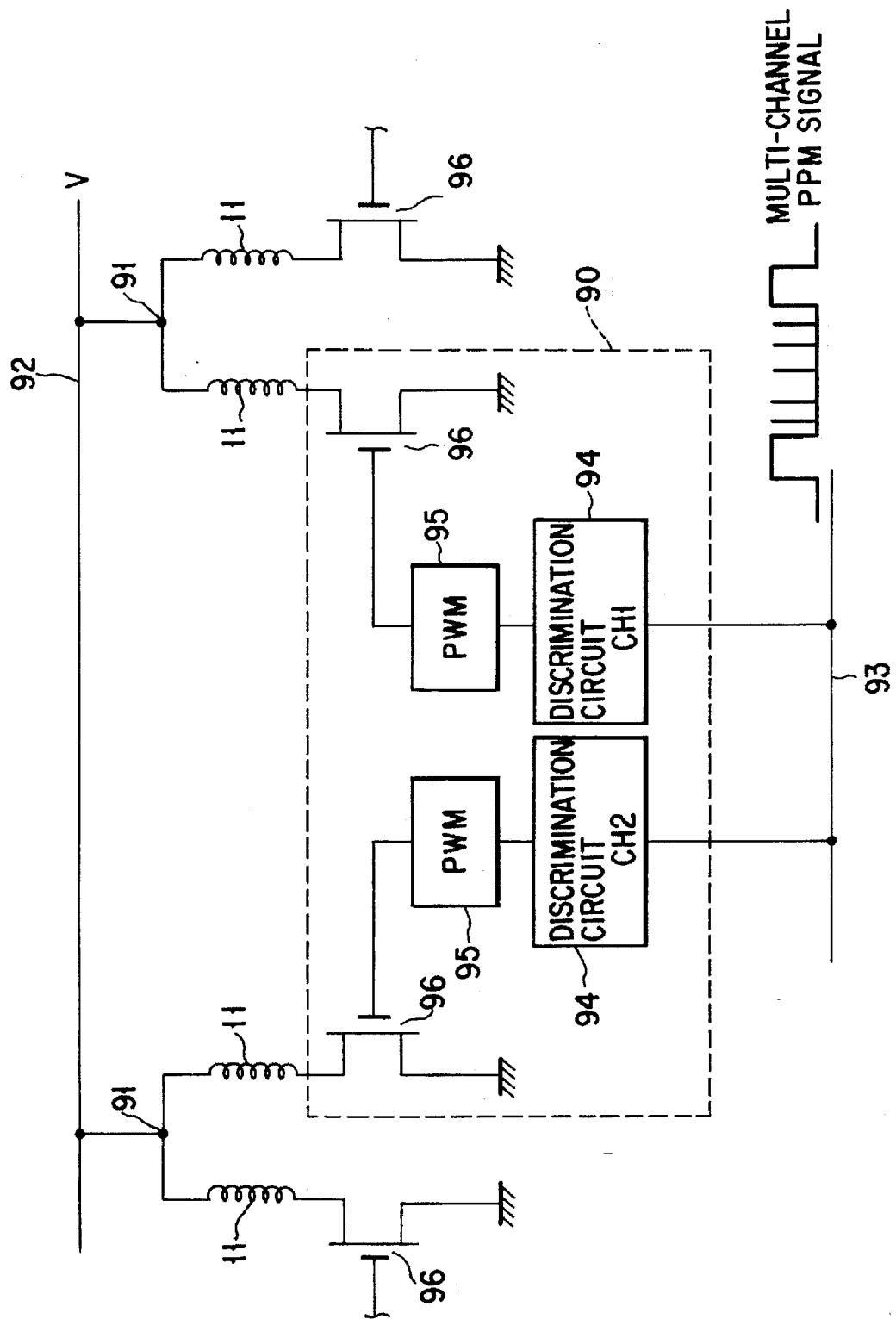
F I G. 25

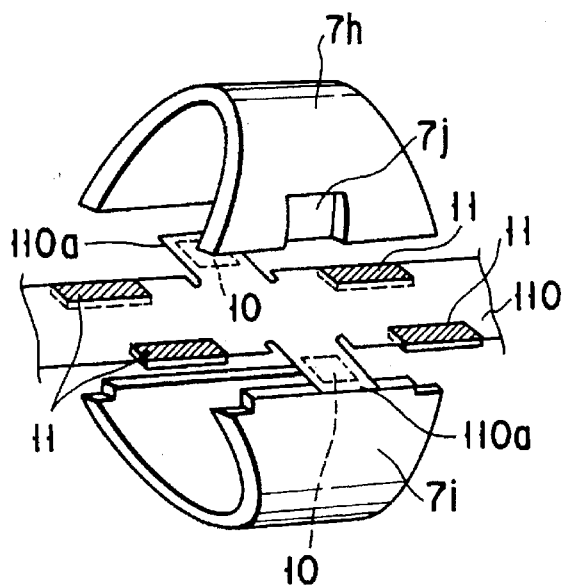
F I G. 31
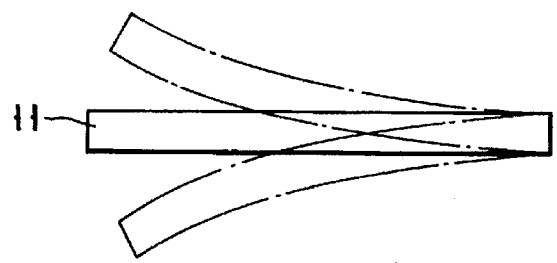
F I G. 32
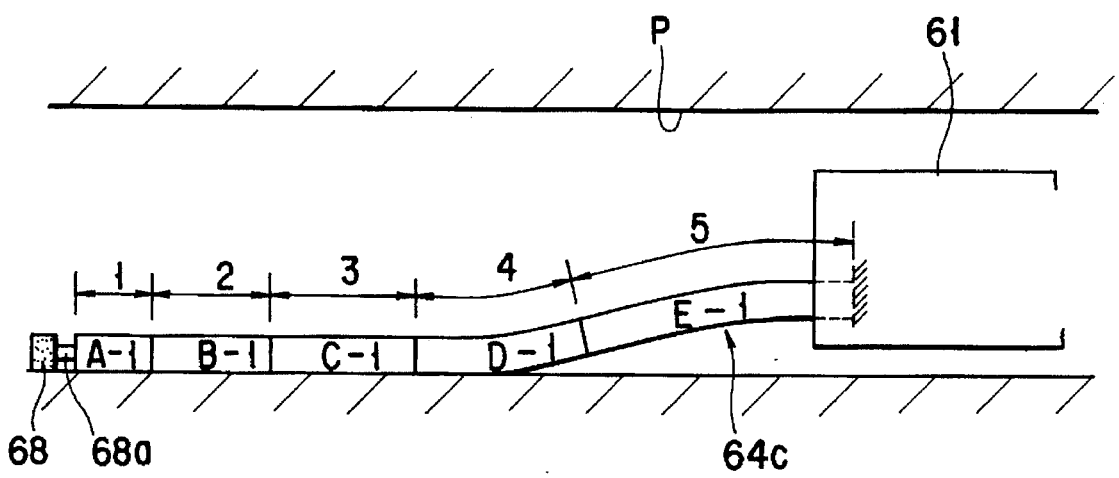
F I G. 33

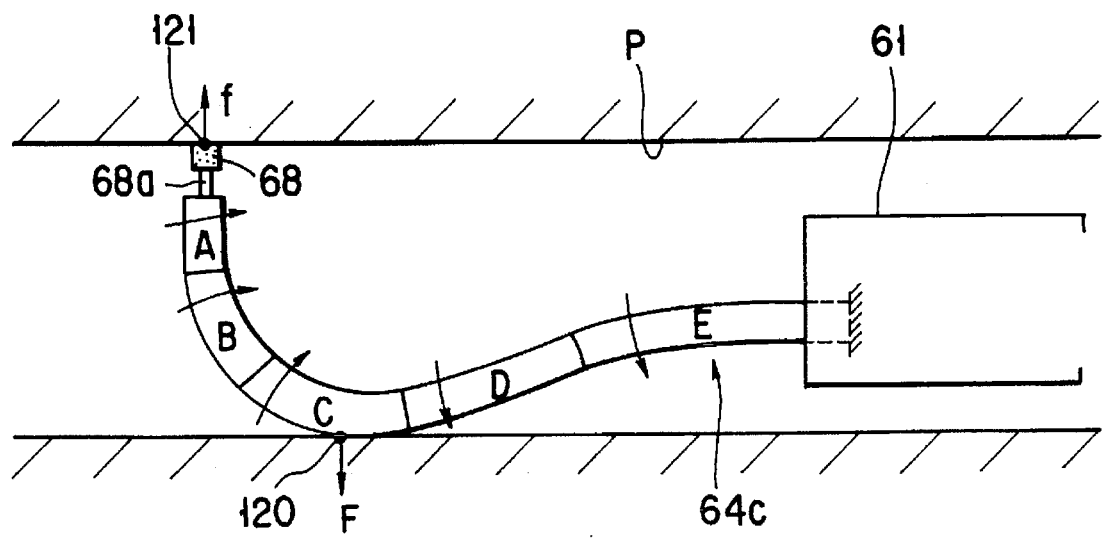
F I G. 34
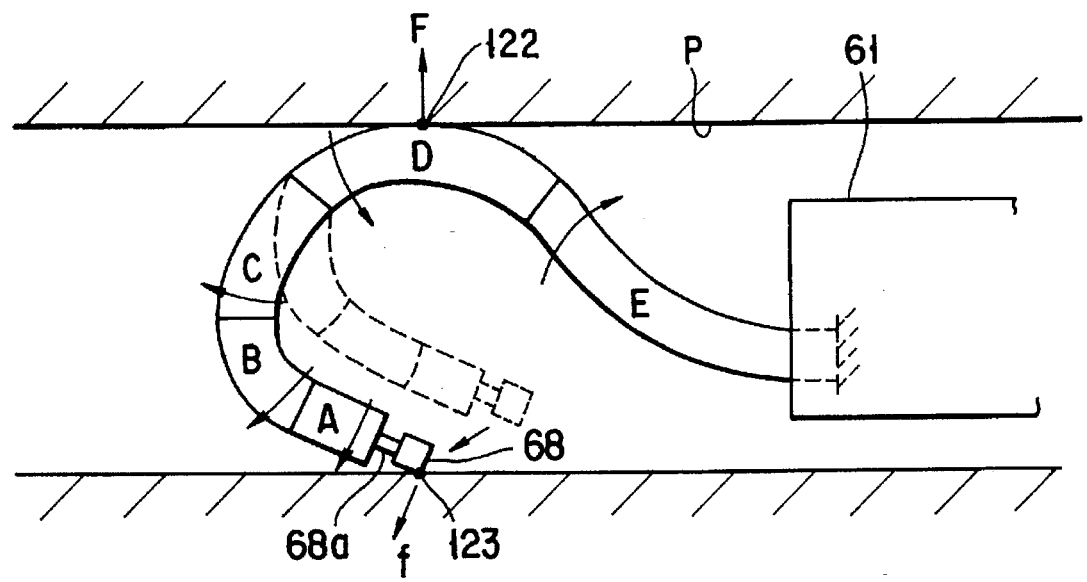
F I G. 35

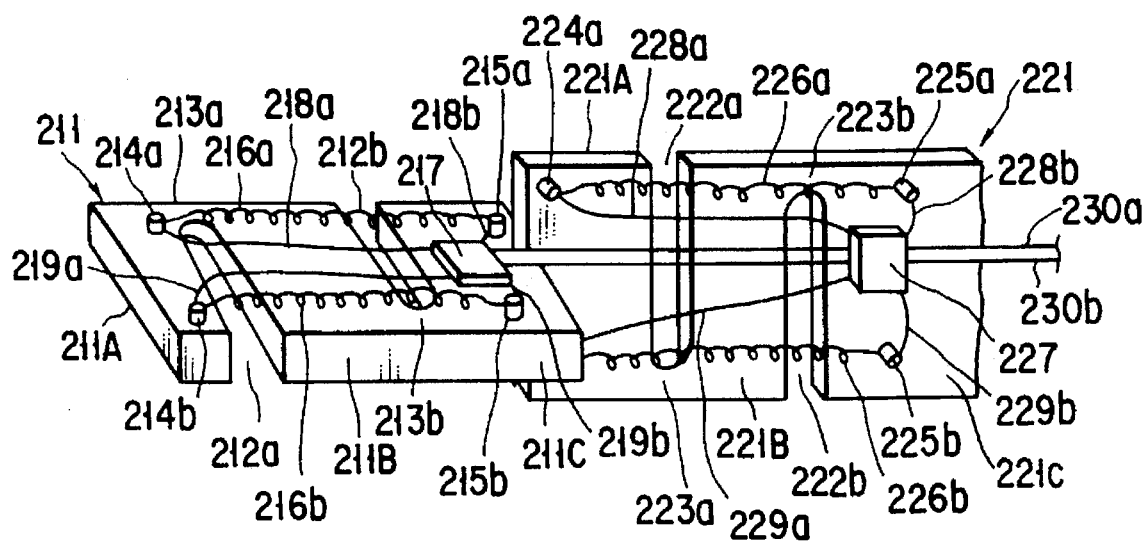
F I G. 36
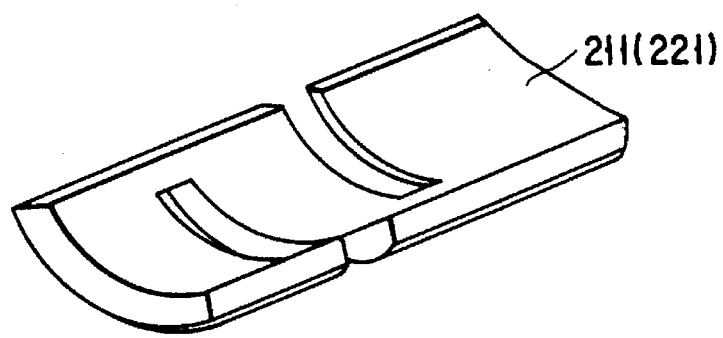
F I G. 37

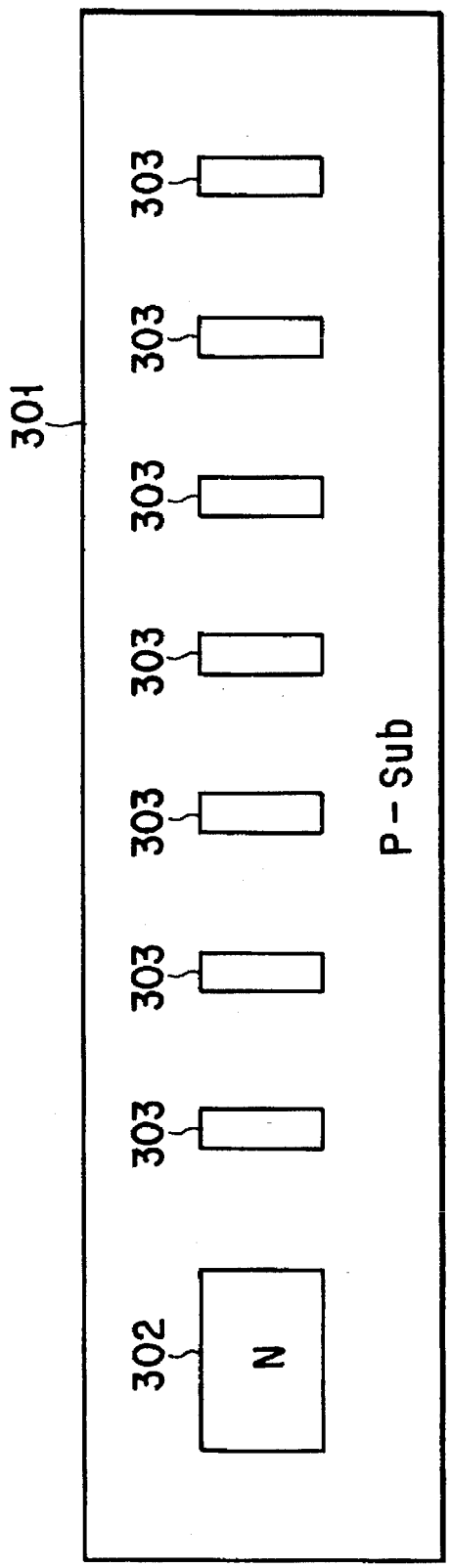
F I G. 38A
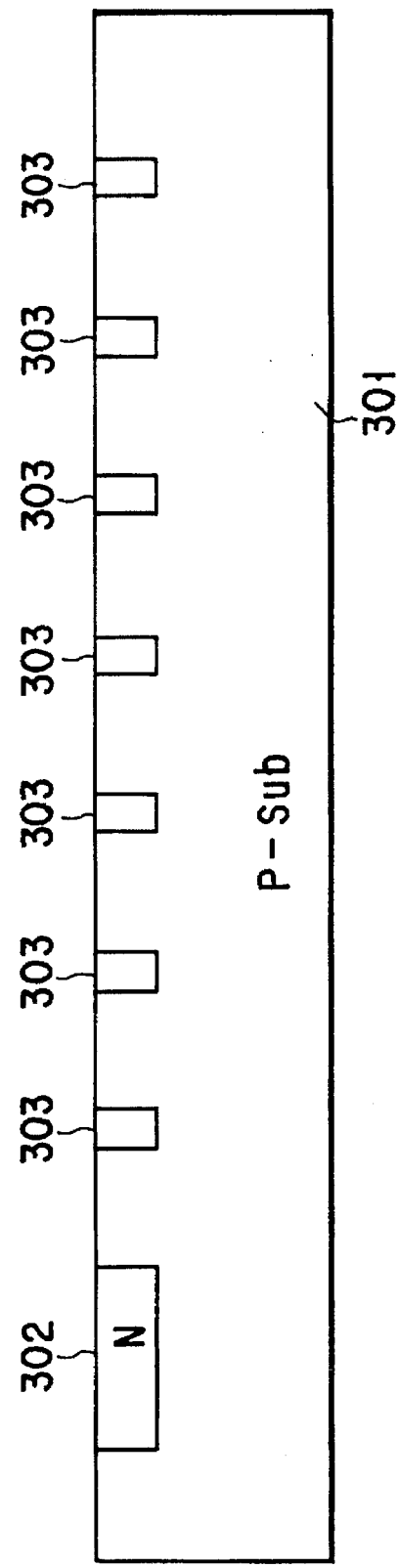
F I G. 38B

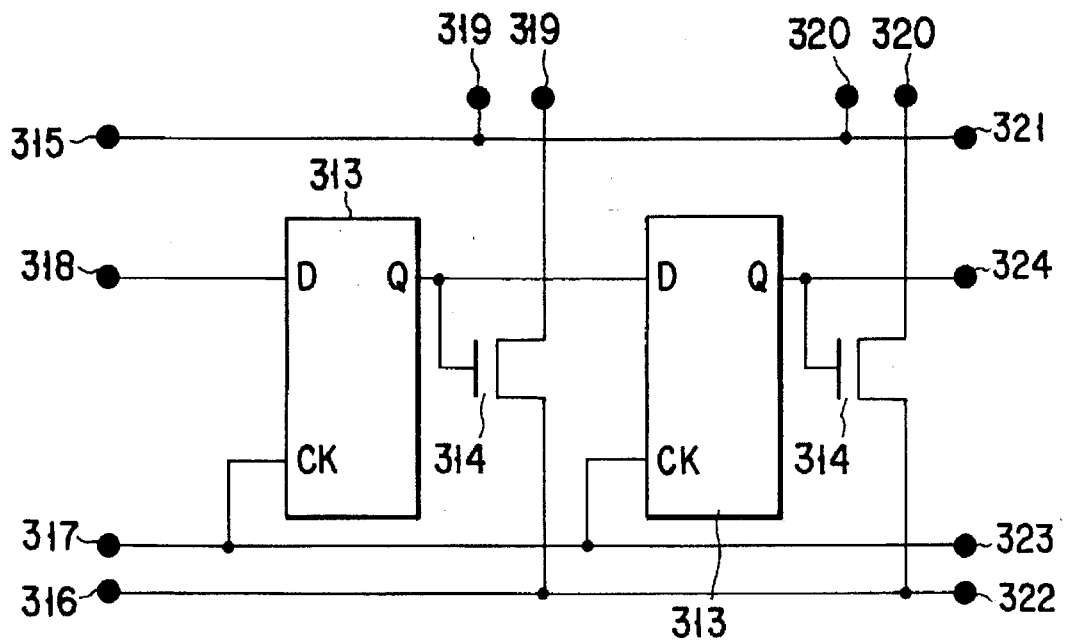
F I G. 41
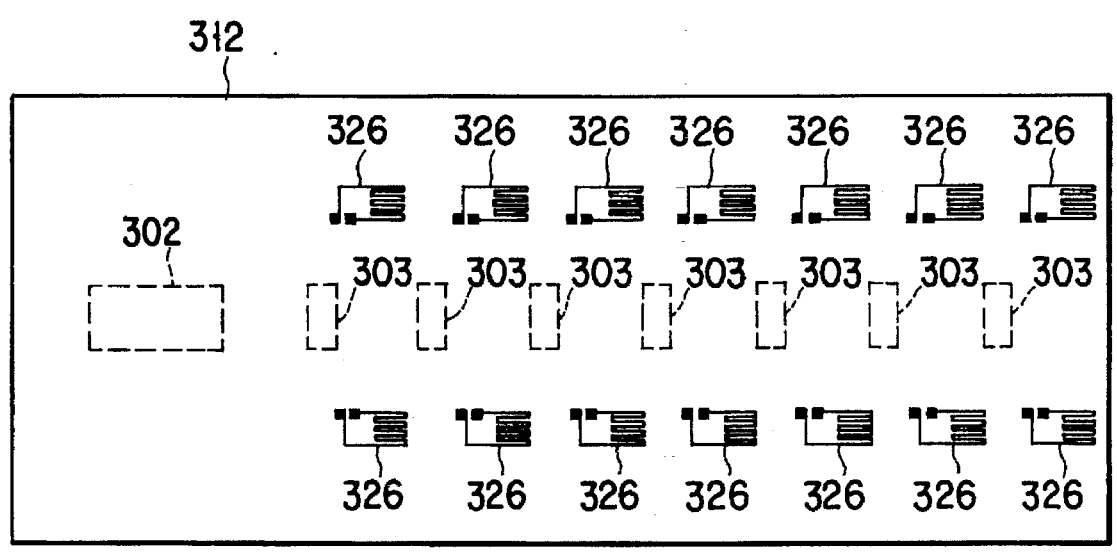
F I G. 42

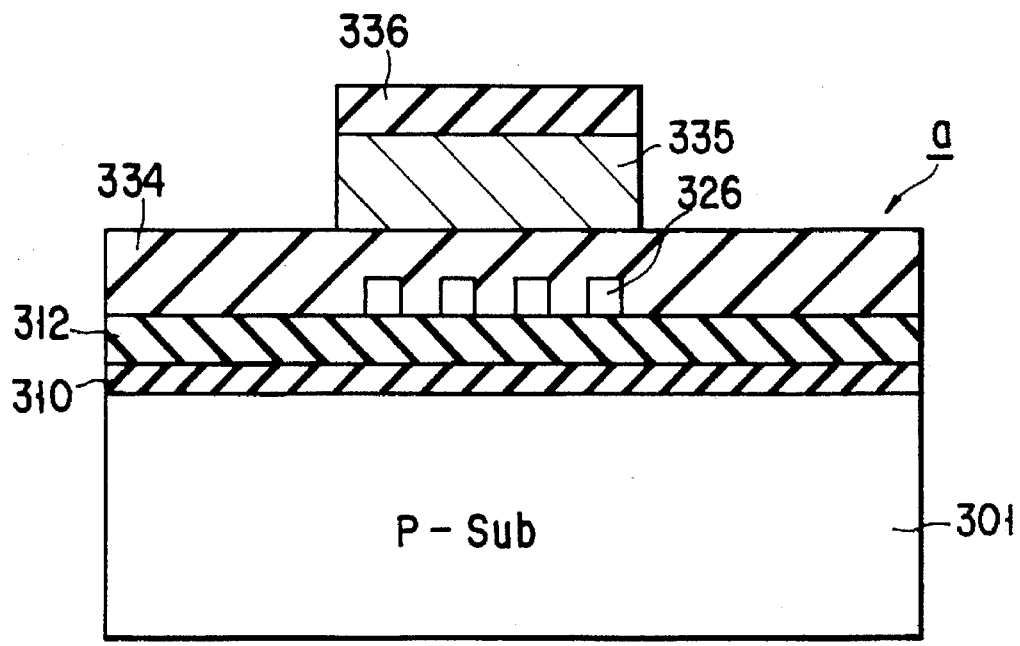
F I G. 46
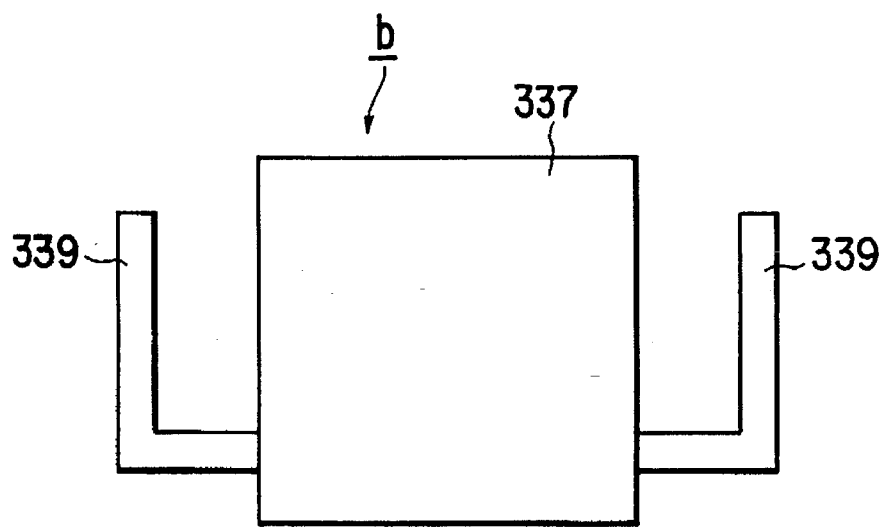
F I G. 48

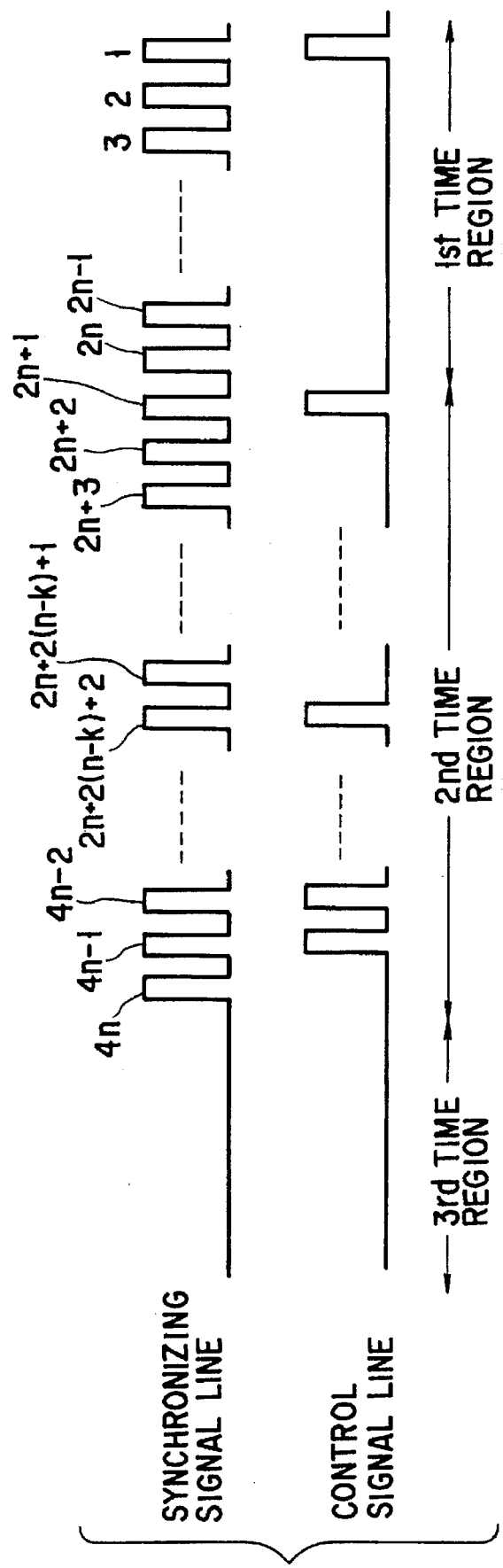
F I G. 51

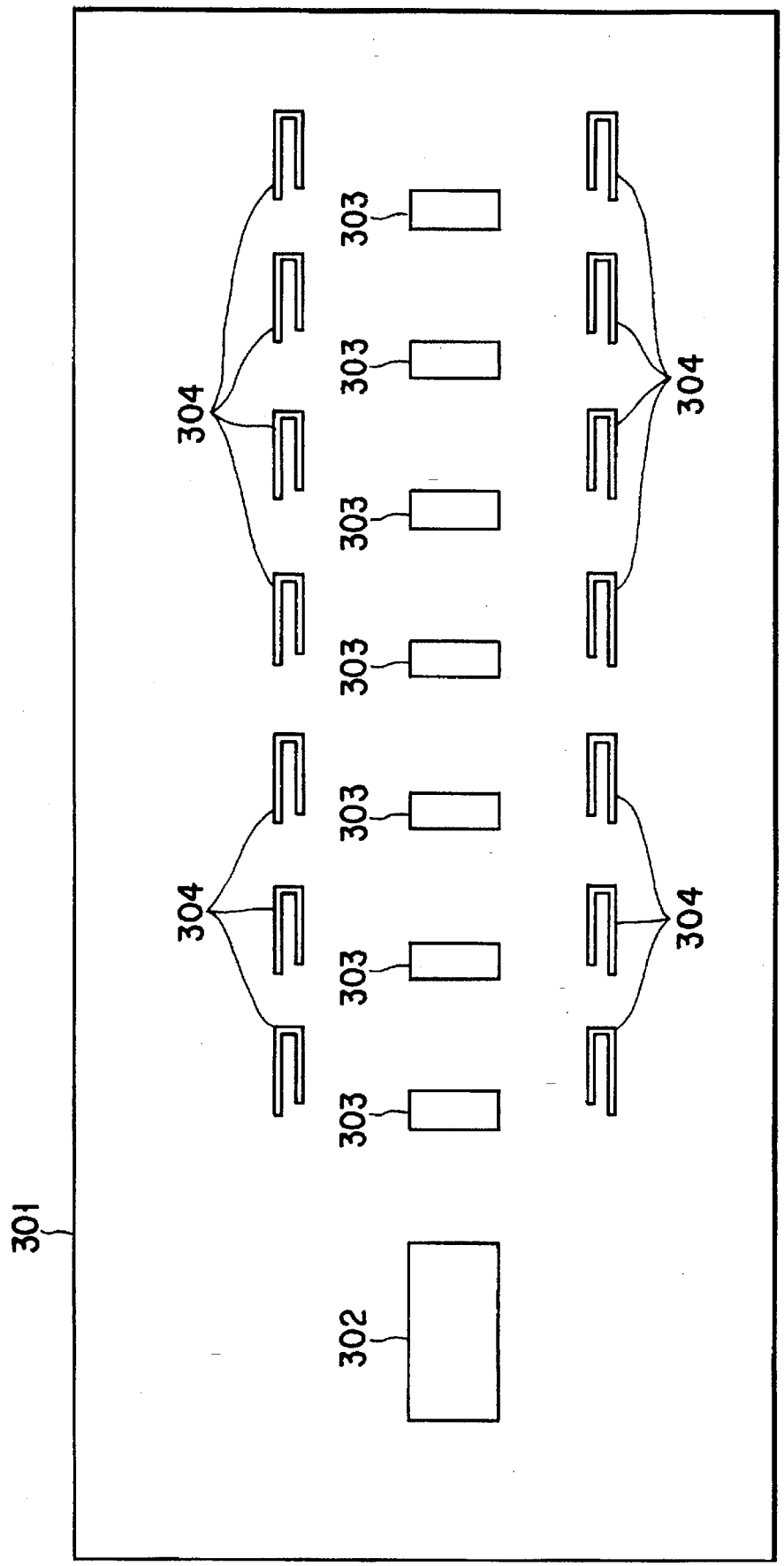
F I G. 52

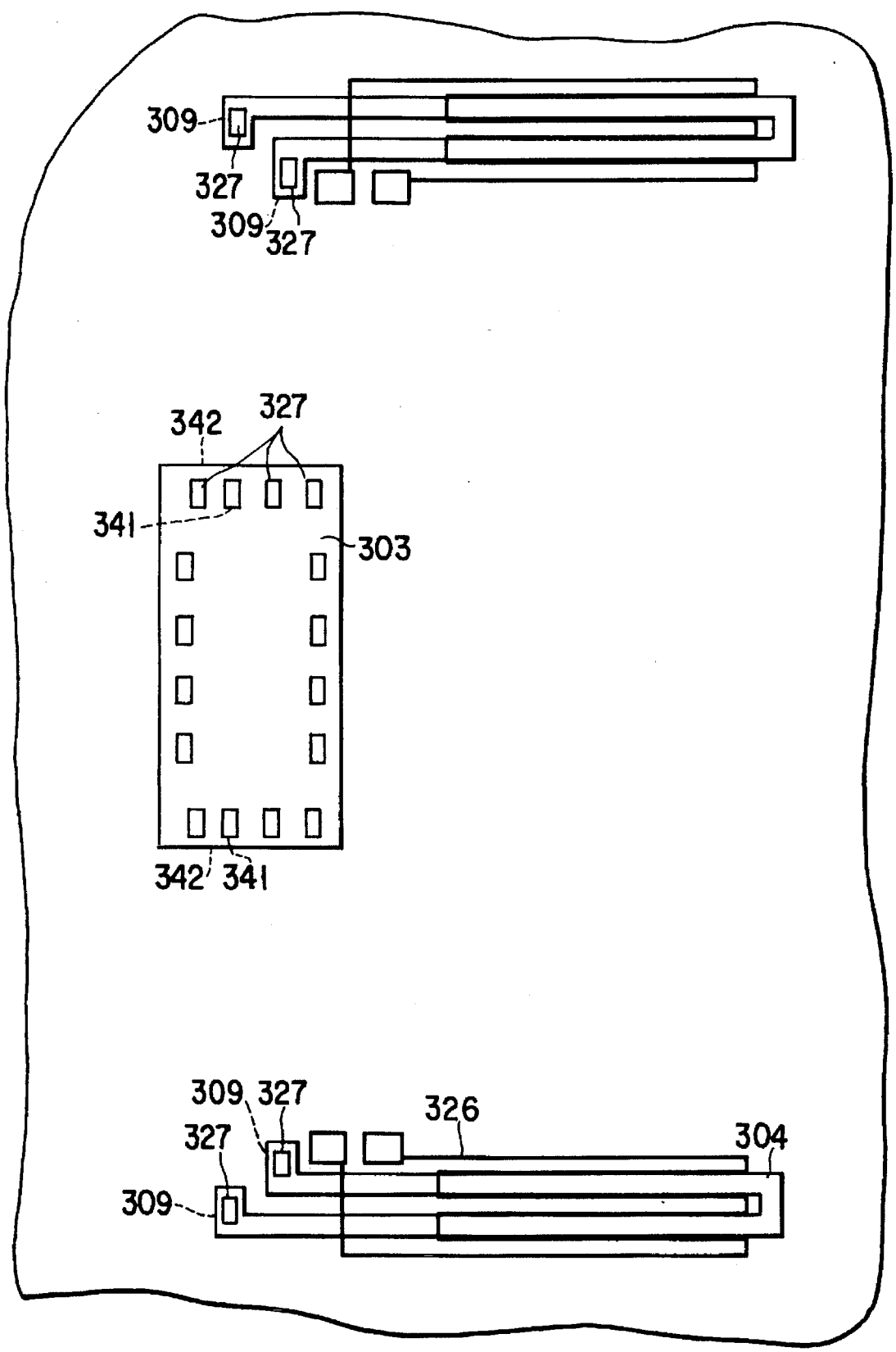
F I G. 54

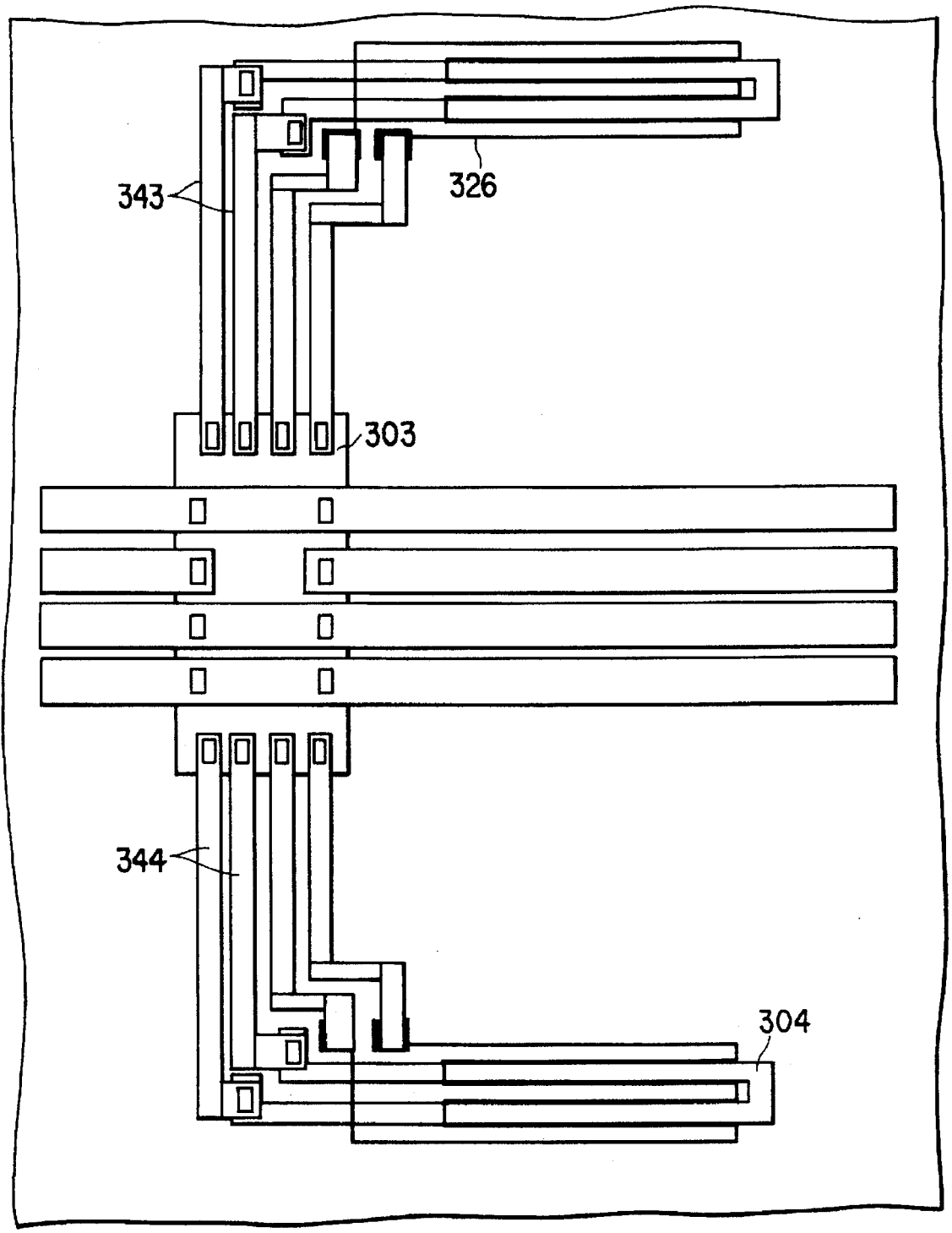
F I G. 55

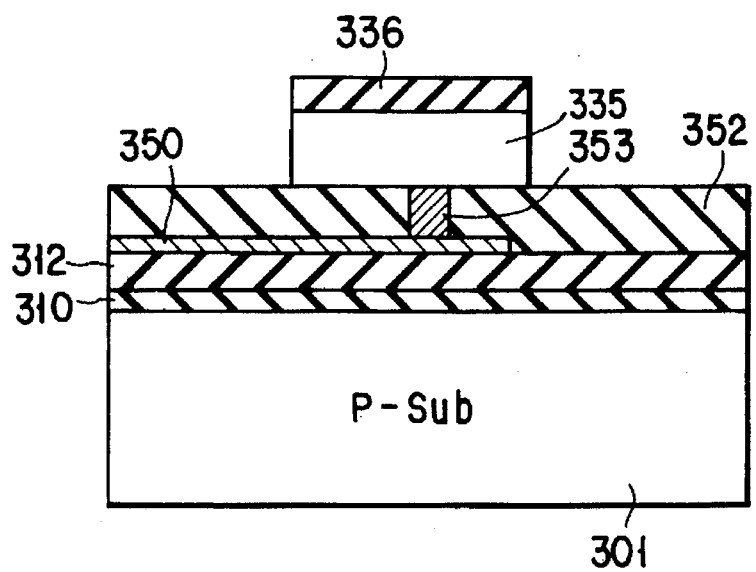
F I G. 59
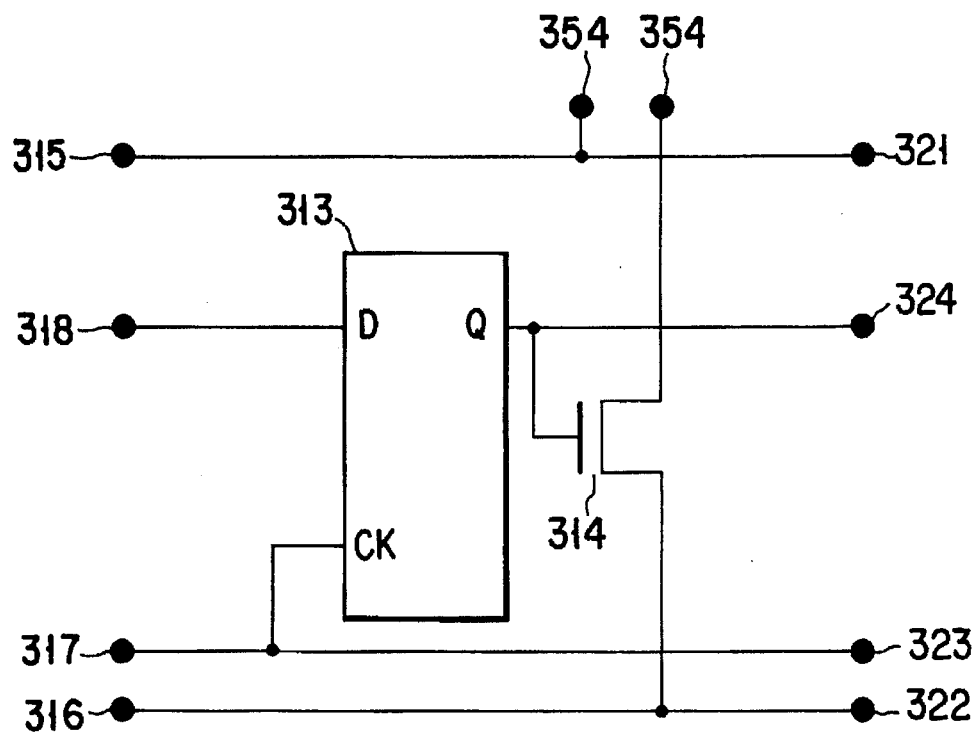
F I G. 60

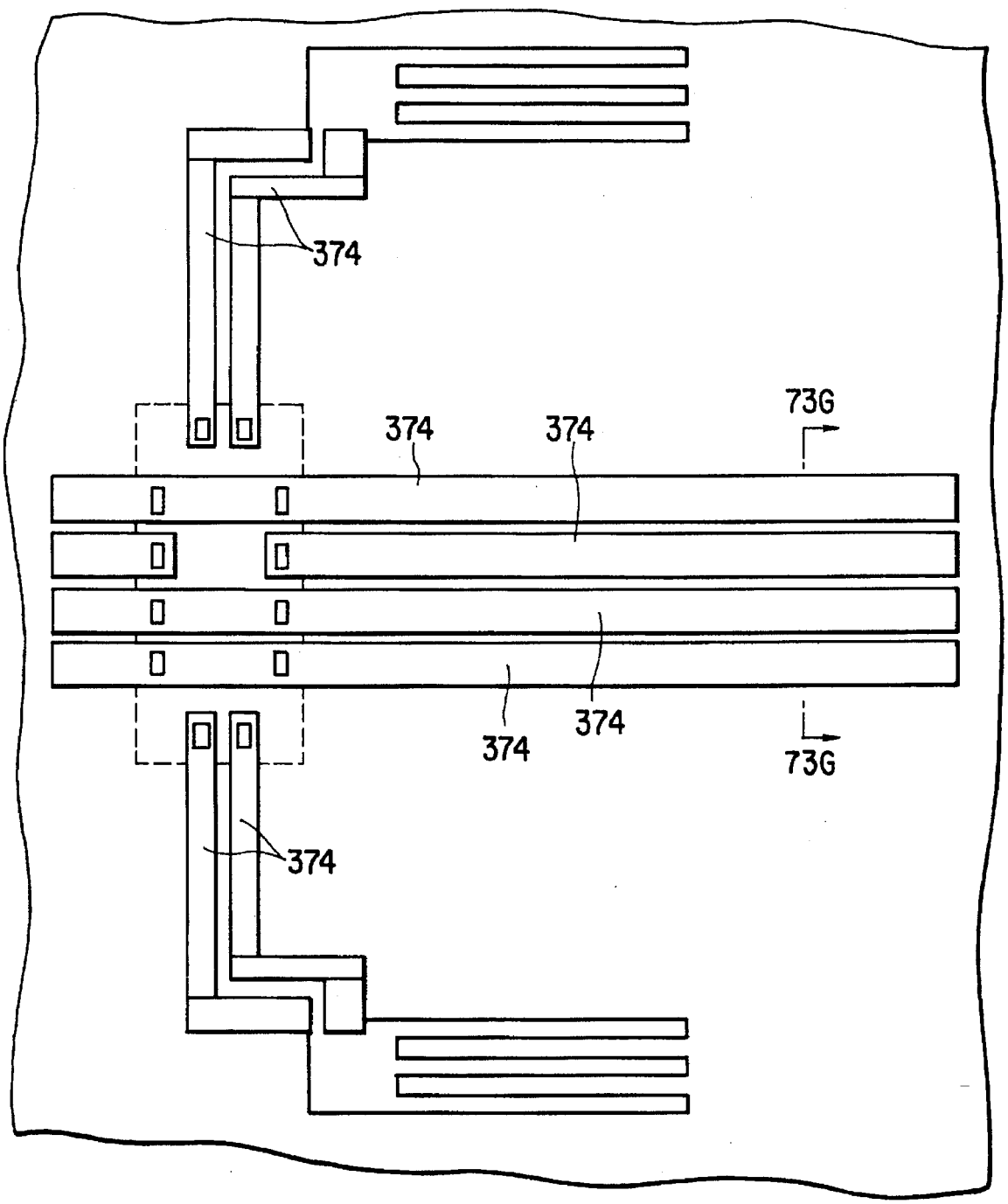
F I G. 72

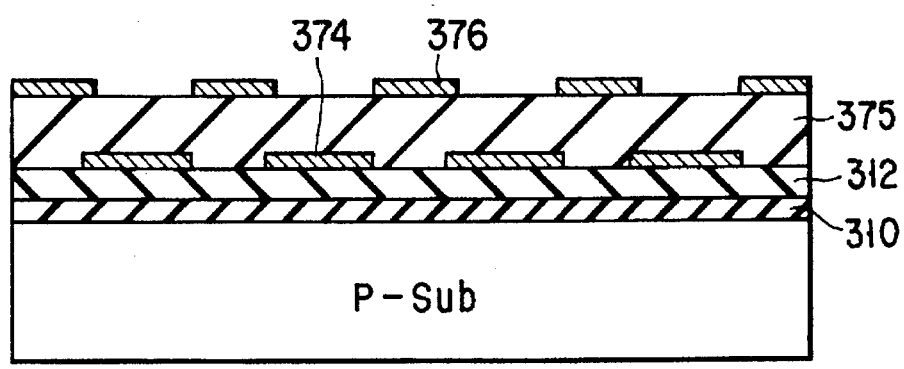
F I G. 73
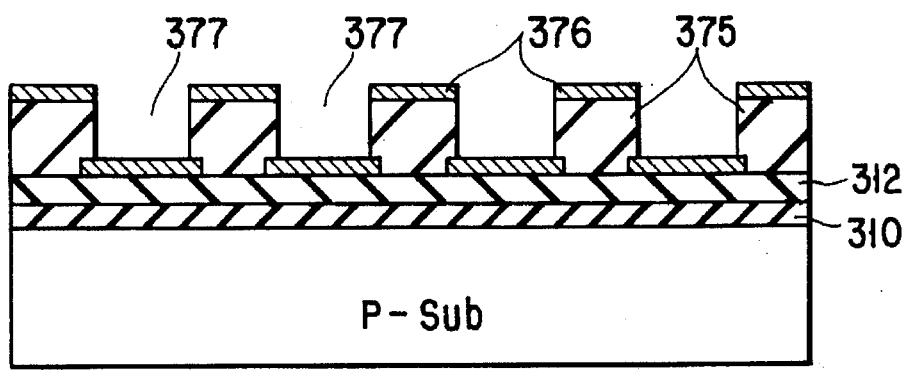
F I G. 74
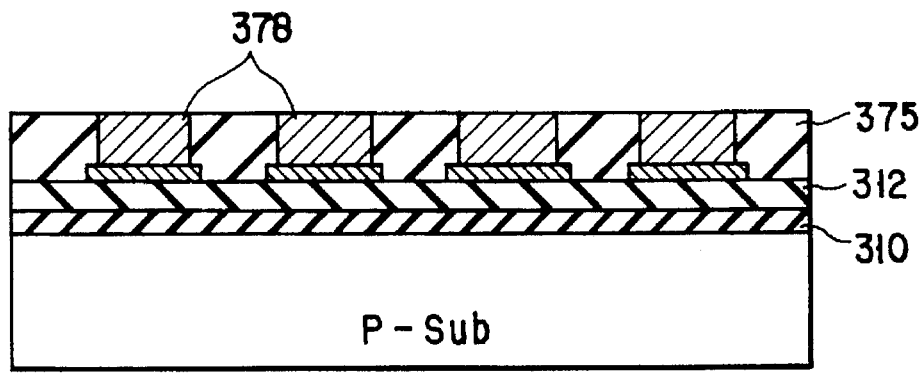
F I G. 75

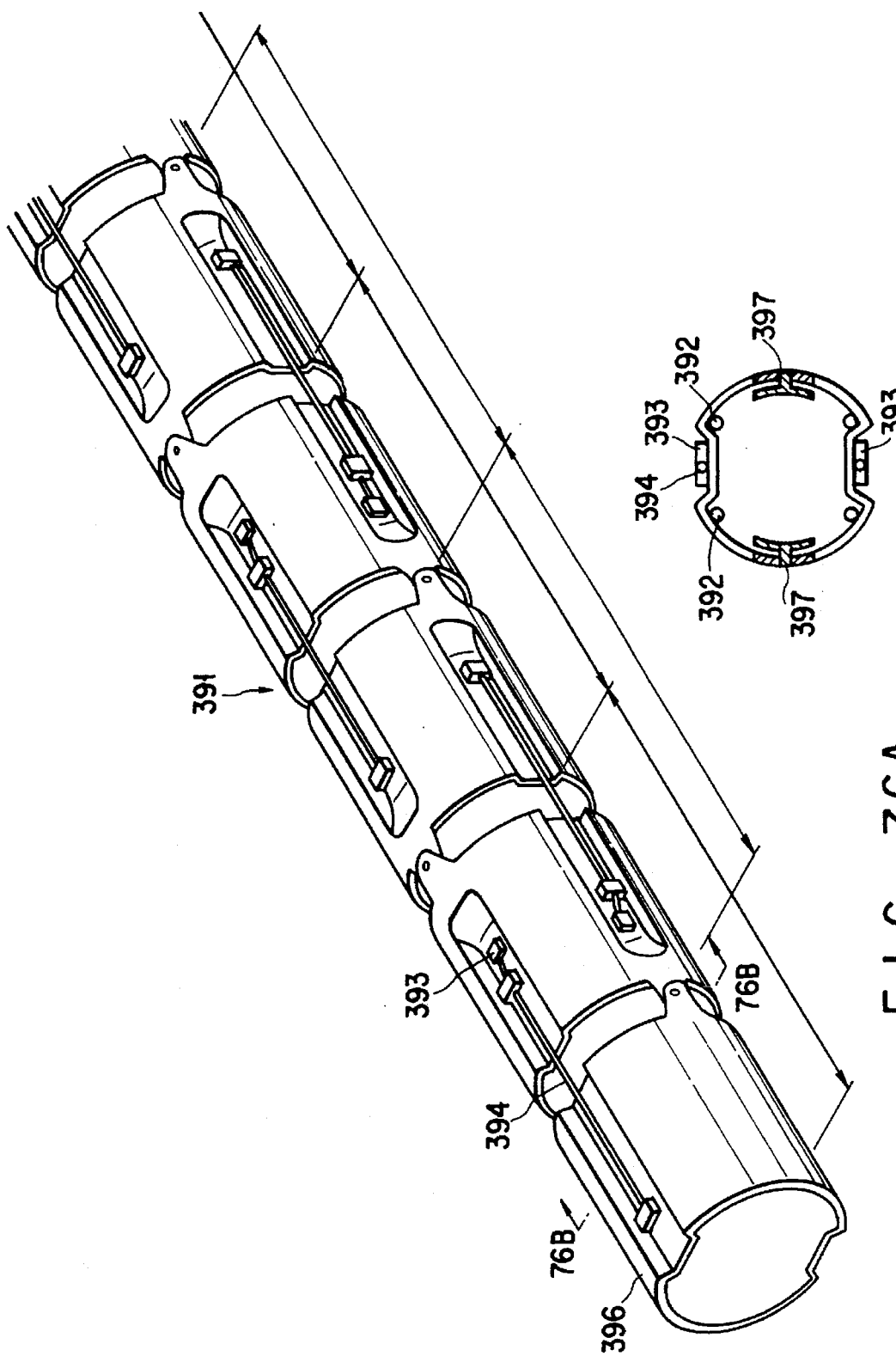

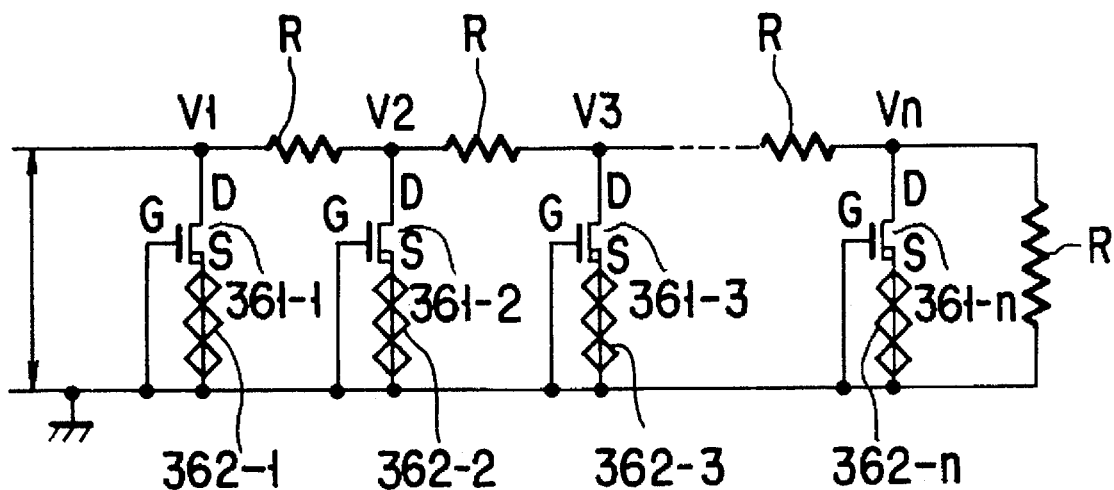
F I G. 78
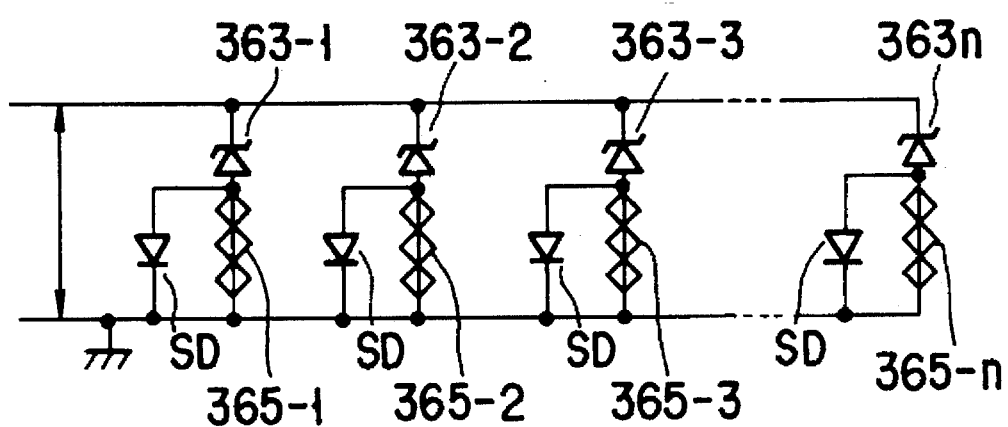
F I G. 79

MULTI-DEGREE OF FREEDOM MANIPULATOR

This application is a continuation of application Ser. No. 08/029,904, filed Mar. 11, 1993, abandoned.

BACKGROUND OF THE INVENTION

1. Field of the Invention

The present invention relates to a multi-degree-of-freedom manipulator, e.g., a catheter, an endoscope, and a laser probe, which is used by being inserted in a canal e.g., a living body cavity, and a method of manufacturing the same.

2. Description of the Related

For example, the flexible tube of a medical catheter or endoscope, or the flexible tube of an industrial endoscope that performs inspection and maintenance of an industrial pipe, e.g., a gas pipe, is constituted by a multi-degree-of-freedom manipulator in which a plurality of bending flex portions are arranged in a row.

A plurality of actuators are provided in the flexible tube to correspond to the plurality of bending flex portions. Each actuator is formed of a bending operation wire made of a linear shape memory alloy which changes in length in accordance with e.g., a change in temperature. When power is supplied from the operator side of the flexible tube to selectively heat the actuators, predetermined bending flex portions of the flexible tube can be flexed or bent, so that the distal end portion of the flexible tube can be guided to a target location.

In the conventional multi-degree-of-freedom flexible tube, the plurality of actuators are provided to correspond to the plurality of bending flex portions, as described above, and exclusive energy transmission paths are provided to the respective actuators to selectively drive them. More specifically, when the actuator is made of a shape memory alloy, each lead wire to be electrically connected to the actuator is provided in the flexible tube, and the actuator is powered and heated through the lead wire.

An endoscope to be inserted in a deep portion of a living body cavity or an industrial endoscope to be inserted in a long pipe has a long flexible tube. As the length of the flexible tube is increased, the number of bending flex portions is increased, and the number of actuators is also increased. Then, the number of energy transmission paths is also increased to make the structure complicated, and the outer diameter of the flexible tube is undesirably increased.

SUMMARY OF THE INVENTION

It is an object of the present invention to provide a multi-degree-of-freedom manipulator wherein a plurality of bending flex portions can be selectively flexed and the number of energy transmission paths is decreased to decrease the diameter of and simplify a flexible tube, and a method of manufacturing the same.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 7 is a schematic block diagram showing the energy transmission path of a multi-degree-of-freedom flexible tube according to the second embodiment of the present invention;

FIG. 8 is a graph of the LC resonance circuit of the second embodiment of the present invention;

FIG. 13 is a view for explaining a case wherein the multi-degree-of-freedom flexible tube of the present invention is applied to a surgical microrobot;

FIG. 14 is an enlarged view showing a portion A of FIG. 13;

FIG. 22 is a perspective view of the sheath body of a manipulator;

FIG. 23A is a cross-sectional view taken along the line 23A—23A of FIG. 22, and FIG. 23B is a cross-sectional view taken along the line 23B—23B of FIG. 22;

FIG. 24 is a schematic view showing the bendable flex portion of a multi-degree-of-freedom manipulator according to the fifth embodiment of the present invention;

FIG. 25 is a schematic block diagram of the controller of the bendable flex portion shown in FIG. 24;

FIGS. 26A and 26B show the sixth embodiment of the present invention, in which FIG. 26A is a longitudinal sectional view showing the main arrangement of a bendable flex device, and FIG. 26B is a sectional view taken along the line 26B—26B of FIG. 26A;

FIG. 31 is a partially exploded perspective view showing the assembled state of a bendable flex portion;

FIG. 32 is a schematic view for explaining the operation of an SMA (Shape Memory Alloy);

FIG. 33 is a schematic view showing a multi-degree-of-freedom manipulator;

FIG. 34 is a schematic view showing an operating state of the multi-degree-of-freedom manipulator of FIG. 33;

FIG. 35 is a schematic view showing another operating state of the multi-degree-of-freedom manipulator of FIG. 33;

FIG. 36 is a perspective view showing a multi-degree-of-freedom flexible tube according to the eighth embodiment of the present invention;

FIG. 37 is a perspective view showing a modification of the plate structure of the multi-degree-of-freedom flexible tube according to the eighth embodiment of the present invention;

FIGS. 38A and 38B to FIG. 50 are views for explaining a multi-degree-of-freedom flexible tube according to the ninth embodiment of the present invention, wherein FIGS. 38A and 38B are schematic plan and sectional views, respectively, showing a state wherein n-type lightly doped regions are formed on a p-type lightly doped semiconductor substrate, FIG. 39 is a view showing a state wherein wells are formed in the n-type lightly doped region, FIG. 40 is a view showing a state wherein a CMOS integrated circuit and insulating interlayers are formed in the n-type lightly doped diffusion region, FIG. 41 is a circuit diagram of the CMOS integrated circuit, FIG. 42 is a view showing the arrangement of electric heater patterns, FIG. 43 is a view showing the arrangement of contact holes, FIG. 44 is a view for explaining the arrangement of a second metal wiring layer, FIG. 45 is a view showing a state wherein shape memory alloy thin film patterns and polyimide films are formed, FIG. 46 is a sectional view, taken along the line 46A—46A of FIG. 45, of a multilayer structure in which the shape memory alloy thin film patterns and the polyimide film are formed, FIG. 48 is a sectional view taken along the line 48B—48B of FIG. 47B, FIG. 50 is a chart showing the waveform of a control signal of the articulated manipulator;

FIG. 51 is a chart, showing the waveforms of signals for feedback-controlling an articulated manipulator, for explaining another control method of the device of the ninth embodiment of the present invention;

FIGS. 52 to 55 are views for explaining a modification of the ninth embodiment of the present invention, wherein FIG. 52 is a view for explaining the pattern of this modification, FIG. 53 is a view for explaining the arrangement of an integrated circuit, FIG. 54 is a view for explaining the arrangement of contact holes, and FIG. 55 is a view showing the arrangement of shape memory alloy thin film patterns and polyimide films;

FIGS. 56 to 59 are views for explaining another control method of the device of the ninth embodiment of the present invention, wherein FIG. 56 is a circuit diagram for explaining arrangement of an integrated circuit, FIGS. 57 and 58 are views for explaining a wiring pattern, and FIG. 59 is a sectional view of the multilayer structure taken along the line 59C—59C of FIG. 58;

FIGS. 60 to 65 are views for explaining the tenth embodiment of the present invention, wherein FIG. 60 is a circuit diagram for explaining an integrated circuit, FIG. 61 is a view for explaining the arrangement of contact holes, FIG. 62 is a view for explaining a wiring structure, FIG. 63 is a view for explaining an electric heater pattern, FIG. 64 is a sectional view of a multilayer structure taken along the line 64D—64D of FIG. 63, and FIG. 65 is a view for explaining the arranged pattern of a shape memory alloy;

FIG. 66 to FIGS. 69A and 69B are views for explaining a device according to the eleventh embodiment of the present invention, wherein FIG. 66 is a view showing the arrangement of resist patterns, FIG. 67 is a view for explaining the arrangement of shape memory alloy thin film patterns, FIG. 68 is a sectional view of a multilayer structure taken along the line 68E—68E of FIG. 67, and FIGS. 69A and 69B are side and plan views, respectively, of an articulated structure;

FIGS. 70A and 70B to FIG. 75 are views for explaining another manufacturing method of the devices of the ninth to eleventh embodiments of the present invention, wherein FIGS. 70A and 70B are side and plan views, respectively, showing a state wherein driving mechanisms are assembled on the articulated structure, FIG. 71 is a sectional view taken along the line 71F—71F of FIG. 70, FIG. 72 is a view for explaining the arrangement of a wiring pattern, FIG. 73 is a sectional view taken along the line 73G—73G of FIG. 72, FIG. 74 is a view showing a multilayer structure in which openings are formed, and FIG. 75 is a sectional view showing a multilayer structure in which electroless plating films are formed in the openings;

FIG. 76A is a perspective view of an articulated manipulator according to the twelfth embodiment of the present invention, and FIG. 76B is a sectional view taken along the line 76B—76B of FIG. 76A;

FIG. 78 is a block diagram of a control circuit; and

FIG. 79 is a block diagram of another control circuit.

DETAILED DESCRIPTION OF THE PREFERRED EMBODIMENTS

The preferred embodiments of the present invention will be described with reference to the accompanying drawings.

FIGS. 1 to 4 show the first embodiment of the present invention. As shown in FIG. 2A, this embodiment exemplifies a medical endoscope 1 to be inserted in the body cavity of a living body. An inserting portion 2 of the endoscope 1 extends from an operating portion 2a thereof and is very thin (with a diameter of about 1 mm).

Figure 2B:
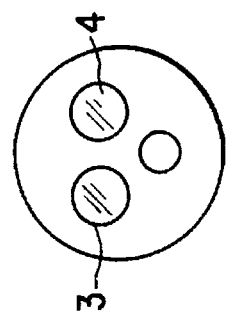
FIG. 2B is a front view showing the distal end portion of the first embodiment of the present invention.
Figure 2A:
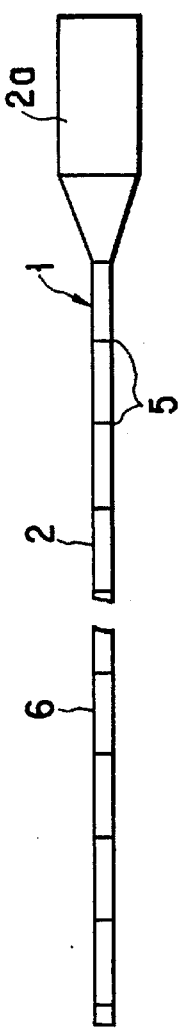
FIG. 2A is a side view of the endoscope of the first embodiment of the present invention.
Figure 3:
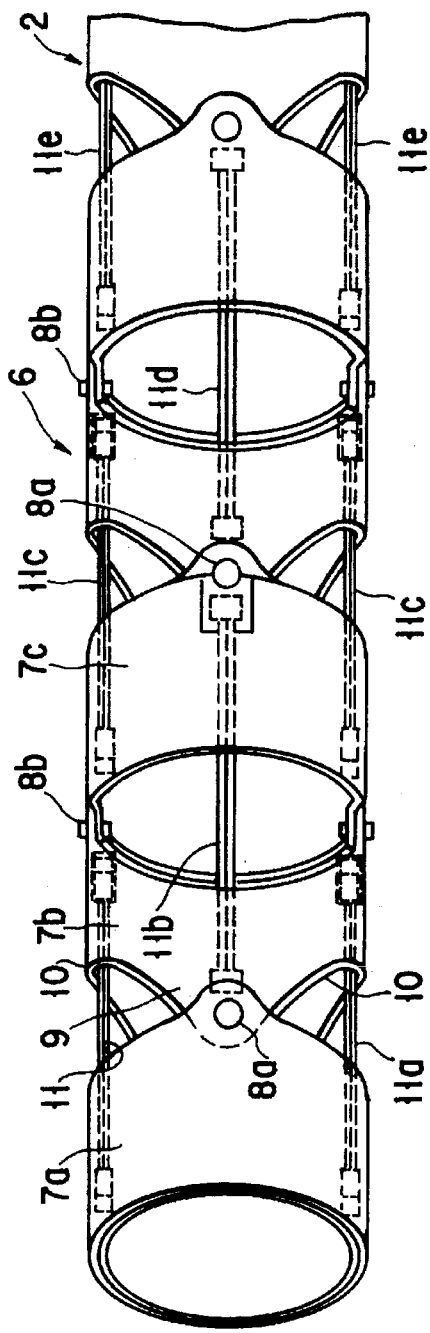
FIG. 3 is a perspective view of the multi-degree-of-freedom flexible tube of the first embodiment of the present invention.
Figure 4:
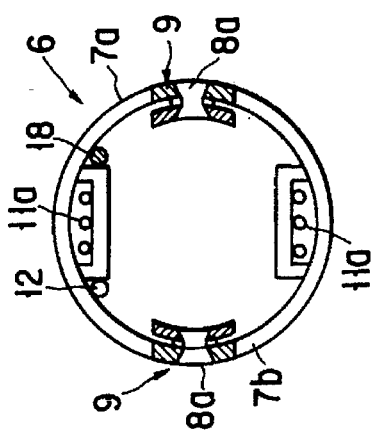
FIG. 4 is a cross-sectional view of the multi-degree-of-freedom flexible tube of the first embodiment of the present invention.

As shown in FIG. 2B, an illumination window 3 and an observation unit 4, e.g., a CCD, are provided on the distal end portion of the inserting portion 2. The inserting portion 2 is constituted by a multi-degree-of-freedom flexible tube or manipulator 6 in which a plurality of bending flex portions 5 are arranged in a row. More specifically, as shown in FIGS. 3 and 4, the manipulator 6 is constituted by arranging a plurality of first and second articulated bodies 7a and 7b and so on, each made of a short cylindrical tube, in a row. The articulated bodies 7a and 7b are pivotally coupled to each other through first and second articulated body fixing pins 8a and 8b. As shown in FIG. 3, each articulated body other than the one located on the end portion is pivotally supported on another articulated body by the pair of first articulated body fixing pins 8a at its one end, and is pivotally supported on still another articulated body by the pair of second articulated body fixing pins 8b at its other end. The articulated body fixing pins of each pair are separated from each other at 180°, and one first articulated body fixing pin 8a and one second articulated body fixing pin 8b are separated from each other at 90°. Thus, each articulated body can pivot about the first articulated body fixing pins 8a and about the second articulated body fixing pins 8b.

Symmetrical relief portions 10 are formed in each of the two end portions of the articulated body 7a or 7b. The relief portions 10 are formed by obliquely cutting the articulated body 7a or 7b so that the two end portions of one articulated body 7a or 7b will not interfere with the two end portions of an adjacent articulated body when the manipulator 6 is flexed at a bending flex portion 9 about the articulated body fixing pins 8a or 8b.

A plurality of pairs of actuators (represented by 11a to 11e) are disposed, inside the articulated bodies 7a and 7b, at locations corresponding to the relief portions 10, i.e., to correspond to the respective bending flex portions 9. One end of each of a pair of actuators 11a separated from each other at 180° is fixed to the articulated body 7a, and the other end of each of this pair of actuators 11a is fixed to the adjacent articulated body 7b through the corresponding bending flex portion 9. Similarly, each actuator 11b of a pair has one end fixed to the articulated body 7b, and the other end fixed to an adjacent articulated body 7c through the corresponding bending flex portion 9.

Each actuator is formed of a linear shape memory alloy whose length changes in accordance with a change in temperature. In other words, the actuator is subjected to a memory treatment so that its length is reduced in the axial direction by a predetermined amount during a heating process from a low temperature to a high temperature.

Figure 1:
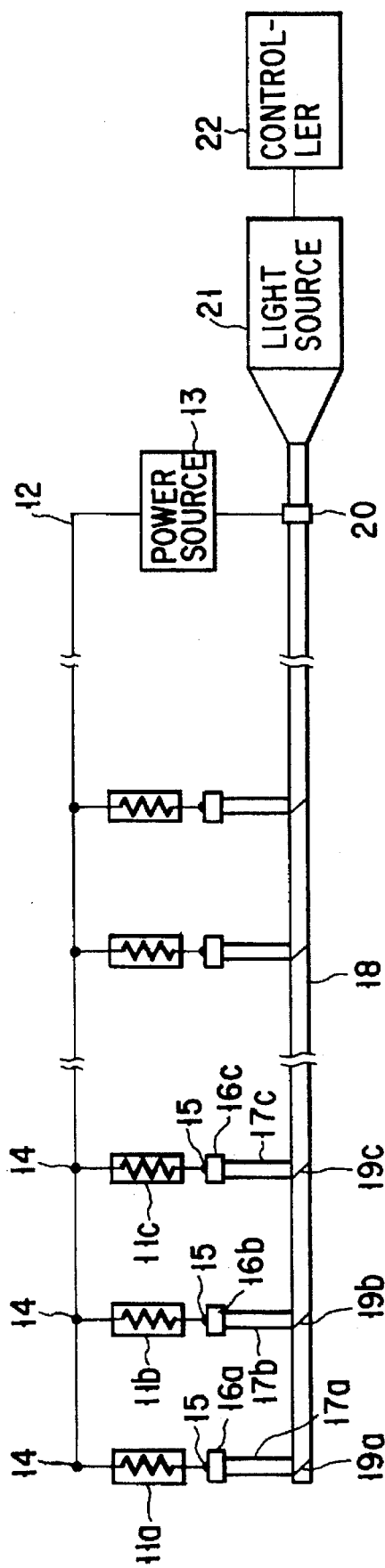
FIG. 1 is a schematic block diagram showing the energy transmission path of a multi-degree-of-freedom flexible tube according to the first embodiment of the present invention.

As shown in FIG. 1, a conductive wire 12 serving as a first common energy transmission path is provided in the flexible tube 6 in the axial direction. One end of the conductive wire 12 is connected to a power source 13 provided to the operator side of the endoscope 1, and the other end thereof is connected to first terminals 14 of the actuators 11a, 11b, . . .

Second terminals 15 of the respective actuators have different band gaps in the absorption range. Thus, the second terminals 15 are electrically connected to photodiodes (represented by 16a to 16c) for detecting light beams having different wavelengths, and electrically optically connected to a common transparent conductor rod 18, serving as the second common transmission path, through independent transparent conductor rods 17a, 17b, and 17c.

Half mirrors 19a, 19b, and 19c made of conductors are provided at connecting portions between the common transparent conductor rod 18 and the independent transparent conductor rods 17a, 17b, and 17c. The half mirrors 19a, 19b, and 19c split the light beam passing through the common transparent conductor rod 18 into a light beam propagating through the rod 18 and light beams directed toward the photodiodes 16a, 16b, and 16c.

The common transparent conductor rod 18 is incorporated in the manipulator 6 in the axial direction together with the conductive wire 12. The proximal end of the common transparent conductor rod 18 is electrically connected to the power source 13 through an electrical connecting portion 20. A large number of series circuits made of the actuators 11a, 11b, and 11c, the photodiodes 16a, 16b, and 16c, and the independent transparent conductor rods 17a, 17b, and 17c are connected in parallel to each other between the common transparent conductor rod 18 and the conductive wire 12.

Figure 5:
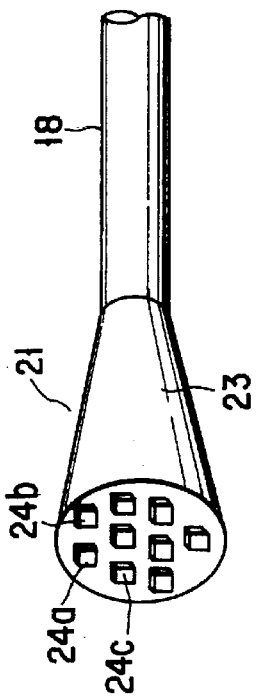
FIG. 5 is a perspective view of the light source of the multi-degree-of-freedom flexible tube of the first embodiment of the present invention.

A light source 21 is connected to the proximal end portion of the common transparent conductor rod 18, and the light source 21 is connected to a controller 22. As shown in FIG. 5, a taper rod 23 is provided to the light source 21. Silver is deposited on the outer circumferential surface of the taper rod 23 to reflect the internal light. A plurality of light-emitting diodes 24a, 24b, and 24c for emitting light beams having wave-lengths corresponding to the detection wavelengths of the photodiodes 16a, 16b, and 16c are provided on the large-diameter end face of the taper rod 2B. The light-emitting diodes 24a, 24b, and 24c are selectively driven by the controller 22 to emit light beams having the same wavelengths as that of the detection wavelengths of the photodiodes 16a, 16b, and 16c. A selective energy means is constituted in this manner.

The operation of the endoscope 1 having the above arrangement will be described.

Assume that the inserting portion 2 of the endoscope 1 is inserted in a body cavity, and the inserting portion 2 is to be bent. In this case, the actuators 11a and 11b independently disposed in the articulated bodies 7a and 7b constituting the flexible tube 6 are selectively powered and heated, so that the lengths of the actuators 11a and 11b change, thereby bending the inserting portion 2.

More specifically, in order to bend the bending flex portions 9 on the distal end of the inserting portion 2, when the first light-emitting diode 24a of the light source 21 is selected, the light-emitting diode 24a emits a light beam having the same wavelength as the detected wavelength of the first photodiode 16a. The emitted light beam is optically transmitted through the common transparent conductor rod 18, transmitted through and reflected by the half mirrors 19c, 19b, and 19a, and is incident on the photodiodes 16c, 16b, and 16a through the independent transparent conductor rods 17c, 17b, and 17a. Only the first photodiode 16a whose detection wavelength coincides with the incident wavelength is turned on to power the actuator 11a having one end connected to the power source 13, thereby heating the actuator 11a. Then, the actuator 11a is contracted in the axial direction to flex the corresponding bending flex portions 9 of the inserting portion 2, thereby guiding the distal end portion of the inserting portion 2 to a treatment target location. Thus, two energy transmission paths are sufficient to simplify the wiring structure. A case has been described wherein only the first actuator 11a is to be driven. However, it is apparent that a plurality of actuators can be driven simultaneously or in the time-shifted manner by turning on a plurality of light-emitting diodes simultaneously or in the time-division manner.

Figure 6:
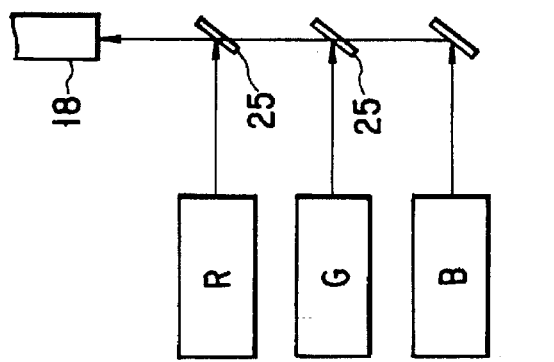
FIG. 6 is a schematic block diagram showing a modification of the first embodiment of the present invention.

FIG. 6 shows a modification of the light source of the first embodiment of the present invention. Actuators are respectively provided to three articulated bodies constituting the flexible tube of an inserting portion. When these actuators are to be driven, laser light sources are selectively turned on to output red, green, and blue light signals R, G, and B, and these light beams are guided to a common transparent conductor rod 18 through half mirrors 25. In this case, when the three color light signals are simultaneously output, these signals are synthesized to produce a white laser beam.

FIGS. 7 and 8 show the second embodiment of the present invention. According to the second embodiment, energy signals to be supplied to respective actuators incorporated in a flexible tube have different frequencies, and these frequencies are selected to selectively drive the actuators.

A plurality of actuators 27a, 27b, and 27c each made of a linear shape memory alloy are provided. First terminals 28 of the actuators 27a, 27b, and 27c are connected to a first common energy transmission path 30 through corresponding LC resonance circuits 29, second terminals 31 thereof are connected to a second common energy transmission path 32, and the first and second common energy transmission paths 30 and 32 are connected to an amplifier 33. That is, the actuators 27a, 27b, and 27c, together with the corresponding LC resonance circuits 29, are connected in parallel to each other to the amplifier 33, and the amplifier 33 is connected to a control circuit 35 through an oscillator 34.

The LC resonance circuits 29 respectively connected to the actuators 27a, 27b, and 27c have different resonant frequencies a, b, and c, as shown in FIG. 8. When the oscillator 34 oscillates a signal having a frequency coinciding with the resonance frequency of the LC resonance circuit 29 of one of the actuator 27a, 27b, and 27c which is to be operated, only the target actuator is powered and heated.

If the oscillator 34 generates signals having frequencies corresponding to a plurality of actuators in the superposed manner, the actuators can be independently and simultaneously controlled, and two energy transmission paths are sufficient in the same manner as in the first embodiment, thus simplifying the wiring structure.

Figure 9:
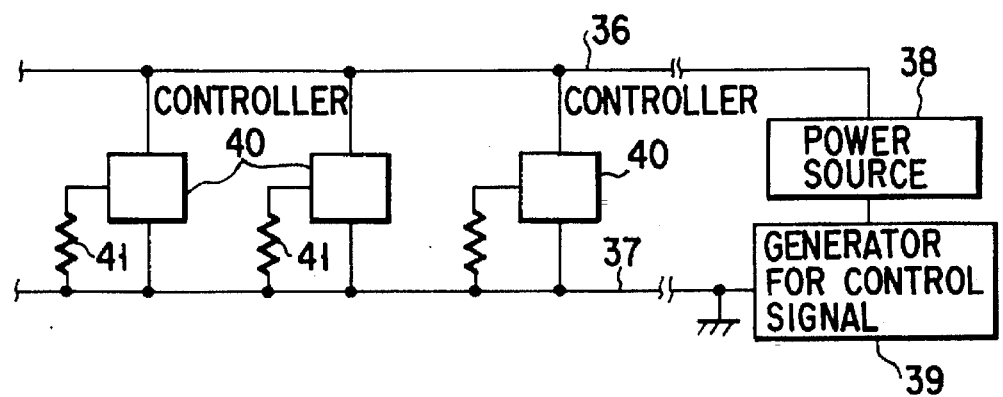
FIG. 9 is a schematic block diagram showing the energy transmission path of a multi-degree-of-freedom flexible tube according to the third embodiment of the present invention.
Figure 10:
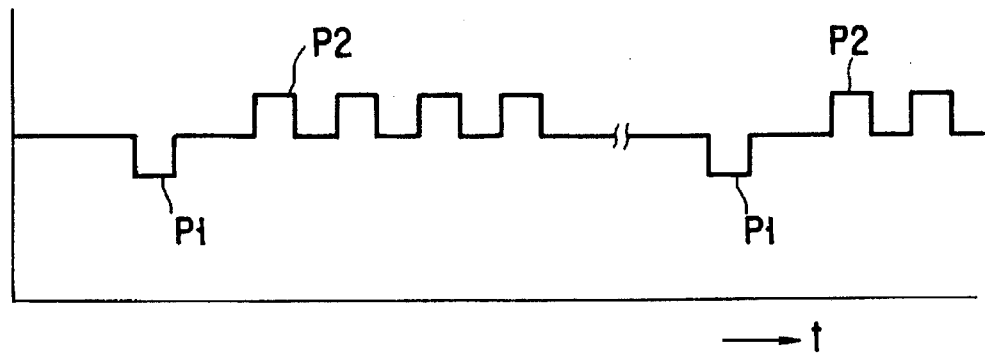
FIG. 10 is a timing chart for explaining a control signal of the second embodiment of the present invention.

FIGS. 9 and 10 show the third embodiment of the present invention. According to the third embodiment, a control signal is supplied to an energy transmission path for supplying energy to a plurality of actuators incorporated in a flexible tube, and one or a plurality of actuators are selectively driven.

Referring to FIG. 9, reference numeral 36 denotes a first common energy transmission path and 37, a second common energy transmission path. The two common energy transmission paths 36 and 37 are disposed in parallel with each other in the flexible tube (the same as that shown in FIG. 2A) in the axial direction. One end of the first common energy transmission path 36 is connected to a DC power source 38, and one end of the second common energy transmission path 37 is connected to a generator 39 for generating a control signal which is connected to the DC power source 38.

A plurality of controllers 40 are connected in parallel to each other between the first and second common energy transmission paths 36 and 37 to correspond to the bending flexible portions of the flexible tube, and actuators 41 each made of a shape memory alloy are respectively provided between the corresponding controllers 40 and the second common energy transmission path 37.

A DC voltage is constantly applied from the power source 38 to the first and second common energy transmission paths 36 and 37, and a control signal generated by the generator 39 is superposed on this voltage. The controllers 40 connected to the respective actuators 41 are turned off (reset) by a reset signal having a negative pulse $P_1$. The number of following positive pulses $P_2$ is counted. Only a controller 40 coinciding with a predetermined pulse count is turned on, and an actuator 41 connected to this controller 40 is powered. FIG. 10 shows a control signal effected at this time. In this manner, the actuators 41 can be selectively powered to flex a target bending flex portion of the flexible tube.

Figure 11:
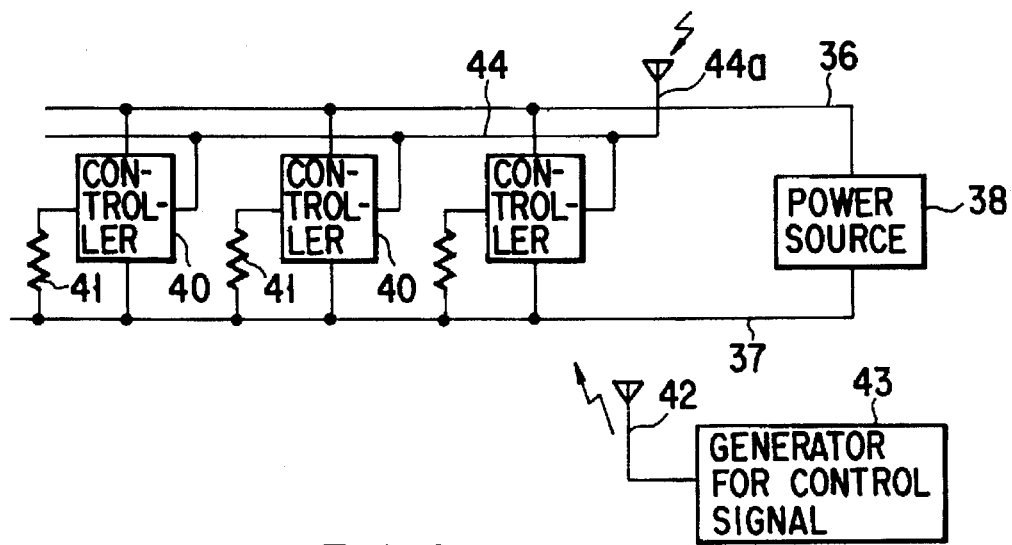
FIG. 11 is a schematic block diagram showing the energy transmission path of a multi-degree-of-freedom flexible tube according to the fourth embodiment of the present invention.

FIG. 11 shows the fourth embodiment of the present invention. The fourth embodiment is basically the same as the third embodiment. According to the fourth embodiment, a control signal is supplied, in a wireless manner, to an energy transmission path for supplying energy to actuators incorporated in a flexible tube, and the actuators are selectively driven.

More specifically, one end of a first common energy transmission path 36 and one end of a second common energy transmission path 37 are connected to a power source 38, and a generator 43 having a transmitting antenna 42 is externally provided to the flexible tube.

A plurality of controllers 40 connected between the first and second common energy transmission paths 36 and 37 are connected to a receiving antenna 44a through a common antenna line 44.

A DC voltage is constantly applied from the power source 38 to the first and second common energy transmission paths 36 and 37, and a control signal transmitted from the transmitting antenna 42 of the generator 43 is received by the receiving antenna 44a and superposed on this DC voltage. The controllers 40 connected to the respective actuators 41 are turned off (reset) by a reset signal having a negative pulse. The number of following positive pulses is counted. Only a controller 40 coinciding with a predetermined pulse count is turned on, and an actuator 41 connected to this controller 40 is powered. Thus, the plurality of actuators 41 can be selectively powered to flex a target bending flex portion of the flexible tube.

Figure 12:
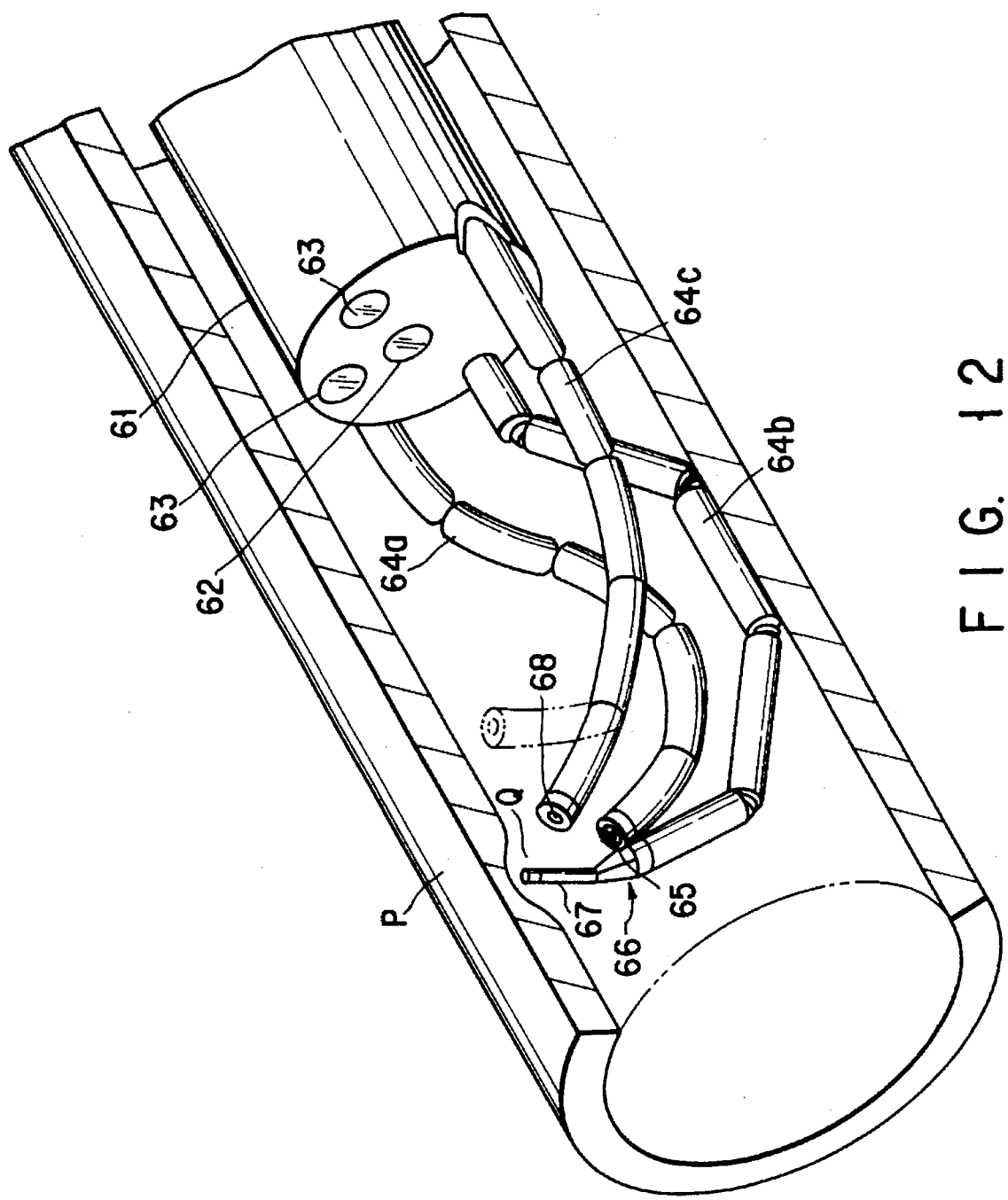
FIG. 12 is a perspective view for explaining a case wherein the multi-degree-of-freedom flexible tube of the present invention is applied to an industrial endoscope.

FIGS. 12 to 14 show applications of the flexible tube shown in the first to fourth embodiments. FIG. 12 shows the use state of an industrial endoscope 61 inserted in an industrial pipe P, e.g., a gas pipe. One illumination window 62 and two observation windows 63 are formed on the distal end face of the industrial endoscope 61.

The proximal end portions of three multi-degree-of-freedom manipulators 64a, 64b, and 64c serving as multi-degree-of-freedom flexible tubes and used for in-pipe operation are fixed to the distal end face of the industrial endoscope 61. The manipulators 64a, 64b, and 64c have flexibly bendable articulated structures.

An illumination unit and an observation unit 65, e.g., a CCD, are provided on the distal end portion of the first manipulator 64a. The first manipulator 64a constitutes a work portion enlarging endoscopic system unit for closely directly observing and monitoring a maintenance portion Q in the industrial pipe P.

A microgripper 66 is provided on the distal end portion of the second manipulator 64b. The microgripper 66 constitutes a tool convey unit for holding a work tool 67, e.g., a welding material, and moving the work tool 67 toward the maintenance portion Q.

A cutting work portion 68, e.g., the light-emitting section for emitting a laser beam, or a grinder, is provided on the distal end portion of the third manipulator 64c. The third manipulator 64c constitutes a work unit which comes close to the maintenance portion Q in the industrial pipe P and performing maintenance, e.g., welding by the laser light and cutting by using the grinder.

When the industrial endoscope 61 having the above-described arrangement is to be inserted in the industrial pipe P to maintain the maintenance portion Q in the industrial pipe P, the inserting portion of the industrial endoscope 61 is inserted in the industrial pipe P and the distal end portion of the inserting portion is guided close to the maintenance portion Q.

While the maintenance portion Q in the industrial pipe P is monitored by the observation unit 65 of the first manipulator 64a, the work tool 67 held by the microgripper 66 of the second manipulator 64b is moved close to the maintenance portion Q, and the maintenance portion Q is maintained by the cutting work portion 68 of the third manipulator 64c.

FIGS. 13 and 14 show the state of a transthorax coronary artery surgical operation. Referring to FIGS. 13 and 14, reference numeral 71 denotes a surgical microrobot; and 72, an endoscope provided independently of the microrobot 71.

Inserting portions 71a and 72a of the microrobot 71 and the endoscope 72 are formed of multi-degree-of-freedom flexible tubes basically having the same structures as that of the first embodiment. A clamp member 73 serving as a treatment unit is provided on the distal end portion of the inserting portion 71a of the microrobot 71 to clamp a coronary artery J.

A treatment tool insertion channel 74 is formed in the inserting portion 72a of the endoscope 72 to open in the distal end portion of the inserting portion 72a. An illumination window and an observation window (neither are shown) are formed in the distal end face of the inserting portion 72a. A resecting treatment tool 137 for resecting a blood vessel and the like is inserted in the treatment tool insertion channel 74.

This surgical microrobot 71 is used during a bypass surgical operation as a treatment of, e.g., myocardial infarction. A bypass surgical operation is done, when the coronary artery of the like is obstructed, to resect the obstructed portion of a blood vessel and to couple the resected ends of the blood vessel.

In this treatment, the inserting portion 71a of the percutaneous microrobot 71 and the inserting portion 72a of the endoscope 72 are separately inserted in the chest of a patient H (shown in FIG. 13). While the interior of the body is observed by the endoscope 72, the distal end portion of the inserting portion 71a of the microrobot 71 is guided to the treatment target portion. In this case, since the inserting portion 71a of the microrobot 71 and the inserting portion 72a of the endoscope 72 have flexibly bendable articulated structures, they can be guided also to, e.g., the rear side of the heart I of the patient H.

After the distal end portion of the microrobot 71 is guided to the treatment target portion, the coronary artery J is clamped by the clamp member 73, and the bypass surgical operation of the coronary artery J is performed by the resecting treatment tool 137 which is inserted through the treatment tool insertion channel 74 of the endoscope 72.

Figure 15:
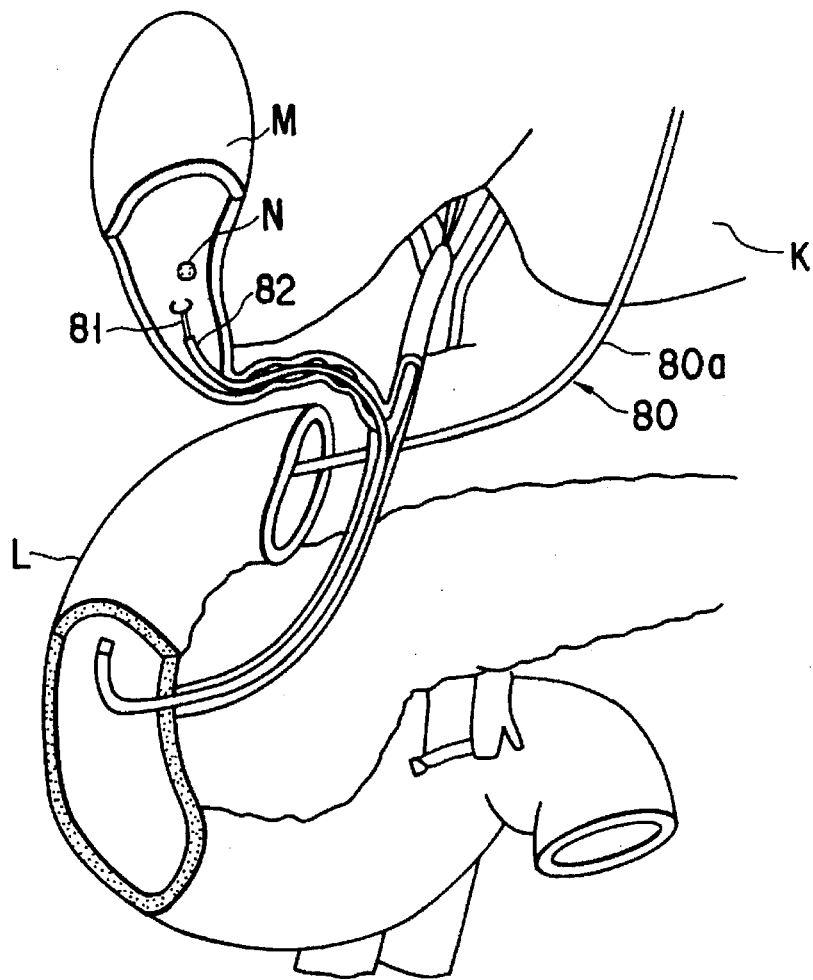
FIG. 15 is a view for explaining a case wherein the multi-degree-of-freedom flexible tube of the present invention is applied to an endoscope to be inserted in the gallbladder.

FIG. 15 shows a state wherein an endoscope 80 is inserted in the gallbladder M of a living body. A treatment tool insertion channel not shown) is formed in an inserting portion 80a of the endoscope 80, and an endoscopic treatment tool 81 is inserted in the body cavity through the treatment tool insertion channel.

The inserting portion 80a of the endoscope 80 is formed by a multi-degree-of-freedom flexible tube basically having the same structure as that of the first embodiment. The inserting portion 80a is guided to the treatment target portion in the body cavity by bending the inserting portion 80a of the endoscope 80 orally inserted in the body cavity.

Referring to FIG. 15, after the inserting portion 80a of the endoscope 80 is orally inserted in the gallbladder M through the esophagus, the stomach, and the intestinum duodenum L, the endoscopic treatment tool 81 is guided into the gallbladder M through the treatment tool insertion channel of the endoscope 80. A treatment is performed by a microgripper 82 provided on the distal end portion of the endoscopic treatment tool 81 such that a gallstone N is destroyed.

Figure 16:
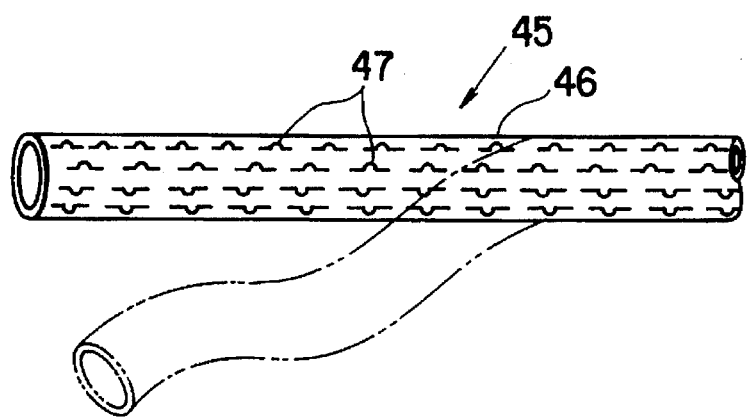
FIG. 16 is a perspective view of an articulated manipulator.
Figure 17:
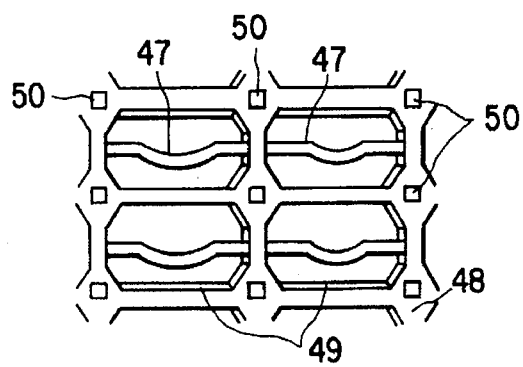
FIG. 17 is a partially enlarged side view of the articulated manipulator of FIG. 16.
Figure 18:
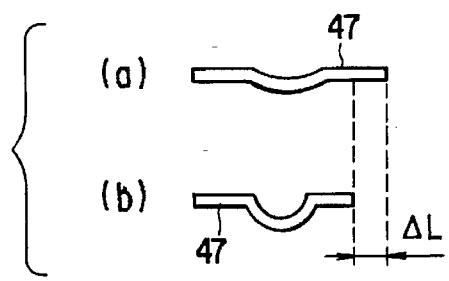
FIG. 18 shows the actuator of the articulated manipulator of FIG. 16.

FIGS. 16 to 19 show an arrangement in which a large number of actuators 47 each made of a shape memory alloy are arranged in a bendable portion 46 of an articulated manipulator 45 in a matrix manner. FIG. 16 shows the outer appearance of the articulated manipulator 45, and FIG. 17 shows an enlarged part of the articulated manipulator 45. Referring to FIG. 17, reference numeral 48 denotes a sheath body. In the sheath body 48, a plurality of windows 49 are formed in a thin cylindrical elastic body (e.g., a stainless steel, an ultra-elastic alloy, and a synthetic resin) in a matrix manner. The actuators 47 each made of a shape memory alloy are disposed to extend through the windows 49 in the axial direction of the sheath body 48.

Each actuator 47 is a linear body which is subjected to a memory treatment. Thus, each actuator 47 is normally almost linear, as shown by (a) in FIG. 18. When heated, the intermediate portion of each actuator 47 in the longitudinal direction is arcuately bent, as shown by (b) in FIG. 18, so that the length of the actuator 47 is decreased by ΔL in the axial direction. Actuator-driving ICs 50 are provided to the sheath body 48 for the corresponding actuators 47.

Figure 19:
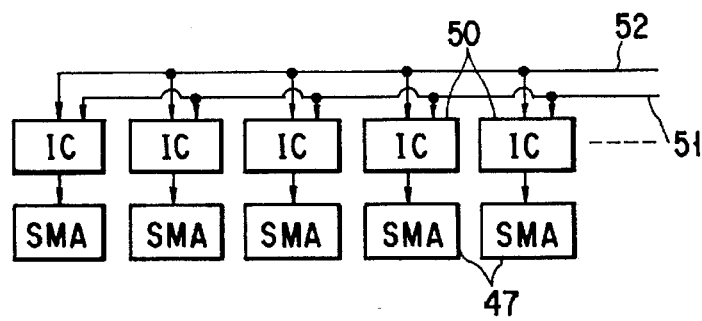
FIG. 19 is a control circuit diagram of the articulated manipulator of FIG. 16.

As shown in FIG. 19, the ICs 50 are connected to a common power source line 51 and to a common control signal line 52. The ICs 50 have different driving frequencies.

Therefore, when a control signal having a frequency corresponding to an IC 50 connected to an actuator 47 which is to be bent, of the large number of actuators 47 arranged in the bendable portion 46 of the articulated manipulator 45 in the matrix manner, is transmitted, this IC 50 is operated, and a driving voltage is supplied to the corresponding actuator 47. When a voltage is applied to this actuator 47 to heat it, the actuator 47 contracts its window 49 in the axial direction, so that the bendable portion 46 of the articulated manipulator 45 is partially bent.

When power supply to this actuator 47 is stopped, the bendable portion 46 of the articulated manipulator 45 is restored to the linear state by the elastic restoring force of the sheath body 48. Hence, the bendable portion 46 of the articulated manipulator 45 can be bent in the complicated manner, and the number of power source lines and the number of signal lines are decreased to decrease the diameter of the articulated manipulator 45.

Figure 20:
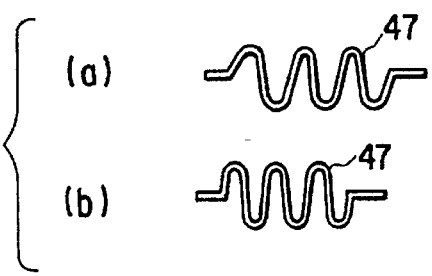
FIG. 20 is a side view showing a modification of the actuator of the articulated manipulator of FIG. 16.
Figure 21:
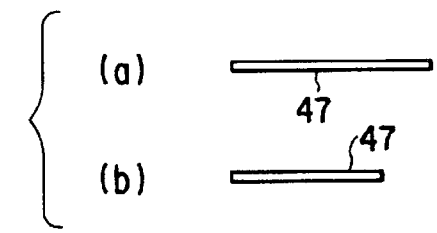
FIG. 21 is a side view showing another modification of the actuator of the articulated manipulator of FIG. 16.

Each actuator 47 may store shapes in the manner as shown in FIG. 20 and FIG. 21 (a) in FIGS. 20 and 21 indicates states before power is supplied and (b) in FIGS. 20 and 21 indicates states after power is supplied.

FIG. 22 and FIGS. 23A and 23B show an arrangement in which a sheath body 54 constituting a manipulator 53 is formed of a thin cylinder made of a shape memory alloy. The sheath body 54 is sequentially notched in the axial direction symmetrically with respect to the axis to form a plurality of pairs of openings 55. Beam portions 56 are provided between each pair of openings 55.

The beam portions 56 are placed in the sheath body 54 to constitute pairs, and the beam portions 56 of each pair are provided at positions shifted from each other by 90° in the circumferential direction. The beam portions 56 of each pair are subjected to a memory treatment such that they are bent in the opposite directions (directions of arrows a). Heaters 57 are adhered on the inner sides of the beam portions 56.

The heaters 57 can be separately heated by, e.g., the means as described in the above embodiments and modifications.

Therefore, when a heater 57 corresponding to a beam portion 56, which is to be bent, of the manipulator 53, is powered, this beam portion 56 is heated and bent to have a stored shape, thereby bending an arbitrary portion of the manipulator 53. In this manner, when the sheath body 54 itself is formed of the shape memory alloy, the diameter of the manipulator 53 can be decreased.

The fifth embodiment of the present invention will be described with reference to FIGS. 24 and 25. FIG. 24 shows the main structure of a bendable flex portion 6 of a multi-degree-of-freedom manipulator used as an articulated manipulator to be inserted in a medical canal cavity or an industrial pipe, e.g., a gas pipe.

The proximal end portion of this multi-degree-of-freedom manipulator is coupled to the operating section on the hand side of the operator. Two types of a plurality of substantially cylindrical metal articulated bodies or bending flex pieces 7a and 7b are alternately arranged in the bendable flex portion 6 of the multi-degree-of-freedom manipulator in the axial direction. The length of the first bending flex pieces 7a is larger than that of the second bending flex pieces 7b. An outer tube (not shown) made of an elastic material is mounted on the outer circumferential surface of each second bending flex piece 7b.

A pair of opposite front projections 7aa are formed on the front end portion of each bending flex piece 7a, and a pair of opposite rear projections 7ab are formed on the rear end portion of each bending flex piece 7a. Similarly, a pair of opposite front projections 7ba are formed on the front end portion of each bending flex piece 7b, and a pair of opposite rear projections 7bb are formed on the rear end portion of each bending flex piece 7b.

The rear projections 7bb of the second bending flex pieces 7b and the front projections 7aa of the adjacent rear bending flex pieces 7a, and the rear projections 7ab of the first bending flex pieces 7a and the front projections 7ba of the adjacent rear bending flex pieces 7b are pivotally coupled to each other through coupling pins 8a, thus forming an articulated structure.

A pair of SMA control circuits (driving means) 90 for controlling the operations of actuators or thermally deformable members 11 each made of a two-directional shape memory alloy (SMA) coil are provided in each second bending flex piece 7b, and a pair of SMA power source posts 91 are provided in each first bending flex piece 7a. The pair of SMA control circuits 90 and the pair of SMA power source posts 91 are arranged at positions shifted from the mount positions of the pair of coupling pins 8a by 90x in the circumferential direction of the corresponding bending flex pieces 7b and 7a.

The thermally deformable members 11 form actuators for bending and flexing the corresponding bending flex pieces 7a and 7b. The first shape of the non-heating time in which the reference coil length is maintained and the second shape of the heating time in which contraction takes place to decrease the coil length to be smaller than the reference coil length are stored in advance in the deformable member 11.

One end of each thermally deformable member 11 is connected to the corresponding SMA power source post 91 provided to the corresponding first bending flex piece 7a, and the other end thereof is connected to the corresponding SMA control circuit 90 of the corresponding second bending flex piece 7b adjacent to this bending flex piece 7a.

when all the thermally deformable members 11 maintain the first shape of the non-heating time, all the bending flex pieces 7a and 7b of the bendable flex portion 6 maintain the substantially linear reference shape. When any one of the thermally deformable members 11 is powered and heated, this heated thermally deformable member 11 is deformed to have the second shape of the heating time and contracted. Then, the corresponding bending flex piece 7a or 7b at this position is locally bendably flexed.

As shown in FIG. 25, a pair of lead wires 92 and 93 are disposed in the bendable flex portion 6. The proximal end portions of the lead wires 92 and 93 are connected to a controller (not shown) provided to the operator side of the multi-degree-of-freedom manipulator. One end of each thermally deformable member 11 is connected to one lead wire 92 through the corresponding SMA power source post 91.

The other end of each thermally deformable member 11 is connected to the corresponding SMA control circuit 90. A pair of discrimination circuits 94, a pair of pulse width modulation (PWM) circuits 95, and a pair of power MOS-FETs 96 are disposed in each SMA control circuit 90. The end portion of each thermally deformable member 11 connected to the corresponding SMA control circuit 90 is connected to the other lead wire 93 sequentially through one power MOS-FET 96, one pulse width modulation circuit 95, and one discrimination circuit 94. A channel (CH1, CH2 to CHn) corresponding to the position of each bending flex piece 7b is set in the discrimination circuit 94 of this second bending flex piece 7b.

When the manipulator is to be operated, a multi-channel PPM (Pulse Phase Modulation) signal transmitted through the lead wire 93 is input to the discrimination circuits 94 of an SMA control circuit 90. The multi-channel PPM signal transmits a control signal proportional to the bending amount, by the SMA, of the thermally deformable member 11 at an arbitrary articulated position as a change in pulse position with respect to a clock pulse.

Of the multi-channel PPM signal, a signal corresponding to each channel is identified by the discrimination circuit 94 of the SMA control circuit 90 with reference to the clock pulse. An output signal from the discrimination circuit 94 is input to the pulse width modulation circuit 95. The pulse width modulation circuit 95 modulates the input signal into a PWM (Pulse Width Modulation) signal proportional to a change in pulse position identified in units of channels. The PWM signal output from the pulse width modulation circuit 95 is supplied to the power MOS-FET 96, and the switching time of the power MOS-FET 96 is changed by the pulse width of the PWM signal, so that the heat generating amount of the SMA of the thermally deformable member 11 is changed.

In the above arrangement, since the plurality of bending flex pieces 7a and 7b of the bendable flex portion 6 of the multi-degree-of-freedom manipulator are bendably flexed by the thermally deformable members 11, only the articulated portion of an arbitrary portion of the entire bendable flex portion 6 can be locally bendably flexed. Therefore, the degree of freedom of the bending flex operation of the bendable flex portion 6 can be increased, and the diameter of the inserting portion of the multi-degree-of-freedom manipulator can be decreased.

The SMA control circuits 90 are disposed in the second bending flex pieces 7b having a smaller length than that of the first bending flex pieces 7a, the SMA power source posts 91 are disposed in the long bending flex pieces 7a, and the thermally deformable members 11 are disposed between the SMA control circuits 90 and the SMA power source posts 91. Therefore, when a thermally deformable member 11 generates heat, most of the heat generated by the thermally deformable member 11 is conducted to the long bending flex piece 7a, and the amount of heat conducted to the bending flex piece 7b can be decreased. Then, the response characteristics of the thermally deformable members 11 are improved, and thermal destruction of the SMA control circuits 90 can be prevented.

The sixth embodiment of the present invention will be described with reference to FIGS. 26A and 26B.

A flexible tube 97 made of a plastic material is provided in a bendable flex portion 6 of a multi-degree-of-freedom manipulator according to this embodiment.

Hinge portions 98 are formed at a plurality of portions of the flexible tube 97 in the axial direction. In this case, a plurality of pairs of opposite notched portions 97a are formed in the flexible tube 97 in the circumferential direction, and a pair of hinge portions 98 are formed by the portions of the flexible tube 97 between each pair of notched portions 97a. Bending flex pieces 7 of the bendable flex portion 6 are formed by the portions between the front and rear hinge portions 98 in the axial direction of the flexible tube 97.

A thermally deformable member 11 formed of a one-directional SMA wire and a return spring 99 formed of a tension spring are disposed in adjacent front and rear bending flex pieces 7. A contraction shape of the heating time, in which contraction takes place to shorten the coil length to be smaller than the reference length of the non-heating time, is stored in advance in the thermally deformable member 11.

Figure 26A:
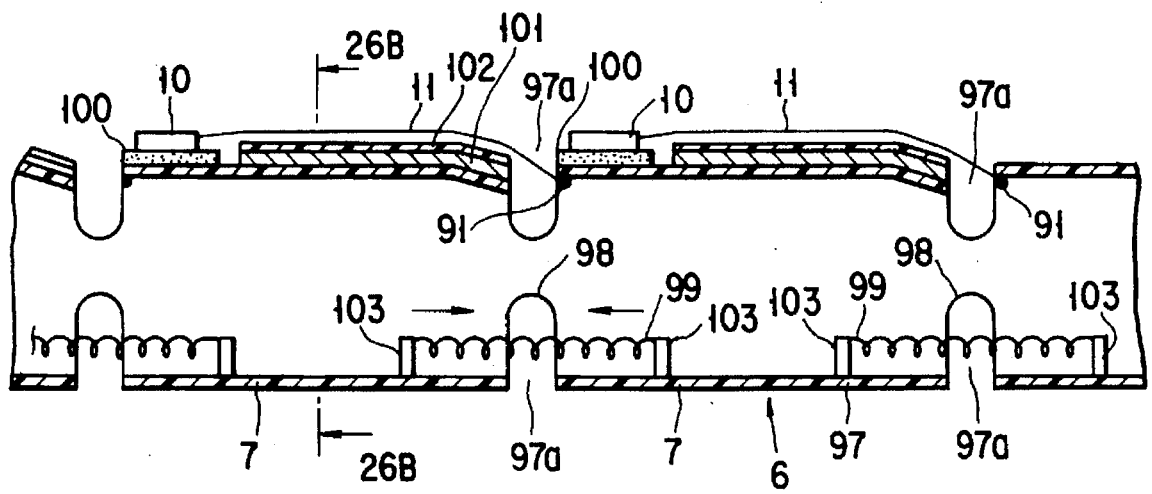
Figure 26B:
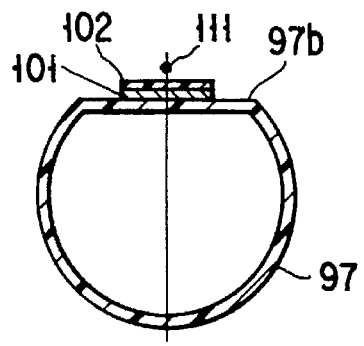

A flat portion 97b shown in FIG. 26B is formed on the outer circumferential surface of each bending flex piece 7. An SMA control circuit 10 for controlling the operation of the thermally deformable member 11 is mounted on the flat portion 97b through a heat insulating plate (heat insulating means) 100.

In this case, the SMA control circuit 10 is disposed on the edge portion of one end side (e.g., a side where the left notched portion 97a of each bending flex piece 7 is located in FIG. 26A) of each bending flex piece 7. One end of the thermally deformable member 11 is connected to the SMA control circuit 10.

The other end of the thermally deformable member 11 extends to the other end side e.g., a side where the right notched portion 97a of each bending flex piece 7 is located in FIG. 26A) of each bending flex piece 7, and is connected to an SMA power source post 91 provided on the inner circumferential surface of an adjacent bending flex piece 7 on the right side in FIG. 26A.

A heat sink plate 101 is disposed on the flat portion 97b on the outer circumferential surface of each bending flex piece 7 to be adjacent to the heat insulating plate 100 of the SMA control circuit 10. An insulting film 102 is formed on this heat sink plate 101. The heat sink plate 101 and the thermally deformable member 11 disposed above the heat sink plate 101 are insulated from each other by the insulting film 102.

A pair of front and rear spring fixing pins 103 project from the inner circumferential surface of each bending flex piece 7 on a side opposite to the thermally deformable member 11, e.g., on the lower end portion of each bending flex piece 7 in FIG. 26A. The return spring 99 extends between the fixing pins 103 of each pair of adjacent bending flex pieces 7 on two sides of each notched portion 97a.

Therefore, the bending flex angle of each bending flex piece 7 is determined by the balance in power between the thermally deformable member 11 and the return spring 99. When all the thermally deformable members 11 maintain the reference shape of the non-heating time, all the bending flex pieces 7 of the bendable flex portion 6 maintain the substantially linear reference shape. If any one of the thermally deformable members 11 is powered and heated, the heated thermally deformable member 11 is deformed to have the contraction shape of the heating time. Then, the bending flex piece 7 at this position is locally bendably flexed about the corresponding hinge portions 98.

In the above arrangement, since the plurality of bending flex pieces 7 of the bendable flex portion 6 of the multi-degree-of-freedom manipulator are bendably flexed by the thermally deformable members 11, only the articulated portion of an arbitrary portion of the entire bendable flex portion 6 can be locally bendably flexed. Therefore, the degree of freedom of the bendable flexing operation of the bendable flex portion 6 can be increased, and the diameter of the inserting portion of the multi-degree-of-freedom manipulator can be decreased.

The SMA control circuit 10 is disposed on the heat insulating plate 100. Therefore, when power is supplied to the thermally deformable member 11 to heat it, heat of the thermally deformable member 11 is conducted to the heat sink plate 101 of the bending flex piece 7 and dissipated from the heat sink plate 101, and heat can be prevented from being conducted from the heat sink plate 101 to the SMA control circuit 10. Then, the response characteristics of the thermally deformable members 11 are improved, and thermal destruction of the SMA control circuits 10 can be prevented.

Figure 27:
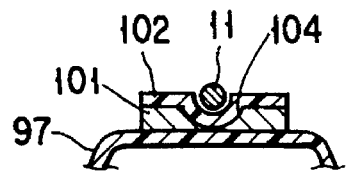
FIG. 27 is a cross-sectional view showing part of a modification of a heat sink plate.

As shown in FIG. 27, a guide groove 104 of the thermally deformable member 11 may be formed in the heat sink plate 101, and the thermally deformable member 11 may be disposed in the guide groove 104. The articulated body may have the same structure as that of the fifth embodiment of the present invention. A bimetal plate may be used, in place of the SMA wire, as the thermally deformable member 11.

The seventh embodiment of the present invention will be described with reference to FIGS. 28 to 32.

Figure 28:
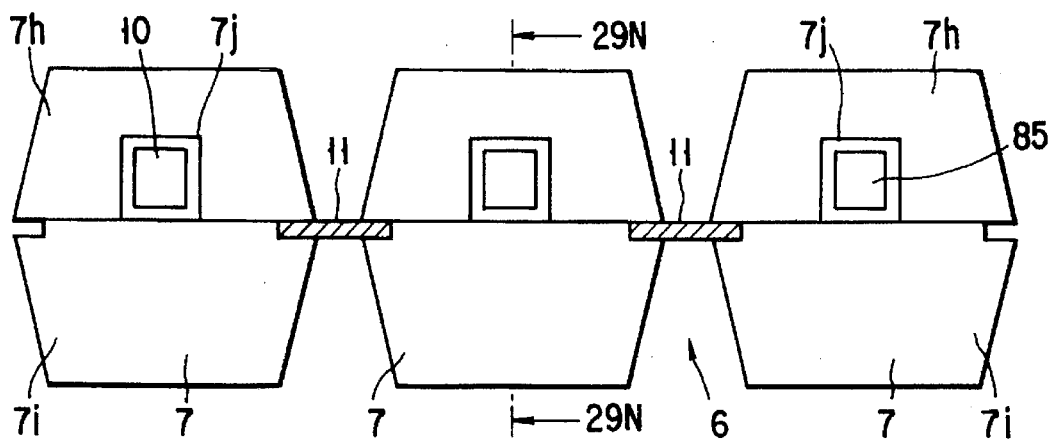
FIG. 28 is a side view showing part of the seventh embodiment of the present invention.

FIG. 28 shows the main structure of a bendable flex portion 6 of a multi-degree-of-freedom manipulator according to the seventh embodiment of the present invention. A plurality of substantially cylindrical bending flex pieces 7 are arranged in the bendable flex portion 6 in the axial direction. A pair of right and left thermally deformable members 11 each made of a two-directional SMA plate are disposed between the adjacent front and rear bending flex pieces 7 for bendably flexing the bending flex pieces 7.

Figure 29:
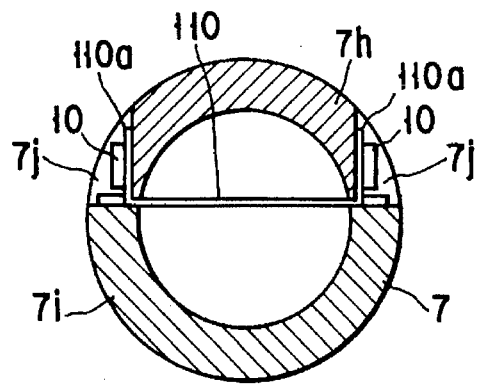
FIG. 29 is a sectional view taken along the line 29N—29N of FIG. 28.
Figure 30:
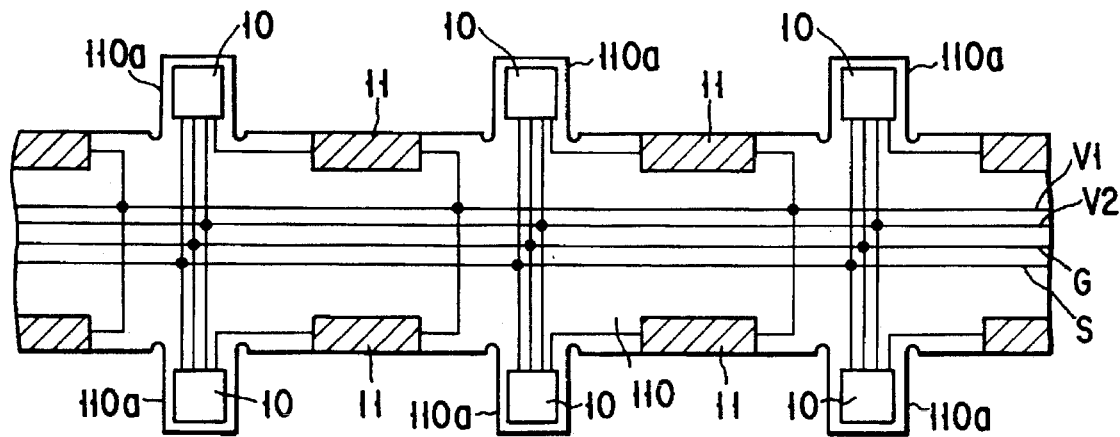
FIG. 30 is a plan view showing a flexible printed circuit board.

As shown in FIG. 29, upper and lower constituent members 7h and 7i each made of an insulating material and having a substantially semicircular section are provided in each bending flex piece 7. The upper and lower constituent members 7h and 7i are mounted to each other through a flexible printed circuit board (FPC) 110 shown in FIG. 30.

Notched portions 7j are formed in the two side surfaces of the upper constituent member 7h. An SMA control circuit 10 for controlling the operation of the thermally deformable member 11 is disposed in each notched portion 7j.

The pairs of right and left thermally deformable members 11 between the adjacent bending flex pieces 7 constituting the bendable flex portion 6, and the SMA control circuits 10 are integrally formed on the flexible printed circuit board 110.

The SMA control circuits 10 are mounted on the flexible printed circuit board 110 by means of, e.g., bonding, and the thermally deformable members 11 are fixed by means of, e.g., soldering. A power source line $V_1$ of the thermally deformable members 11, a power source line $V_2$ of the SMA control circuits 10, a ground line G, and a signal line S are wired on the flexible printed circuit board 110 to form electrical circuit connection between the thermally deformable members 11 and the SMA control circuits 10.

Mount leg portions 110a for the SMA control circuits 10 are provided on the two side portions of the flexible printed circuit board 110. The SMA control circuits 10 on the mount leg portions 110a are adhered to the notched portions 7j on the two sides of the upper constituent member 7h of each bending flex piece 7.

The thermally deformable member 11 maintains the substantially linear reference shape in a moderate temperature state, as indicated by a solid line in FIG. 32, is deformed to have an upward arcuated shape in a high temperature state, as indicated by an alternate long and a short dashed line in FIG. 32, and is deformed to have a downward arcuated shape in a low temperature state, as indicated by an alternate long and two short dashed line in FIG. 32.

In the above arrangement, since the plurality of bending flex pieces 7 of the bendable flex portion 6 of the multi-degree-of-freedom manipulator are bendably flexed by the thermally deformable members 11, only the articulated portion of an arbitrary portion of the entire bendable flex portion 6 can be locally bendably flexed. Therefore, the degree of freedom of the bending flex operation of the bendable flex portion 6 can be increased, and the diameter of the inserting portion of the multi-degree-of-freedom manipulator can be decreased.

Since the SMA control circuits 10 are disposed on the two side surfaces of the upper constituent member 7h of each bending flex piece 7 made of the heat insulating material, when power is supplied to a pair of thermally deformable members 11 to heat them, heat of the thermally deformable members 11 can be prevented from being conducted to the corresponding SMA control circuits 10 through the bending flex piece 7. Then, the response characteristics of the thermally deformable members 11 are improved, and thermal destruction of the SMA control circuits 10 can be prevented.

FIG. 33 shows a multi-degree-of-freedom manipulator 64c fixed on the distal end portion of an industrial endoscope 61 to be inserted in an industrial pipe P like that shown in FIG. 12. Articulated portions A-1 to E-1 of the multi-degree-of-freedom manipulator 64c have lengths $l_1$, $l_2$, $l_3$, $l_4$, and $l_5$ satisfying $l_1 < l_2 < l_3 < l_4 < l_5$, which are gradually decreased toward the distal end portion of the manipulator 64c.

An abrasive work portion 68, e.g., a grinder is rotatably mounted on the distal end face of the articulated portion A-1 at the frontmost end through a rotating shaft 68a. Actuators as described above are independently mounted on the articulated portions A-1 to E-1 to independently and bendably flex the articulated portions A-1 to E-1.

When the multi-degree-of-freedom manipulator 64c is to be used, the articulated portions D-1 and E-1 of the manipulator 64c on the operator side are bent downward and the remaining articulated portions A-1, B-1, and C-1 are bent upward, as indicated by arrows in FIG. 34.

A downward force F is applied to a point 120 on the bottom portion of the inner wall surface of the pipe P by using the articulated portion C-1 as the fulcrum. At this time, the grinder 68 is brought into contact with the upper surface portion of the inner wall surface of the pipe P, and a force f is effected to grind a target portion 121.

In the above arrangement, since the grinder 68 can be stably supported by the articulated portions A-1, B-1, and C-1 by using the articulated portion C-1 as the fulcrum, the abrading operation of the target portion 121 by the grinder 68 can be stably performed.

Then, during use of the multi-degree-of-freedom manipulator 64c, when the articulated portion E-1 of the manipulator 64c on the operator side is bent upward and the remaining articulated portions A-1, B-1, C-1, and D-1 are bent downward, an upward force F is applied to the upper surface portion of the inner wall surface of the pipe P by using a contact point 122 of the articulated portion D-1 as the fulcrum, as indicated by a broken line in FIG. 35.

In this state, when the articulated portions A-1, B-1, and C-1 are bent downward, as indicated by arrows in FIG. 35, the grinder 68 can be brought into contact with the bottom portion of the inner wall surface of the pipe P by the articulated portions A-1, B-1, and C-1 by using the articulated portion D-1 as the fulcrum, and a force f is effected to grind a target portion 123.

Other than the abrading operation by the grinder 68, the multi-degree-of-freedom manipulator 64c can similarly be applied to an endoscopic inspecting operation, a holding and recovery operation by providing a gripper to the distal end of the manipulator 64c, and the like.

In the devices shown in FIGS. 24 to 33, the heat insulating means is provided, so that heat conduction from the thermally deformable member to the thermally deformable member driving means, disposed in the vicinity of the thermally deformable member, can be prevented when a bending flex element of the bendable flex portion is to be bendably flexed by the thermal deformation of the thermal deformable member. Therefore, only an arbitrary portion of the entire bendable flex portion can be locally bendably flexed, the degree of freedom of the bendable flexing operation can be increased, the diameter of the inserting portion can be decreased, and thermal destruction of the driving means of the thermally deformable member, e.g., a shape memory metal wire, can be prevented.

FIG. 36 shows the eighth embodiment of the present invention.

In a multi-degree-of-freedom flexible tube or bending device of this embodiment, a substantially horizontal first elongated thin plate structure 211 and a substantially vertical second elongated thin plate structure 221 are provided. The front end portion of the second plate structure 221 is bonded to the rear end portion of the first plate structure 211 by means of, e.g., welding.

A plurality of notches 212a and 212b (only two notches are representatively shown in FIG. 36) are formed in the first plate structure 211 to extend in a direction perpendicular to the longitudinal direction of the plate structure 211. The distal end openings of the notched portions 212a and 212b are alternately arranged on the two side surfaces of the plate structure 211. A plurality of articulated bodies or bendable elements 211A, 211B, and 211C (only three bendable elements are representatively shown in FIG. 36) are formed in the plate structure 211 by being divided by the notched portions 212a and 212b.

The depth of the notched portions 212a and 212b formed in the side surfaces of the first plate structure 211 is slightly smaller than the lateral width of the plate structure 211, and hinge portions 213a and 213b are formed by the remaining portions of the plate structure 211 behind the notched portions 212a and 212b. The bendable elements 211A and 211B before and after the notched portion 212a, and the bendable elements 211B and 211C before and after the notched portion 212b are coupled by the hinge portions 213a and 213b to be flexible about the hinge portions 213a and 213b.

A pair of support pins 214a and 214b project from the upper surface of the bendable element 211A at the frontmost end to be separated from each other at a predetermined distance in the widthwise direction of the first plate structure 211. One support pin 214a is arranged near the closed end portion of the notched portion 212a, and the other support pin 214b is arranged near the open distal end portion of the notched portions 212a.

Similarly, a pair of support pins 215a and 215b project from the rear end portion of the bendable element 211C. One support pin 215a is arranged on the side of the open distal end portion of the notched portions 212b, and the other support pin 215b is arranged on the side of the closed end portion of the notched portions 212b.

On the first plate structure 211, a pair of coiled operation wires or actuators 216a and 216b made of two-directional shape memory alloys, and a control section 217, e.g., a control IC, for controlling the operations of the operation wires 216a and 216b are disposed. One operation wire 216a has two ends respectively supported by the support pin 214a projecting from the bendable element 211A and the support pin 215a projecting from the bendable element 211C and extends between the support pins 214a and 215a. The other operation wire 216b has two ends respectively supported by the support pins 214b and 215b and extends between the support pins 214b and 215b. The control section 217 is mounted on the upper surface of the bendable element 211C.

One end of the first operation wire 216a is electrically connected to one end of a lead wire 218a, and the other end thereof is electrically connected to one end of a lead wire 218b. One end of the second operation wire 216b is electrically connected to one end of a lead wire 219a, and the other end thereof is electrically connected to one end of a lead wire 219b. The other end of each of the lead wires 218a, 218b, 219a, and 219b is connected to the control section 217.

A plurality of notches 222a and 222b only two notches are representatively shown in FIG. 36) are formed in the second plate structure 221 to extend in a direction perpendicular to the longitudinal direction of the plate structure 221. The distal end openings of the notched portions 222a and 222b are alternately arranged on the two side surfaces of the plate structure 221. A plurality of bendable elements 221A, 221B, and 221C are formed in the plate structure 221 by being divided by the notched portions 222a and 222b.

The depth of the notched portions 222a and 222b formed in the plate structure 221 is slightly smaller than the lateral width of the plate structure 221, and hinge portions 223a and 223b are formed by the remaining portions of the plate structure 221 behind the notched portions 222a and 222b. The bendable elements 221A and 221B before and after the notched portion 222a, and the bendable elements 221B and 221C before and after the notched portion 222b are coupled by the hinge portions 223a and 223b to be flexible about the hinge portions 223a and 223b.

A pair of support pins 224a and 224b project from the side surface of the bendable element 221A at the frontmost end. One support pin 224a is arranged near the open distal end portion of the notched portion 222a, and the other support pin 224b is arranged near the closed end portion of the notched portion 222a.

Similarly, a pair of support pins 225a and 225b project from the rear end portion of the bendable element 221C. One support pin 225a is arranged on the side of the closed end portion of the notched portion 212b, and the other support pin 225b is arranged on the side of the open distal end portion of the notched portion 222b.

On the second plate structure 221, a pair of coiled operation wires or actuators 226a and 226b made of two-directional shape memory alloys, and a control section 227, e.g., a control IC, for controlling the operations of, e.g., the shape memory alloys are disposed.

One operation wire 226a extends between the support pins 224a and 225a of the bendable elements 221A and 221C. The other operation wire 226b extends between the support pins 224b and 225b. The control section 227 is mounted on the side surface of the bendable element 221C.

One end of the operation wire 226a is electrically connected to one end of a lead wire 228a, and the other end thereof is electrically connected to one end of a lead wire 228b. One end of the operation wire 226b is electrically connected to one end of a lead wire 229a, and the other end thereof is electrically connected to one end of a lead wire 229b. The other end of each of the lead wires 228a, 228b, 229a, and 229b is connected to the control section 227.

The control section 217 of the first plate structure 211 and the control section 227 of the second plate structure 221 extend to the operator side of the second plate structure 221 through lead wires 230a and 230b serving as common energy transmission means and connected to an external controller. The control sections 217 and 227 selectively power and heat the operation wires by inputting signals through the lead wires and have been described in detail in the embodiments described above. Hence, a detailed description of the control sections 217 and 227 will be omitted.

The reference shape of the non-powered time in which a coil length having a predetermined reference size is maintained and the contracted shape in which the coil length is smaller than the reference size are stored in advance in each of the operation wires 216a, 216b, 226a, and 226b.

When the operation wires 216a, 216b, 226a, and 226b maintain the reference shade of the non-powered time, the bendable elements 211A, 211B, and 211C of the plate structure 211 and the bendable elements 221A, 221B, and 221C of the plate structure 221 are held in a substantially linearly arranged state.

When power is supplied to any one of the operation wires 216a, 216b, 226a, and 226b to heat it, the heated wire is deformed to have a contracted shape. More specifically, when the operation wire 216b is powered is heated, it is deformed, and the bendable element 211A at the frontmost end is pulled toward the bendable element 211B to close the distal end opening of the notched portion 212a. Then, the hinge portion 213a is elastically deformed and the bendable element 211A at the frontmost end is flexed about the hinge portion 213a.

When the operation wire 216a is powered is heated, it is deformed, and the bendable element 211B is pulled toward the bendable element 211C to close the distal end opening of the notched portion 212b. Then, the hinge portion 213b is elastically deformed, and the bendable element 211B is flexed about the hinge portion 213b.

Similarly when the operation wire 226a is powered is heated, it is deformed, and the bendable element 221A at the frontmost end is pulled toward the bendable element 221B to close the distal end opening of the notched portion 222a. Then, the hinge portion 223a is elastically deformed, and the bendable element 221A at the frontmost end is flexed about the hinge portion 223a.

When the operation wire 226b is powered is heated, it is deformed, and the bendable element 221B is pulled toward the bendable element 221C to close the distal end opening of the notched portion 222b. Then, the hinge portion 223b is elastically deformed, and the bendable element 221B is flexed about the hinge portion 223b.

In the multi-degree-of-freedom flexible tube having the above arrangement, the structure of the articulated structure portion is simplified compared to the conventional articulated structure in which the plurality of bending flex pieces are pivotally coupled through the coupling pins, and the size of the articulated structure portion is simply decreased compared to the conventional articulated structure, thereby decreasing the size of the entire manipulator.

In this embodiment, a pair of actuators are provided to each of the first and second plate structures 211 and 221. However, it will be easily understood that it is preferable to increase the number of bendable elements and to increase the number of actuators in accordance with the number of bendable elements.

In this embodiment, a flat member is used as a plate structure. However, the shape of the plate structure is not limited to this. For example, as shown in FIG. 37, the entire plate structure 211 (221) may be arcuated in the widthwise direction. In this case, the multi-degree-of-freedom flexible tube can be applied to a pipe member, e.g., the bent portion of an endoscope.

The ninth embodiment of the present invention will be described with reference to FIGS. 38A and 38B to FIG. 50.

An articulated manipulator according to the ninth embodiment is constituted by incorporating electrical circuits, shape memory alloy members, and the like in a driving mechanism a and an articulated structure b that are integrally formed. The driving mechanism will be described first in accordance with the steps in manufacturing it.

Figure 39:
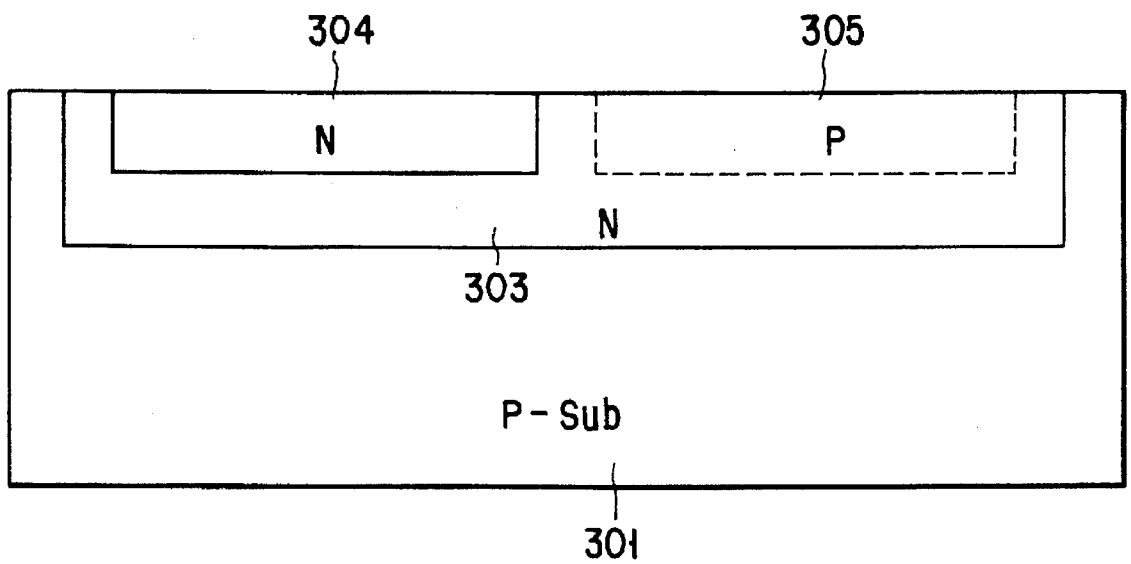

As shown in FIGS. 38A and 38B, n-type lightly doped regions 302 and 303 having a junction depth of 10 fm are equidistantly formed in a row at a plurality of locations on a p-type lightly doped semiconductor substrate 301 having a plane orientation of (100) by phosphorus ion implantation and thermal diffusion. Then, as shown in FIG. 39, in each n-type lightly doped region 303, an n well 304 having an n conductivity type and a p well 305 having a p conductivity type are respectively formed in prospective Pch-MOSFET and Nch-MOSFET regions.

Figure 40:
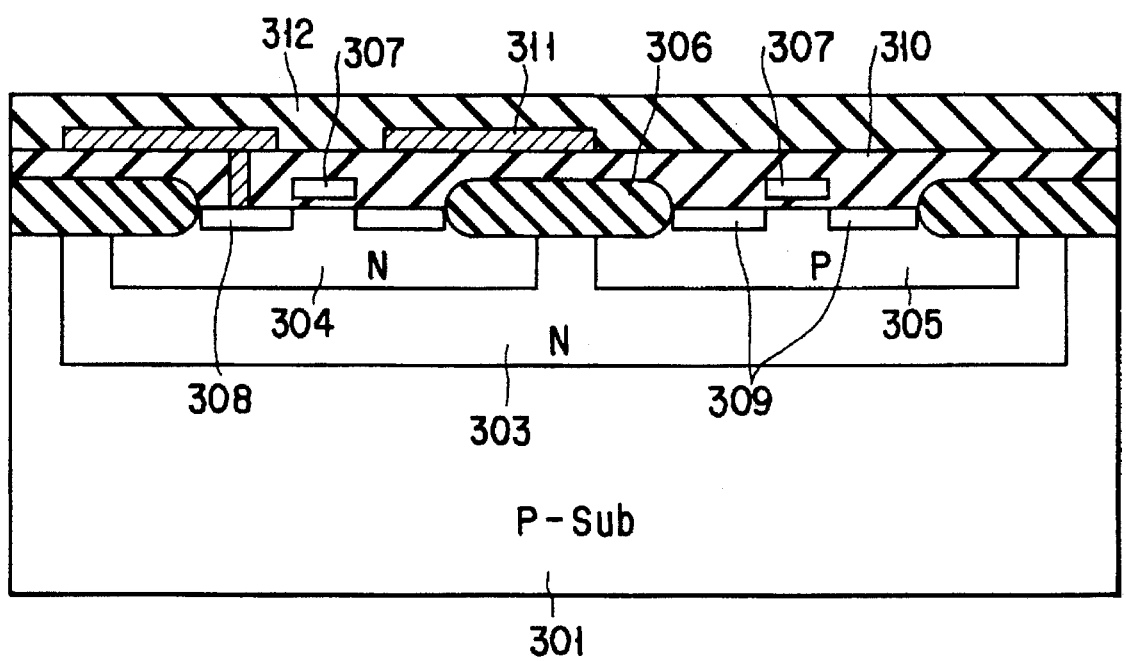

Thereafter, as shown in FIG. 40, field oxide films 306, gate electrodes 307, p-type heavily doped diffusion layers 308, n-type heavily doped diffusion layers 309, a first insulating interlayer 310 made of a silicon oxide film, and first metal wiring layers 311 are formed to form a CMOS integrated circuit in each n-type lightly doped region 303, and a second insulating interlayer 312 made of polyimide is formed on the resultant assembly.

The CMOS integrated circuit formed in the n-type Lightly doped region 303 is wired in this manner to have a predetermined pattern, thereby forming a circuit configuration as shown in FIG. 41. This circuit includes two D flip-flop (DFF) circuits 313, two switching transistors 314, a terminal region 315 of an input power source line, a terminal region 316 of an input GND line, a terminal region 317 of an input synchronizing signal line, a terminal region 318 of an input control line, a terminal region 319 of a first driving line, a terminal region 320 of a second driving line, a terminal region 321 of an output power source line, a terminal region 322 of an output GND line, a terminal region 323 of an output synchronizing signal line, and a terminal region 324 of an output control line. A CMOS integrated circuit formed in the n-type lightly doped region 302 includes, in addition to a circuit configuration the same as that shown in FIG. 41, a signal processing circuit and an input protection circuit (to be described later). A switching transistor is an enhancement type Nch-MOSFET.

Figure 43:
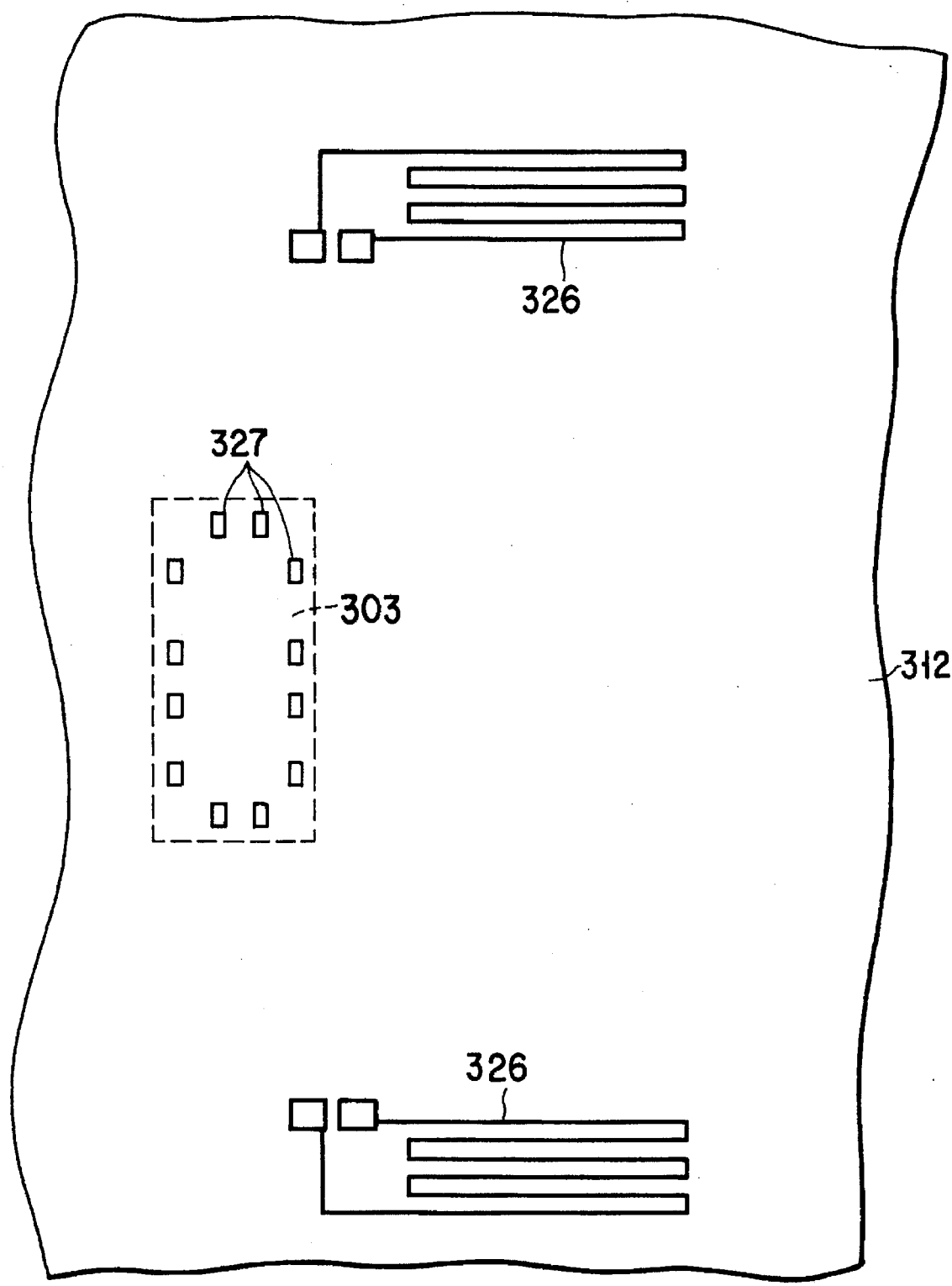
Figure 44:
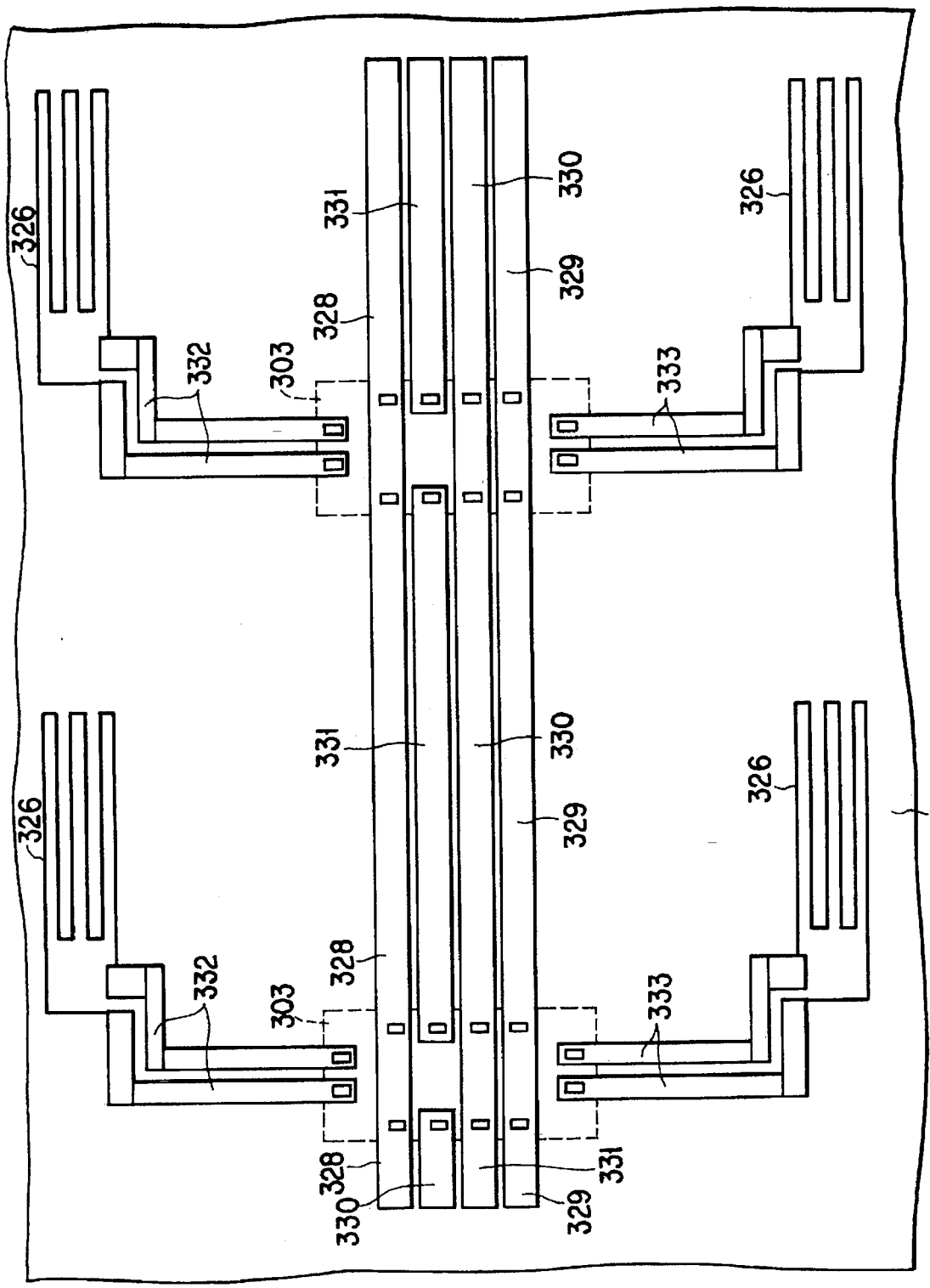

As shown in FIG. 42, electric heater patterns 326 made of Ti thin films are formed at predetermined locations on the two sides of the CMOS integrated circuits on the second insulating interlayer 312 by Ti sputtering and photolithography. As shown in FIG. 43, contact holes 327 are formed at portions of the second insulating interlayer 312 corresponding to the terminal regions 315 to 324 by ordinary photolithography. Then, as shown in FIG. 44, a 1.5-µm thick Al film serving as the second metal wiring layer is formed by sputtering, and the Al film is patterned by ordinary photolithography to connect the contact holes 327 of the power supply lines, the GND lines, the synchronizing signal lines, and the control lines of the respective adjacent electronic circuits formed in the n-type lightly doped regions 303. Then, first driving lines 332 for connecting a power source line 328, a GND line 329, a synchronizing signal line 330, a control line 331, and first driving lines 332 connected to one of two electric heater patterns 326 formed on the side of the first driving lines 332 and the electronic circuit, and second driving lines 333 connected to the other of two electric heater patterns 326 formed on the side of the second driving lines 333 and the electric circuit are formed by the second metal wiring layer. When the second metal wiring layer is etched, an etchant having a higher Al etching rate than a Ti etching rate is used, so that Al can be selectively etched without substantially etching Ti.

Figure 45:
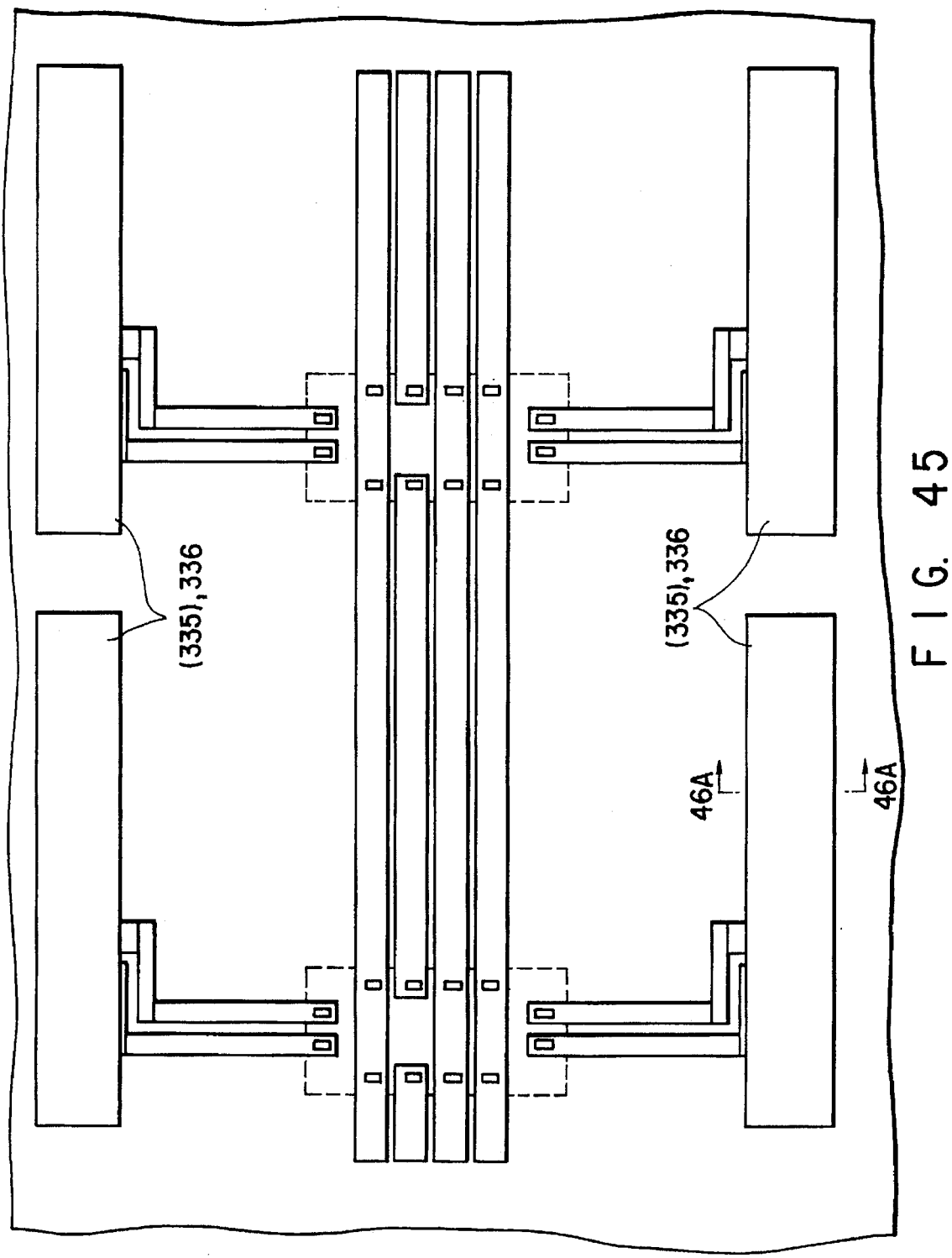

Then, as shown in FIGS. 45 and 46, a 2-fm thick polyimide film serving as a third insulating interlayer 334 is formed on the entire upper surface of the resultant assembly. A 50-µm thick shape memory alloy thin film is formed on the polyimide film by sputtering, and a polyimide film is formed on the shape memory alloy thin film by coating. The memory alloy thin film and the polyimide film thereon are etched by photolithography to form a shape memory alloy thin film pattern 335 serving as the driving body and an polyimide film 336 thereabove.

Regions of the third insulating interlayer 334 and the second insulating interlayer 312 excluding regions where the electronic circuits, wirings, and the shape memory alloy thin film patterns 335 that are described above are formed are etched by photolithography. The major surface of the substrate where the shape memory alloy thin film and the like are formed is covered by a protection film while a voltage of 1 V is applied to the n-type lightly doped regions 302 and 303, regions of the semiconductor substrate other than the n-type lightly doped regions are etched by ECE (Electrochemical Controlled Etching) in a 10 w % ammonium solution of 80° C. In general CMOS circuits, since the power source line is connected to the n wells, the n-type lightly doped regions 302 and 303 can be biased by biasing the power source line 328.

Thereafter, an exposed region of the first insulating interlayer 310 of the silicon oxide film other than the n-type lightly doped regions 302 and 303 is etched by a hydrofluoric acid solution, and the surface protection film is removed. In this manner, the integral driving mechanism a constituted by the wirings and the electric heater patterns 326 that are covered with the soft polyimide film, semiconductor regions partially remaining below the wirings and the electric heater patterns 326 and constituting the electronic circuits, and the upper shape memory alloy thin film (driving body) can be obtained.

Then, the electric heater regions corresponding to the shape memory alloy portions are held in the partially bent state, the assembly is heated at 400° C. for 1 hour, and is quickly cooled, thereby storing the shape. All the shape memory alloy members of the driving mechanism a store the same shape.

Figure 47A:
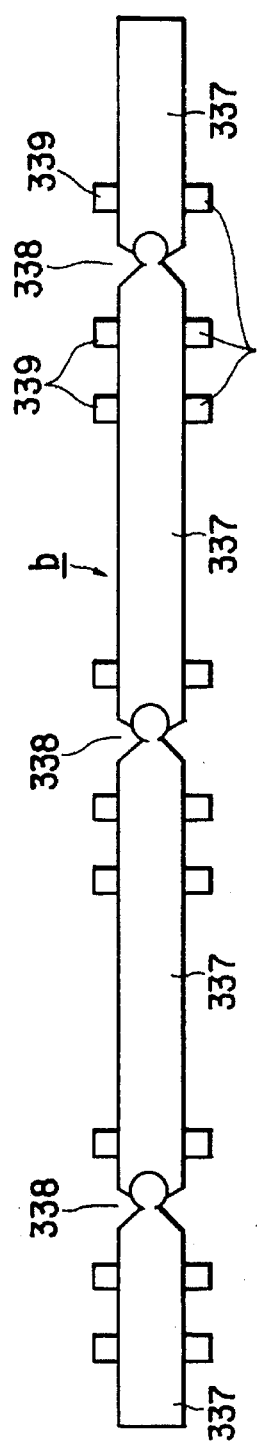
FIG. 47A is a side view of an articulated structure.
Figure 47B:
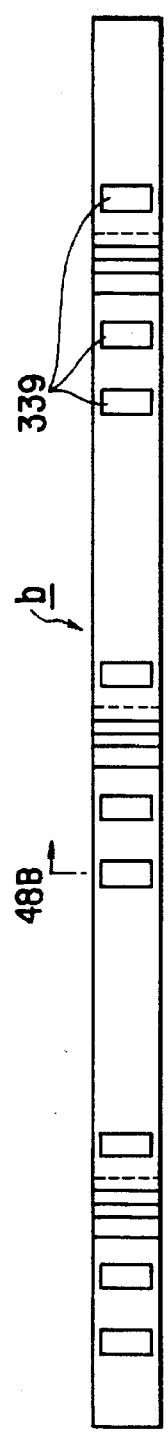
FIG. 47B is a plan view of the same.

An articulated structure b as shown in FIGS. 47A and 47B and FIG. 48 is prepared. The articulated structure b is made of an MIM (Metal Injection Mold). Individual articulated portions 337 of the articulated structure b are coupled to each other through narrow connecting portions 338 so that they are pivotal in an arbitrary direction on one plane. Each articulated portion 337 has three mount portions 339 on its each side.

Figure 49A:
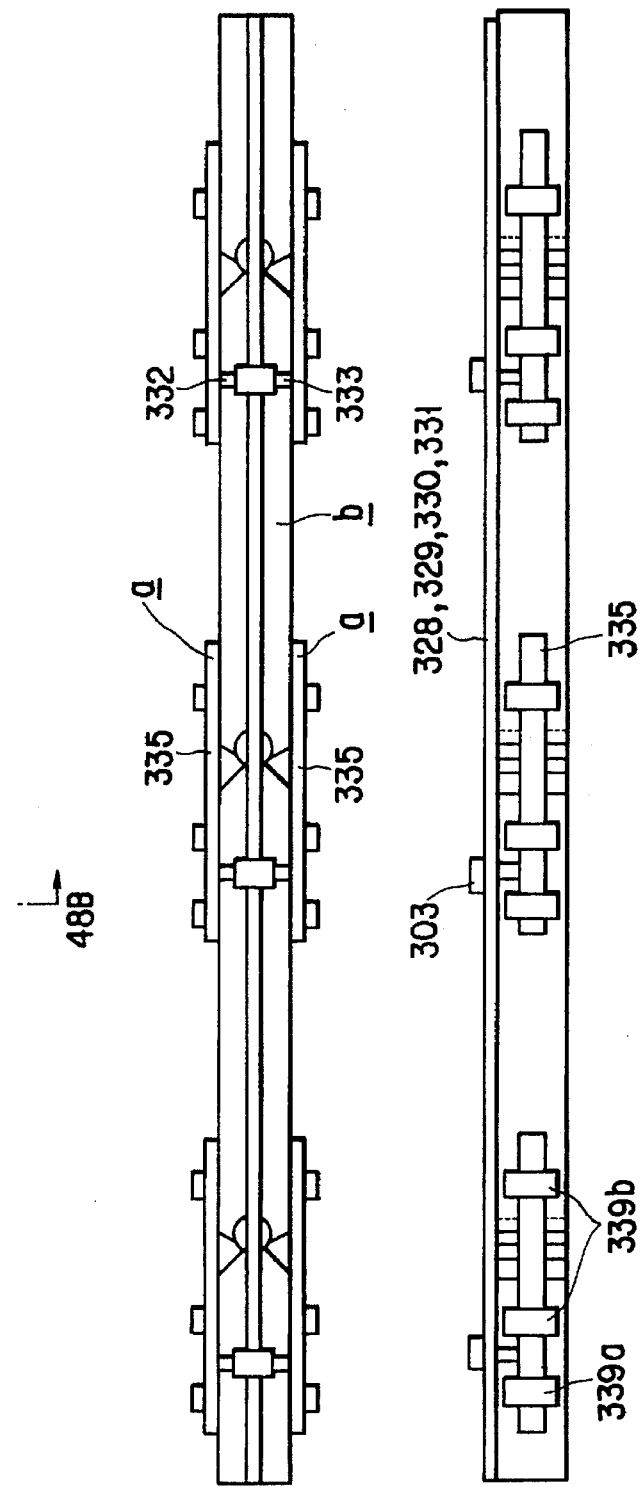
FIG. 49A is a side view of an articulated manipulator constituted by mounting driving mechanisms on the articulated structure.
Figure 49B:
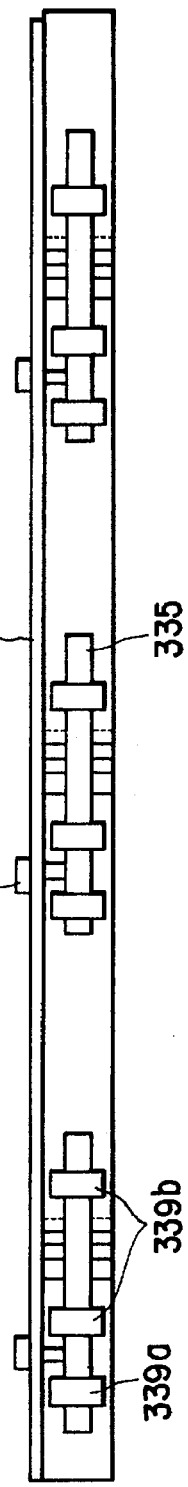
FIG. 49B is a plan view of the same.

As shown in FIGS. 49A ad 49B, two driving mechanisms a each having the integrally formed electronic circuits, shape memory alloy members, and so on are mounted on the articulated structure b. As is seen from FIGS. 49A and 49B, of the driving mechanism a, one electronic circuit portion and a pair of shape memory alloy thin film patterns 335 formed on the two sides of the electronic circuit portion correspond to one articulated portion 337 of the articulated structure b, and the electronic circuit portion is fixed on the upper surface of the articulated structure b.

The pairs of shape memory alloy thin film patterns 335 are bent at driving line portions thereof, so that they are mounted on the three mount portions 339 (339a, 339b, and 339b) on each side of the articulated structure b that extend over two articulated portions 337. More specifically, each shape memory alloy thin film pattern 335 is stationarily mounted by the left mount portion 339a, of the three mount portions 339a, 339b, and 339b, and laterally movably mounted by the two remaining mount portions 339b and 339b. A portion of the shape memory alloy thin film pattern 335 where the electric heater pattern 326 is located is disposed to correspond to the connecting portion 338 of the articulated structure b. The four wirings for connecting the electronic circuit portions are appropriately slackened so that a large stress will not act on them when the corresponding articulated portion 337 is flexed.

In the articulated manipulator constituted by incorporating a plurality of driving mechanisms a in the articulated structure b in this manner, when the shape memory alloy thin film patterns 335 disposed on the two sides of the articulated portion 337 are heated to a temperature equal to a transformation point or more, they apply forces to bend the connecting portion 338 of the articulated portion 337 in opposite directions. Accordingly, the connecting portion 338 can be bent in either direction by heating either of the pair of shape memory alloy thin film patterns 335.

Figure 50:
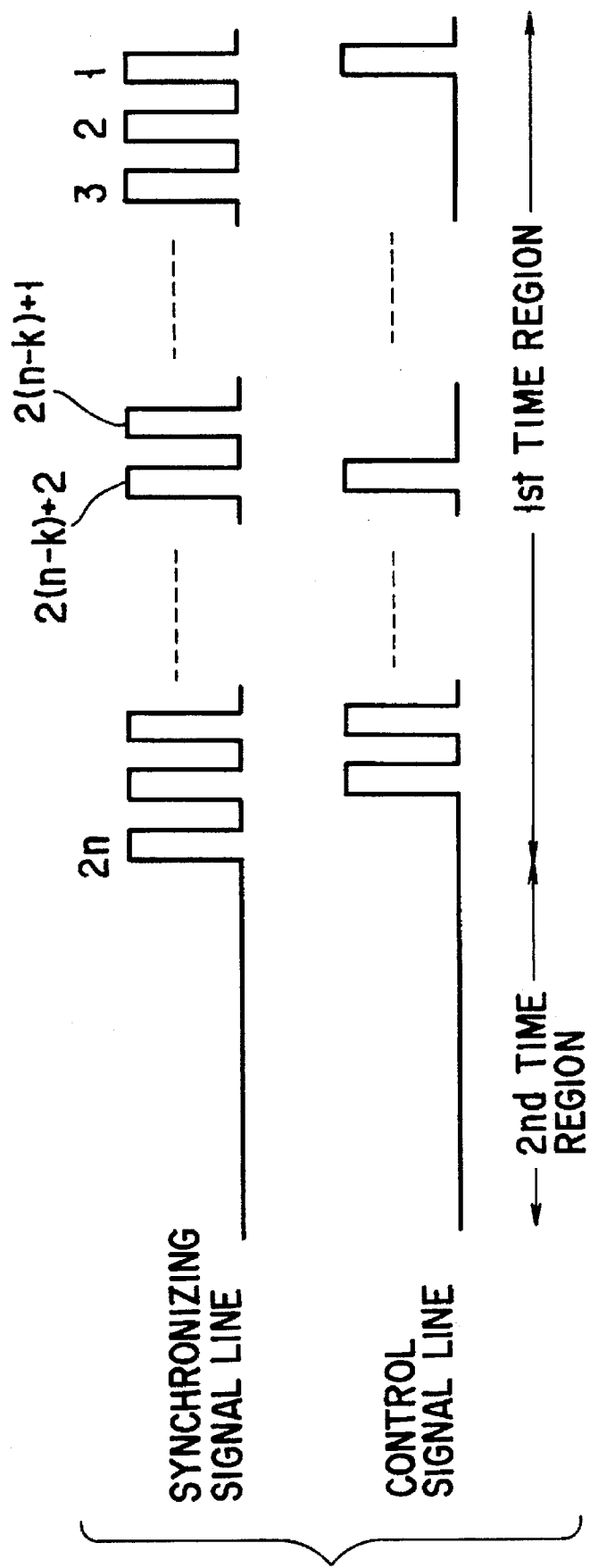

A case will be described wherein the articulated manipulator having the above arrangement is controlled by signals shown in FIG. 50. Assuming that the number of articulated portions 337 is n, the electronic circuits disposed in the articulated portions 337 constitute an 2n-bit shift register. In the first time region, 2n pulses are input to the synchronizing signal line, and pulses are also input to the control signal line.

A kth articulated portion 337 counted from the input side at time T1 at an end of the first time region after completion of input of the 2n pulses will be considered. The electronic circuit of this articulated portion 337 includes $\{2(n-k)+1\}$th and $\{2(n-k)+2\}$th DFFs 313. Since the control signal line at a rise of a $\{2(n-k)+1\}$th synchronizing signal is in an Lo state, the DFF 313 in the second stage of the kth articulated portion 337 is in the Lo state. Since the control signal line at a rise of the $\{2(n-k)+2\}$th synchronizing signal is in an Hi state, the DFF 313 in the first stage of the kth articulated portion 337 is in the Hi state. Therefore, power is supplied to the first driving lines 332 and not to the second driving lines 333 in FIG. 44.

Therefore, in the second time region when the synchronizing signal is not input, of the pair of shape memory alloy members disposed in the kth articulated portion 337, only the one connected to the first driving lines 332 is heated to exceed the transformation temperature, thereby flexing the articulated portion 337 in the predetermined direction. In the first time region, a $\{2(n-k)+1\}$th bit is momentarily set in the Hi state while the control signal is transferred by the shift register. However, if the length of the first time region is sufficiently smaller than the second time region or a time required for increasing the temperature of the shape memory alloy thin film patterns 335, no problem occurs in practice. If this condition is not met, a problem can be avoided by providing a latch circuit between the DFF switching transistors. In this manner, when the first and second time regions are repeated as one unit time and the control signal pulse in the first time region is changed, an arbitrary articulated portion 337 can be flexed in either direction.

According to this arrangement, the control circuit, the electric heater, and the driving circuit are integrally formed, thereby obtaining an articulated driving mechanism having a high power and a large shift amount without requiring an assembly process. Since connection among the respective portions is performed by photolithography, the size of the articulated driving mechanism can be greatly decreased when compared to a structure in which connection is performed by wire bonding.

In the method described with reference to FIG. 50, each articulated portion 337 of the articulated manipulator can be flexed only in one direction in accordance with the stored shape of the shape memory alloy. A method of controlling each articulated portion 337 in a bent state at an arbitrary angle by feedback control, in order to increase the versatility, will be described.

Several methods can be possible to achieve this purpose. A control method using the temperature of the electric heater portion will be described. In the embodiment having the above-described arrangement, a Ti thin film is used as a heat generating body of the electric heater. This Ti thin film will be replaced by a material whose resistance has a high temperature dependency. For example, a conductive organic thin film or a Ti-Ni alloy having a very low transformation temperature may be used. The latter takes an austenite phase in the practical temperature range. Since the temperature dependency of the resistance is relatively high in this range, this Ti-Ni alloy can be utilized. Since the Ti-Ni alloy is highly elastic, it is particularly preferable also from a view point that it is free from a problem of reliability at the electric heater portion caused by plastic deformation even when the shape memory alloy of the driving body is largely strained during transformation.

The method of performing temperature feedback control utilizing the temperature dependency of the shift amount of the shape memory alloy portion, which takes the arrangement as described above, will be described with reference to FIG. 51. In this case, as in the case of FIG. 50, an articulated manipulator has n articulated portions, and the electronic circuits constitute an 2n-bit shift register as a whole.

As is apparent from the timing chart of FIG. 51, a control unit time will be considered by dividing it into first, second, and three time regions. In the first time region, 2n synchronizing signal pulses are output, and the bit state of the first stage is transferred at the first rise of the synchronizing signal pulse. Thus, when only one pulse is supplied first to the control signal line during the first time region, as shown in FIG. 51, only one bit of each of the 2n bits is sequentially set in the Hi state, and an electric heater corresponding to this bit is powered. The temperature can be detected from the resistance of each electric heater by monitoring the current flowing in the electric heater. An electric heater to be powered is determined on the basis of the temperature detected in this manner. In the second time region, necessary pulses are input in the same manner as that described with reference to FIG. 50, and this state is held in the third time region.

Thereafter, although not shown in this timing chart, while the control signal line is kept in the Lo state, 2n pulses are output to the synchronizing signal line to set the respective DFFs in the Lo state, and the process of the first time region is performed again. When this series of processes is performed with a sufficiently short cycle, the shape memory alloy of each driving body can be maintained at a predetermined temperature in accordance with highly controlled feedback.

Figure 53:
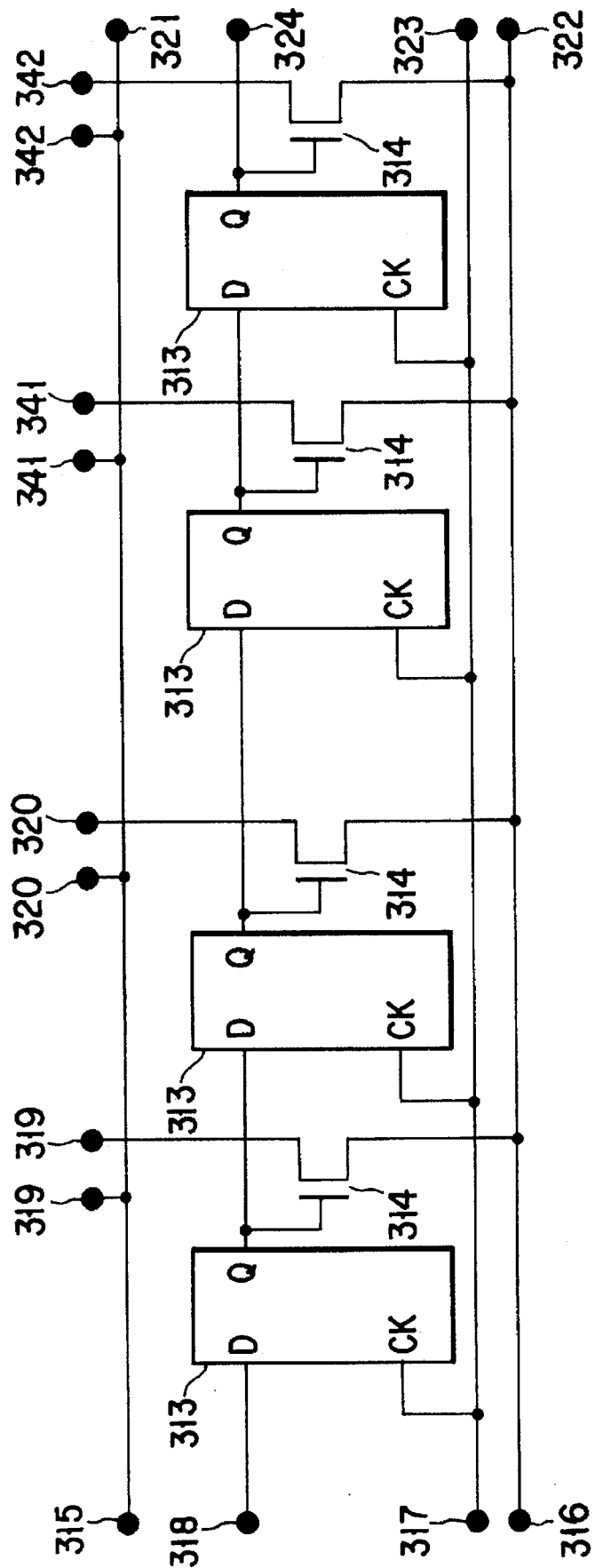

A difference between a method of performing feedback control by using a piezo type strain sensor and the embodiment described with reference to FIGS. 38A to 49B will be described with reference to FIGS. 52 to 55. First, as shown in FIG. 52, an n well 304 identical to that formed in each n-type lightly doped region 303 is formed in a U-shaped manner also in a prospective electric heater pattern region, and an electronic circuit formed in the n-type lightly doped region 303 is modified as shown in FIG. 53. This electronic circuit is obtained by adding 2-bit DFFs and switching transistors to the circuit shown in FIG. 41 described above. The additional portion includes terminal regions 341 of first piezoresistance detection lines and terminal regions 342 of second piezoresistance detection lines (see FIG. 53).

Furthermore, as shown in FIG. 54, contact holes 327 identical to those shown in FIG. 43 are formed in the terminal regions 341 of the first piezoresistance detection lines, the terminal regions 342 of the second piezoresistance detection lines, and on the two ends of each U-shaped N well 304 formed in the prospective electric heater pattern region. N-type heavily doped diffusion layers 309 are formed in the contact holes 327 at two ends of the U-shaped n well 304 to obtain an ohmic contact with a second metal wiring layer to be formed later.

As shown in FIG. 55, in addition to the wirings described with reference to FIG. 44, first piezoresistance detection lines 343 for connecting one of the two n wells 304 serving as two piezoresistance elements, which n well 304 is formed below the electric heater pattern, with the contact holes 327 of the terminal regions 341, and second piezoresistance detection lines 344 for connecting, to the contact holes 327 of the terminal regions 342, the other of the two n wells 304 serving as two piezoresistance elements, which n well 304 is formed below the electric heater pattern are formed.

Thereafter, the articulated manipulator is completed in accordance with the same procedures described in FIG. 45 to FIGS. 49A and 49B. In the circuit configuration shown in FIG. 53, the n well region below the electric heater portion is connected to the power source line. Therefore, in ECE (Electrochemical Controlled Etching), this n well region can remain in the same manner as the n-type lightly doped region on which the electronic circuit is formed.

The control method is basically the same as that shown in FIG. 51. However, since the number of DFFs in one articulated portion is doubled, doubled synchronizing signal pulses are necessary in the first and second time regions. In the first time region, one pulse is sequentially transmitted, and when the first and second piezoresistance detection lines are powered, the current value is monitored, so that the shift amount of each shape memory alloy portion can be obtained by the piezoresistance effect of the n well region below the memory shape alloy portion. An electric heater to be powered is determined on the basis of the shift, detected in this manner, in the shape memory alloy portion, necessary pulses are input in the second time region to turn on the predetermined electric heater line, and this state is maintained in the third time region. Thereafter, while the control signal line is kept in the Lo state, 4n pulses are output to the synchronizing signal line to set the respective DFFs in the Lo state, and the process of the first time region is performed again. When this series of processes is performed with a sufficiently short cycle, the shape memory alloy of each driving body can be maintained at a predetermined temperature in accordance with highly controlled feedback.

Regarding a method of controlling an articulated manipulator by utilizing a change in resistance of the memory shape alloy itself of a driving body, a difference between this method and the embodiment described with reference to FIGS. 38A and 38B to FIGS. 49A and 49B will be described with reference to FIGS. 56 to 59.

Figure 56:
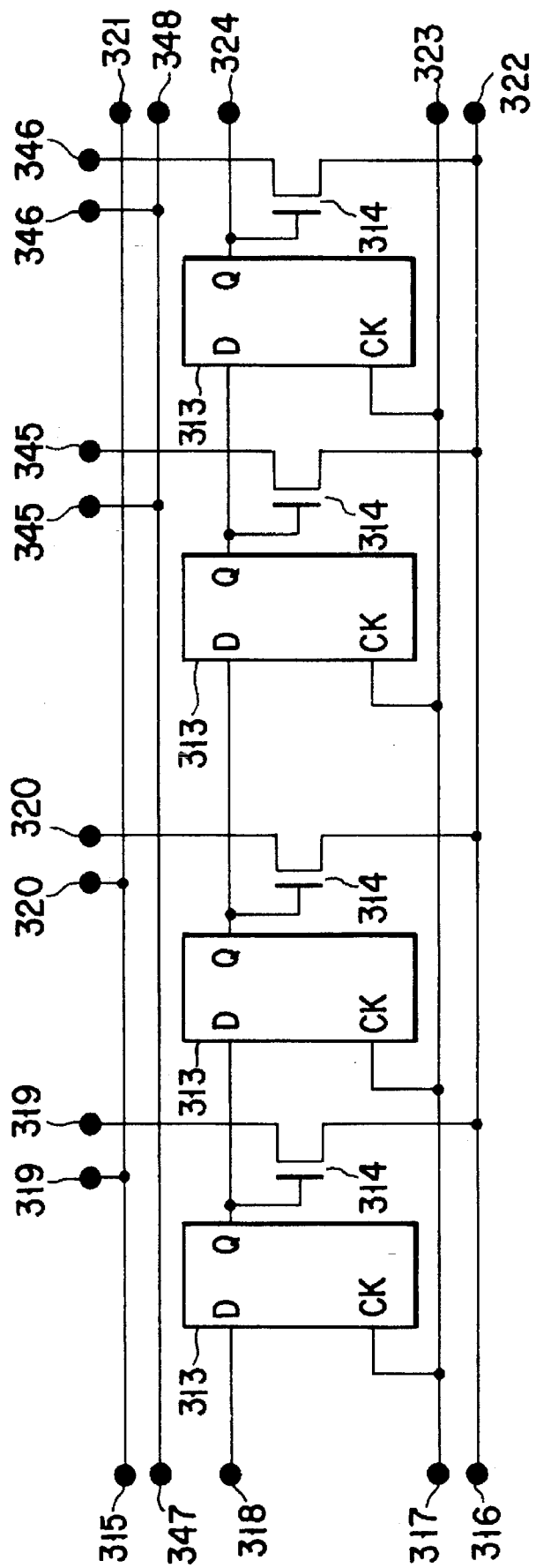

An electronic circuit included in an n-type lightly doped region 303 is modified as shown in FIG. 56. This electronic circuit is obtained by adding 2-bit DFFs 313 and switching transistors 314 to the circuit shown in FIG. 41. The additional portion includes terminal regions 345 of first driving body resistance detection lines and terminal regions 346 of second driving body resistance detection lines. One of each of the first and second terminal regions 345 and 346 is not connected to terminal regions 315 and 321, but is connected to a terminal region 347 of an input resistance detection power source line and a terminal region 348 of an output resistance detection power supply line that are prepared separately. Although not shown, power for the four DFFs 313 in the circuit is supplied from the terminal region 315, in the same manner as in FIGS. 41 and 53.

Figure 57:
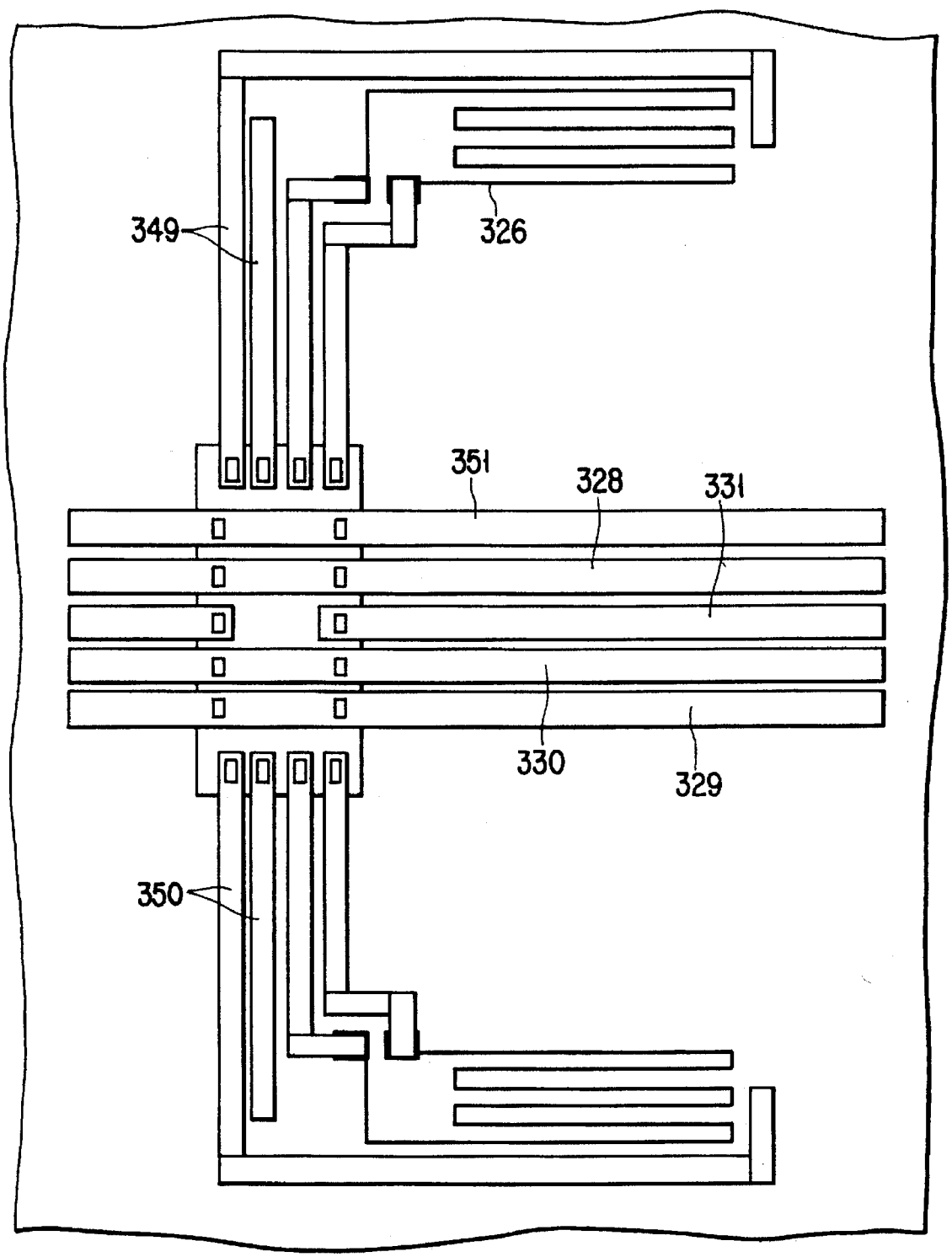

As shown in FIG. 57, in addition to the wiring described in FIG. 44, first driving body resistance detection lines 349 for connecting the two sides of one electric heater pattern to contact holes 327 of the terminal regions 345, second driving body resistance detection lines 350 for connecting the two sides of the other electric heater pattern to the contact holes of the terminal regions 346, and a resistance detection line 351 for connecting the input resistance detection power supply line to the output resistance detection power supply line are formed.

Figure 58:
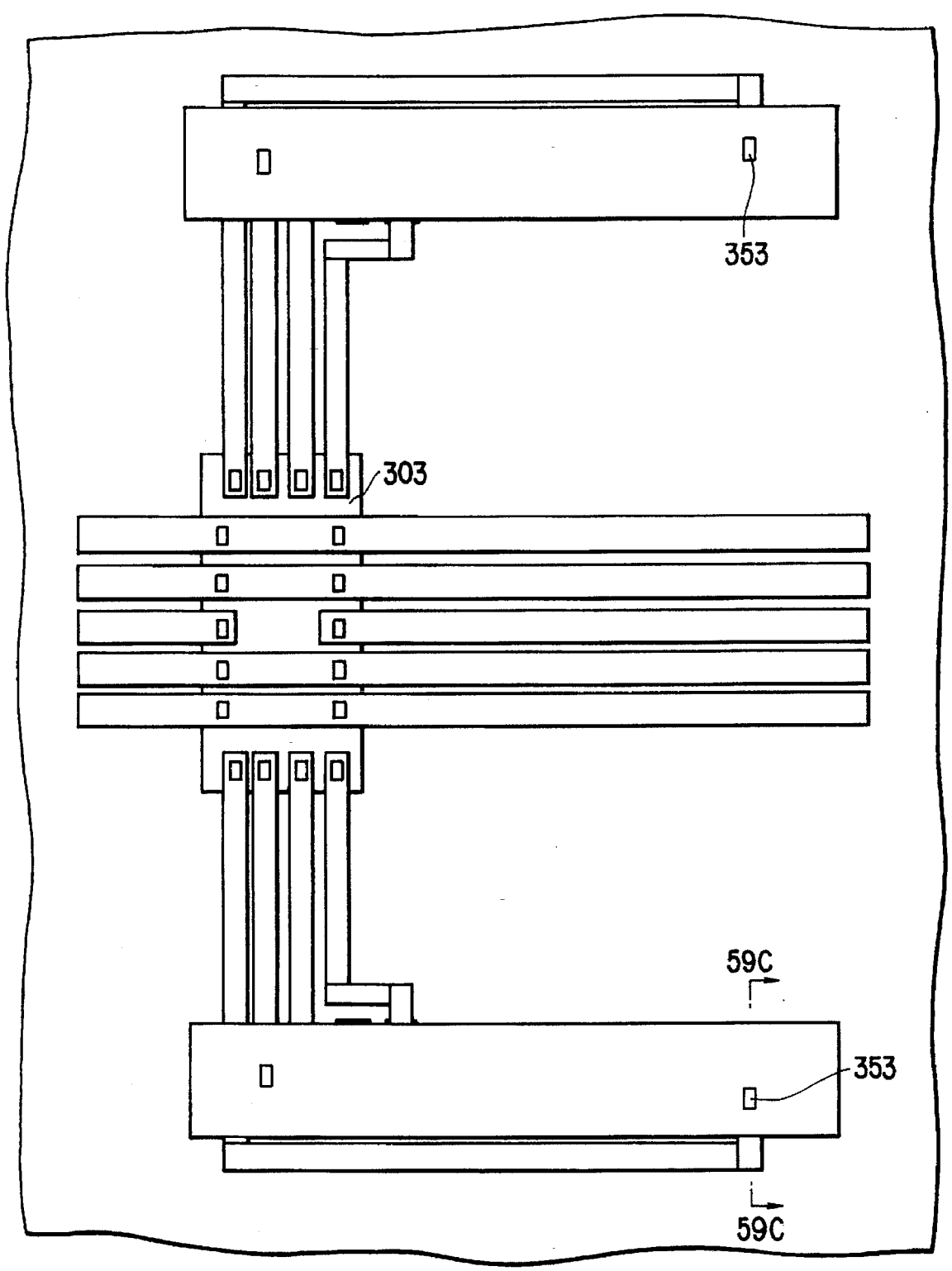

As shown in FIGS. 58 and 59, a third insulating interlayer 352 made of polyimide is formed. Contact holes 353 are formed in the distal ends of the first and second driving body detection lines 349 and 350 by photolithography. A 50-μm thick shape memory alloy thin film is formed on the third insulating interlayer 352 by sputtering in the same manner as in FIGS. 45 and 46, and a polyimide film is formed on the shape memory alloy thin film by coating. The memory alloy thin film and the polyimide film thereon are etched by photolithography to form a shape memory alloy thin film pattern 335 serving as the driving body and an polyimide film 336 thereabove.

Thereafter, the articulated manipulator is completed in accordance with the same procedures shown in FIGS. 47A and 47B to FIGS. 49A and 49B. The control method is basically the same as that described above wherein the piezoresistance elements are used. The power supply used for detecting the resistance of the shape memory alloy portion is different from that used for supplying power to the electronic circuit and the electric heater. Since the resistance of the shape memory alloy portion used as the driving body is very smaller than that of the electric heater, this shape memory alloy portion can be heated during detection of its resistance. The different power supply described above is used in order to prevent this.

Control methods using the temperature of the electric heater, the shift amount of the piezoelement integrally formed with the driving body, and the resistance off the shape memory alloy of the driving body have been described so far. However, these methods can be combined to perform higher-precision feedback control.

When such control is to be actually performed, the temperature of the electric heater, the shift amount of the piezoelement, or the resistance of the shape memory alloy portion must be calculated from the monitored current value, the calculated value must be converted into the shift amount in the shape memory alloy portion serving as the driving body, and a control signal pulse must be generated. An electronic circuit for realizing this is preferably incorporated in the electronic circuit (a portion of the n-type lightly doped region 302 shown in FIGS. 38A and 38B) of the first articulated portion of the articulated manipulator. The articulated manipulator of a microsystem as the object of the present invention is used as one functional unit of the entire system. If this highly sophisticated signal control is possible in the functional unit, it is very advantageous in configuring a large system. Furthermore, if information representing the characteristic value inherent to the driving body or sensor is written in a ROM formed in the electronic circuit of the first articulated portion, the versatility of the articulated manipulator as the functional element can be enhanced.

So far a driving mechanism using a pair of shape memory alloy members that function to flex an articulated portion in opposite directions has been described. A shape memory alloy is capable of performing so-called all-directional shape memory when it is subjected to a specific heat treatment. When such a shape memory alloy is utilized, a driving mechanism (means) can be constituted by one driving body per articulated portion. This embodiment will be described with reference to FIGS. 60 to 64.

Figure 61:
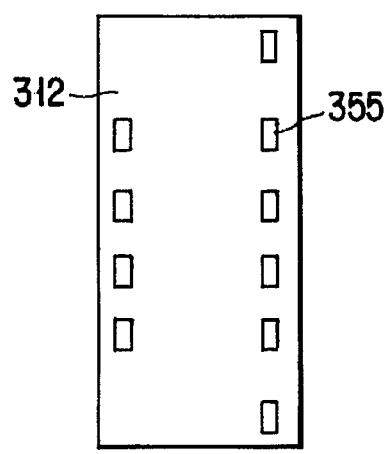
Figure 62:
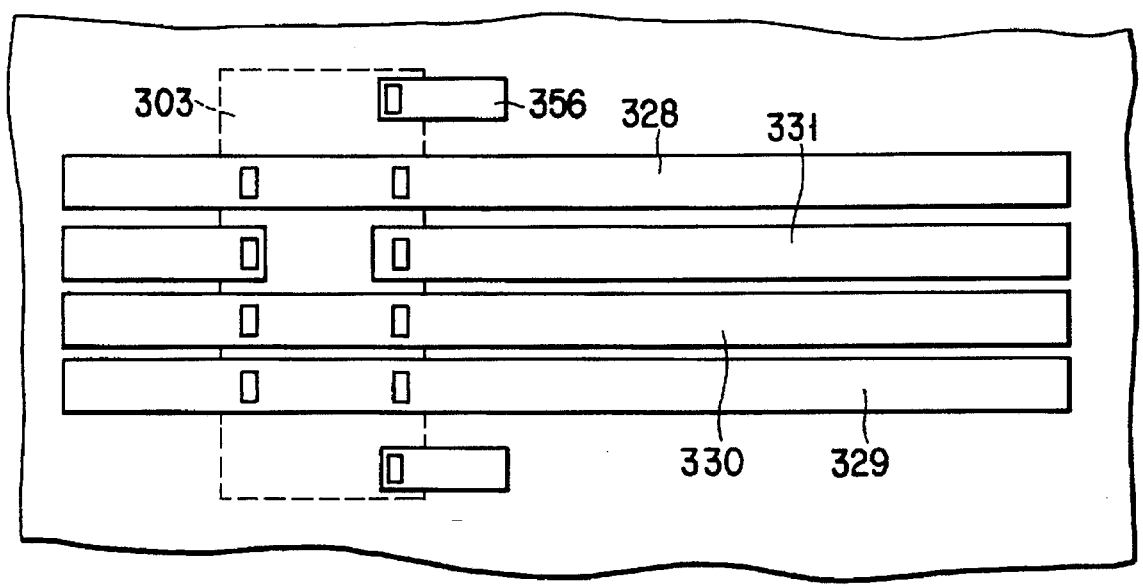
Figure 63:
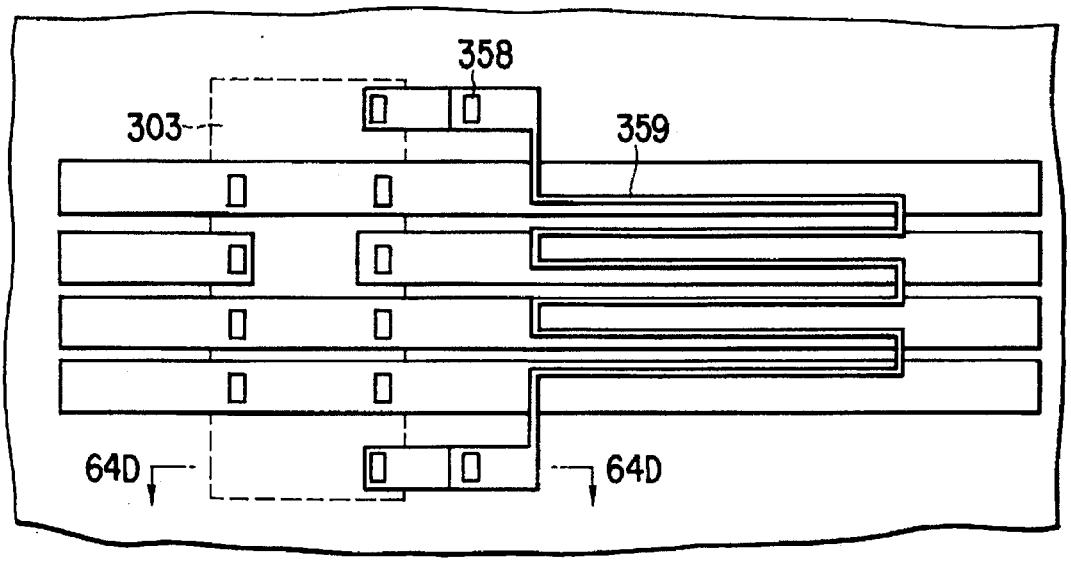
Figure 64:
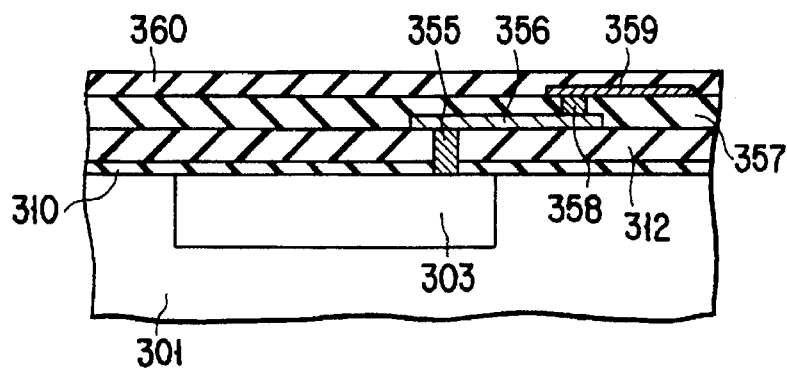

First, an electronic circuit region is formed on a semiconductor substrate 301 in accordance with the same procedures shown in FIGS. 38A and 38B, and FIG. 39. A circuit to be formed in an n-type lightly doped region 303 is designed as shown in FIG. 60. As is apparent from FIG. 60, this circuit is obtained by halving the circuit of FIG. 41 described above, and thus has a pair of terminal regions 354 of driving lines. Subsequently, as shown in FIG. 61, a second insulating interlayer 312 is formed, and contact holes 355 are formed in terminal regions 315 to 318, 321 to 324, and 354 shown in FIG. 60. The contact holes of the power supply lines, the GND lines, the synchronizing signal lines, and the control lines of the adjacent electronic circuits formed in the n-type lightly doped region 303 are connected by photolithography, as shown in FIG. 62, and a power source line 328, a GND line 329, a synchronizing signal line 330, a control line 331, and driving lines 356 extending from the terminal regions 354 of the driving lines are formed by a second metal wiring layer. As shown in FIGS. 63 and 64, a third insulating interlayer 357 made of polyimide is formed, and contact holes 358 are formed at portions of the third insulating interlayer 357 corresponding to the distal ends of the driving lines 356. An electric heater pattern 359 serving as a prospective means for supplying an energy to the driving body is formed by photolithography of a Ti thin film, and the entire assembly is covered with a fourth insulating interlayer 360 made of polyimide, as shown in FIG. 64.

Figure 65:
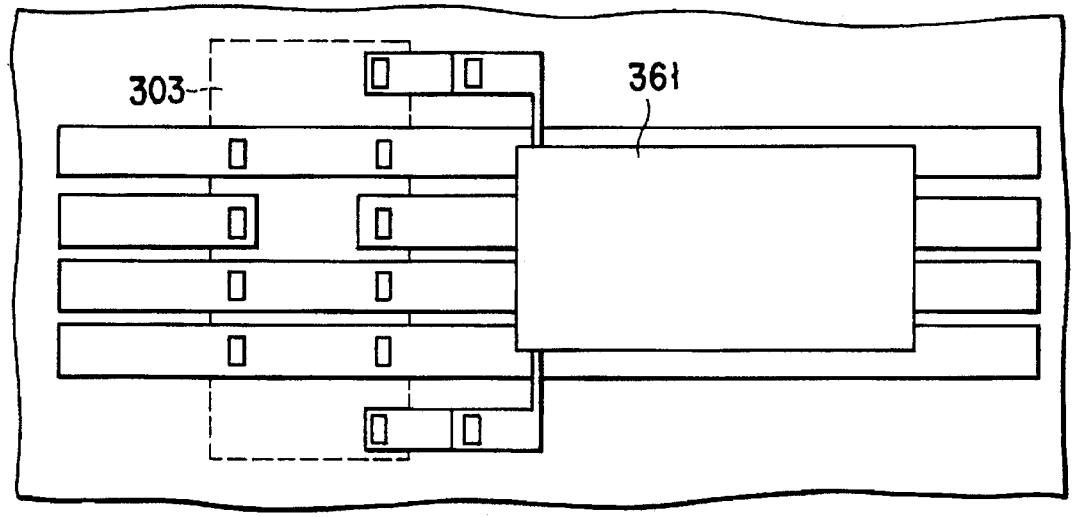
Figure 66:
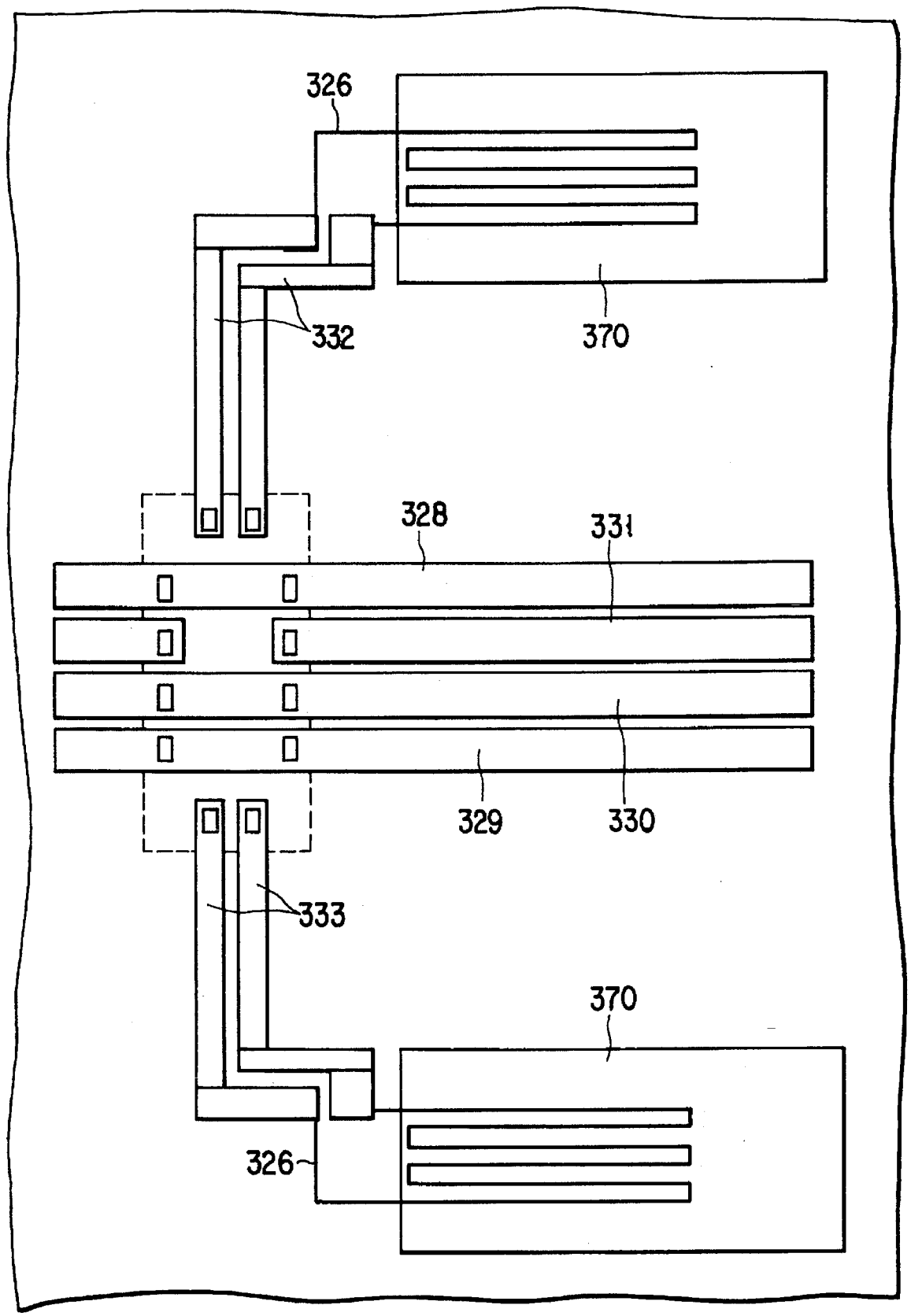

As shown in FIG. 65, the shape memory alloy thin film is sputtered, and a shape memory alloy member B61 serving as a prospective driving body is formed by photolithography. Then, the major surface of the substrate where the shape memory alloy thin film and the like are formed is covered with a protection film, and while a voltage of 1 V is applied to an n-type lightly doped region 302 and the n-type lightly doped region 303, a region of the semiconductor substrate B01 other than the n-type lightly doped region 303 is etched in the same manner as described above. Thereafter, an exposed region of the first insulating interlayer 310 of the silicon oxide film other than the n-type lightly doped regions 302 and 303 is etched by a hydrofluoric acid solution, and the surface protection film is removed. In this manner, the driving mechanism a integrally constituted by the wirings and the electric heater patterns that are covered with the soft polyimide film, semiconductor regions partially remaining below the wirings and the electric heater patterns and constituting the electronic circuits, and the upper shape memory alloy thin film can be obtained. Thereafter, the shape memory alloy is heated while being deformed appropriately, thereby performing all-directional shape memory treatment. when this driving means is incorporated in the articulated structure, the resultant structure can function as the articulated manipulator. The control method is basically the same as that described in FIGS. 47A and 47B except that the number of driving bodies per articulated portion is decreased to one. It is apparent that feedback control of this articulated manipulator can be performed at an arbitrary flex angle by incorporating a sensor in the manner as described above.

So far an articulated manipulator which is driven by causing the shape memory alloy to store the bending displacement has been described. A shape memory alloy generally has a larger power if it is caused to store expansion and contraction shapes. This embodiment will be described with reference to FIG. 66 to FIGS. 69A ad 69B.

An electronic circuit, a wiring, and an electric heater are formed in accordance with the same procedures as in FIGS. 38A and 38B to FIG. 44. A polyimide film serving as a third insulating interlayer and a positive resist film are formed. The resist film is exposed and developed by photolithography, thereby forming resist patterns 370.

Figure 67:
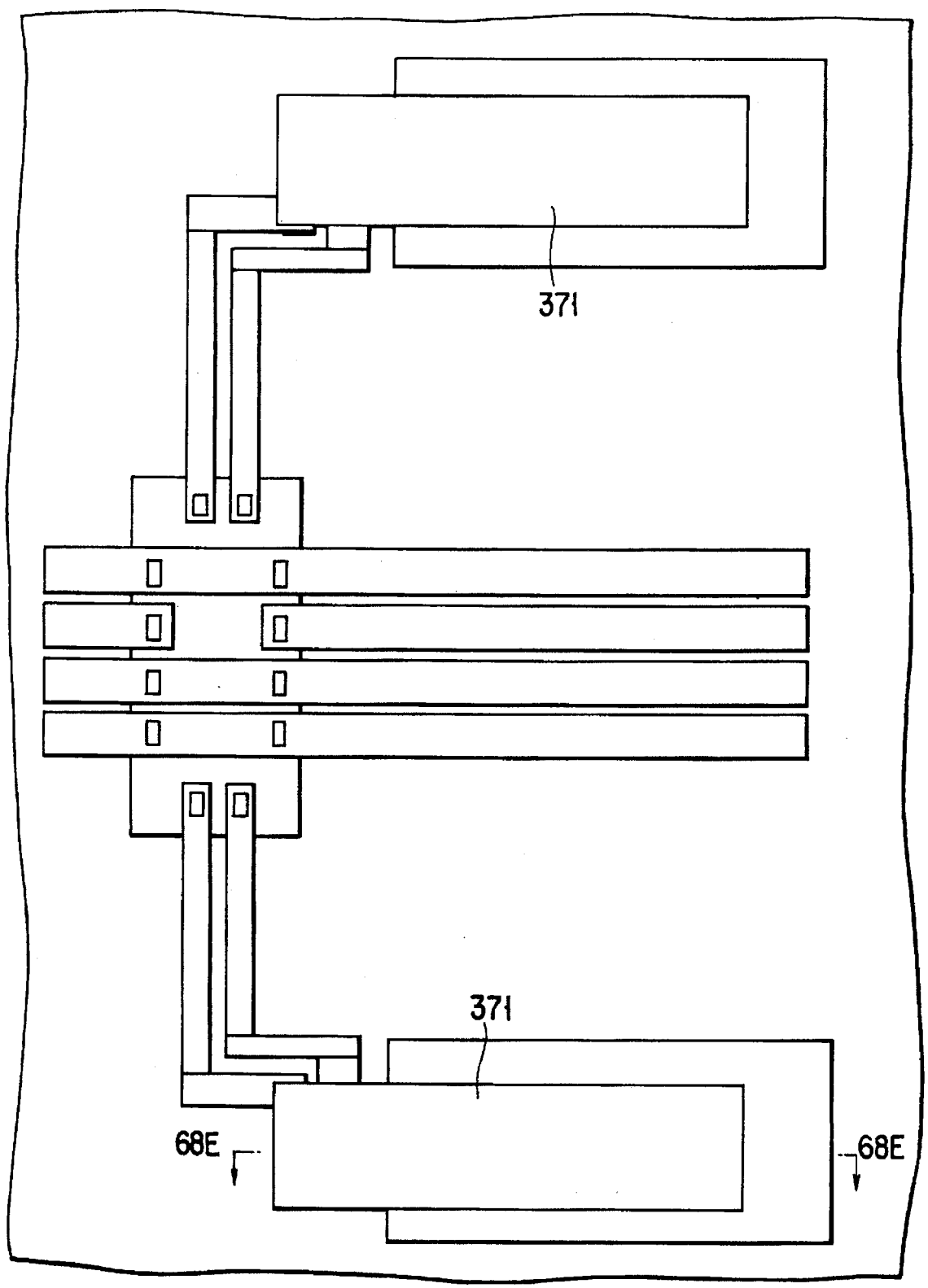
Figure 68:
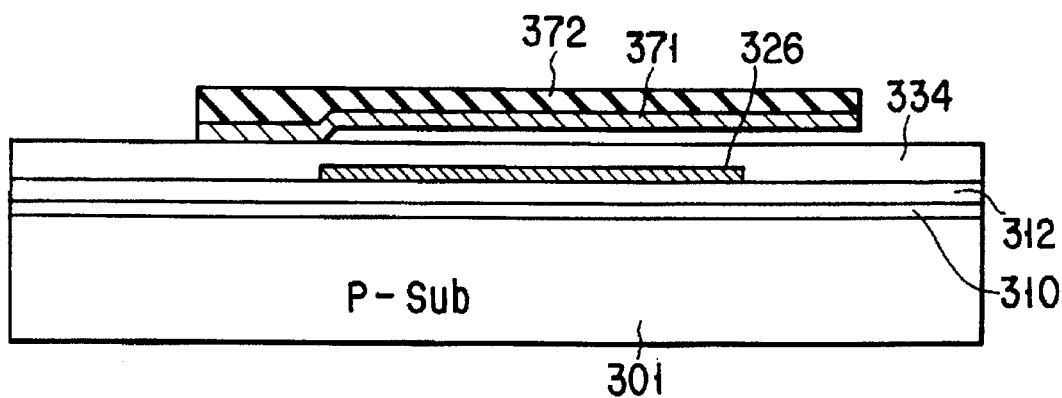
Figure 71:
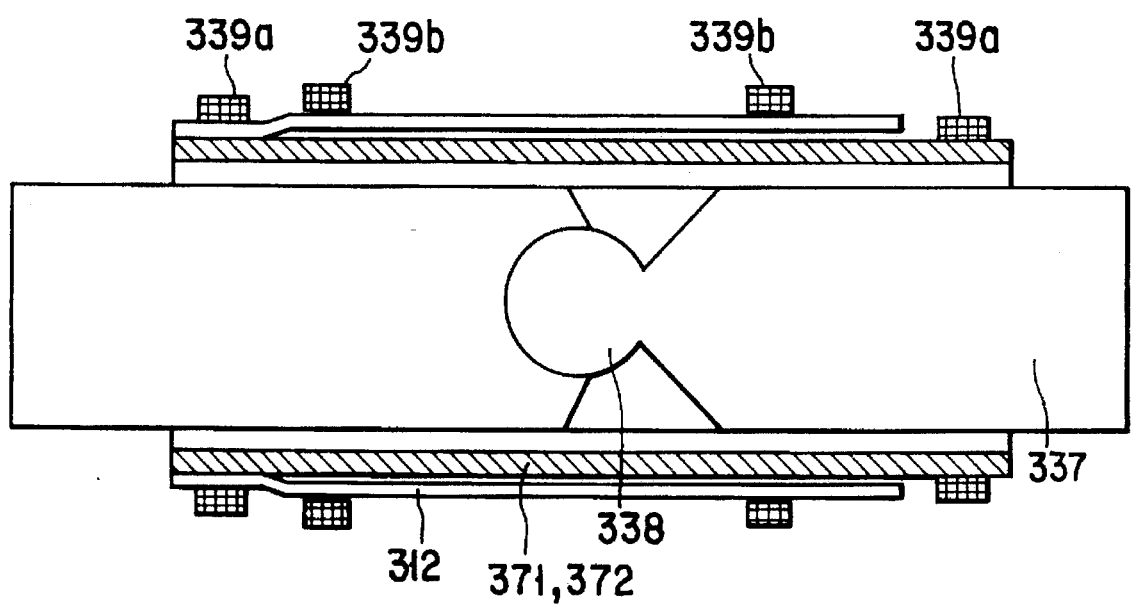

Thereafter, as shown in FIGS. 67 and 68, a shape memory alloy thin film and a polyimide film are sequentially formed by sputtering, and etched by photolithography to form shape memory alloy thin film patterns 371 serving as the prospective driving bodies and polyimide films 372 on them.

Thereafter, the resist patterns 370 are selectively removed by using an organic solvent or the like. Then, as shown in FIG. 68, a portion of each shape memory alloy thin film pattern 371 is fixed to a corresponding electric heater pattern 326 and the corresponding polyimide film 372 only at one end portion thereof.

Subsequently, ECE processing similar to that described above is performed, and a first insulating interlayer 310 is removed. Then, the shape memory alloy is subjected to shape memory treatment of the expansion/contraction direction, thereby completing a driving mechanism a.

Figure 69A:
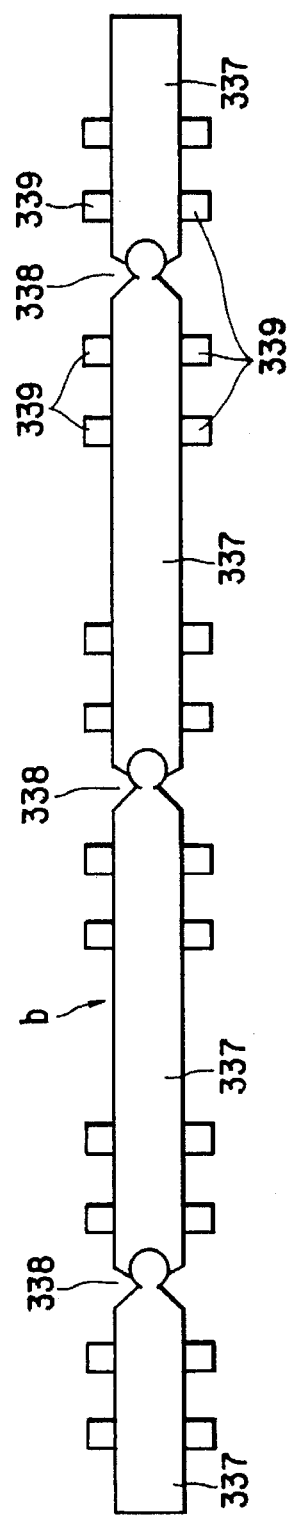
Figure 69B:
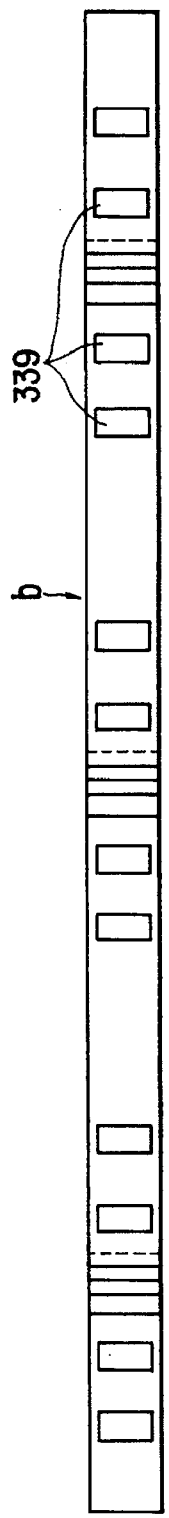

Then, an articulated structure b as shown in FIGS. 69A and 69B is prepared. This is almost the same as that described with reference to FIGS. 47A and 47B, except that a total of eight mount portions 339 are provided on the two sides of each articulated portion 337, with four mount portions 339 on each side.

Figure 70A:
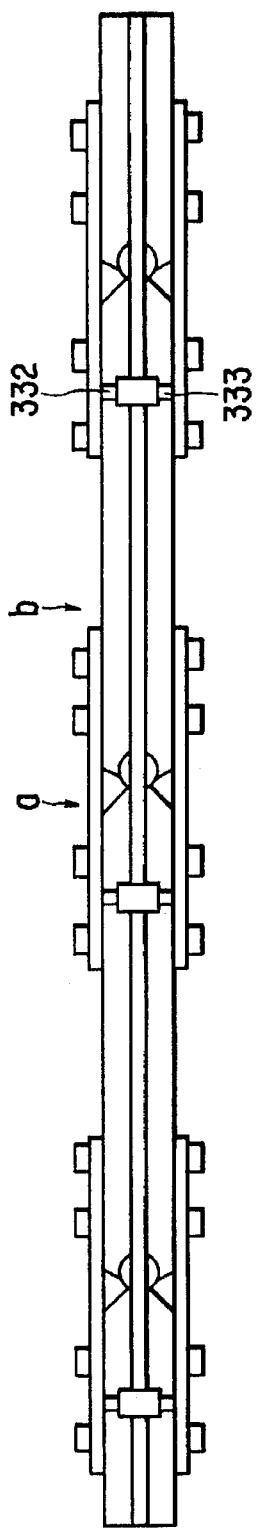
Figure 70B:
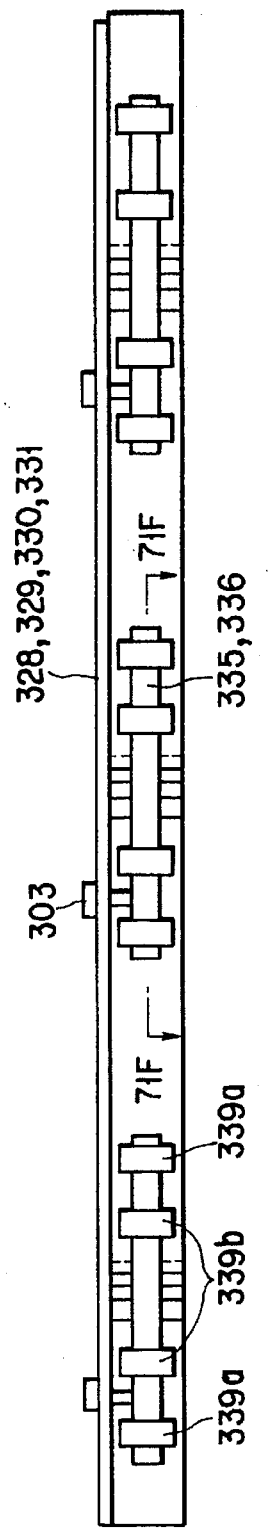

Two driving mechanisms a each prepared in the above manner are mounted on the articulated structure b as shown in FIGS. 70A and 70B. The resultant structure is similar to that shown in FIGS. 49A and 49B. In FIGS. 70A and 70B, each pair of shape memory alloy thin film pattern portions 335 are mounted on four mount portions 339 extending over two articulated portions 337 on the corresponding side surface of the articulated structure b, the shape memory alloy member is fixed by the mount portions 339a on the two ends of the four mount portions 339, and can freely move in the lateral direction at two remaining intermediate mount portions 339b and 339b. The portions of the electric heaters and the second and third insulating layers are fixed only by one of the mount portions 339a on the two ends, which is fixed on the shape memory alloy thin film pattern 335.

With this arrangement, when one electric heater is heated, the shape memory alloy of this portion contracts to flex the articulated portion of the articulated structure b. Since the shape memory alloy portion of the driving body b and the electric heater portion are fixed only at one end thereof, even if the shape memory alloy is largely displaced, the electric heater is not largely strained. Generally, when the same flex angle is to be obtained at an articulated portion of a structure, contraction requires a larger strain than bending flex. Therefore, it is preferable that this countermeasure is taken.

So far, there has been described a method of forming the shape memory alloy thin film pattern 335 at an insulated electric heater portion by sputtering and photolithography in order to integrally form a shape memory alloy member serving as the driving body with the driving mechanisms a. However, a shape memory alloy member subjected to shape memory treatment in advance may be adhered to the insulated electric heater portion. The driving body b is not limited to the shape memory alloy member. If a material which is deformed by a voltage or heat generated by a voltage is used, a driving energy supplying means can be constituted by the electronic circuit groups connected to each other by flexible wirings, electrodes or electric heaters integrally formed with the electric circuit groups, and the like that are disclosed in these embodiments.

In the ninth to eleventh embodiments, an Al thin film formed by sputtering is used as a wiring. However, when the number of articulated portions is increased to increase the entire length of the articulated manipulator, the wiring resistance interferes with a normal operation. Therefore, the wiring width must be increased, which, however, interferes with size reduction in turn. The process of a method of avoiding this problem, after the process of FIGS. 38A and 38B to FIG. 43, will be described with reference to FIGS. 72 to 75.

First, as shown in FIG. 72, wiring patterns similar to those shown in FIG. 44 are formed by Pt thin films 374 having a thickness of about 200 μm by sputtering. As shown in FIG. 73, a 10-μm thick polyimide film 375 and a 1-μm thick Al film are formed. The Al film is etched by using inverted patterns of the wiring patterns of the Pt thin films 374, thereby forming Al film patterns 376. Then, as shown in FIG. 74, using the Al film patterns 376 as masks, the polyimide film 375 is anisotropically etched by RIE to form openings 377 and expose the Pt thin films Then, as shown in FIG. 75, the Al film patterns 376 are selectively removed, and 10-μm thick copper members 378 are selectively formed on the exposed Pt thin films 374 by using a solution mixture of tetraethyl ammonium hydroxide and copper sulfate in accordance with electroless plating. Thereafter, following the same procedures as in FIG. 46 and the subsequent drawings, the articulated manipulator is completed. According to this method, since relatively thick copper members having a small resistivity can be used as the wirings, the wiring resistance can be greatly decreased.

Figures 77A, 77B:
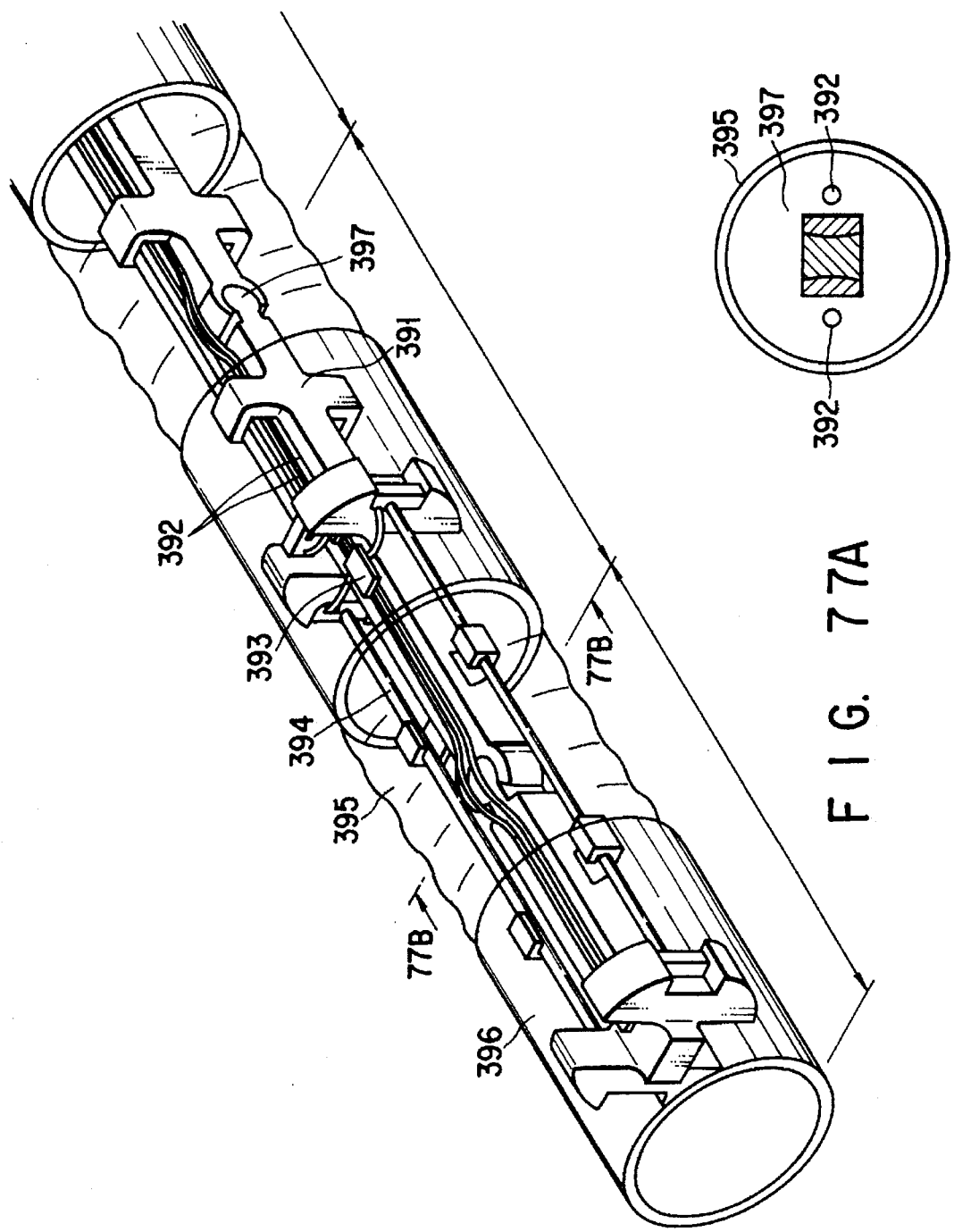
FIG. 77A is a perspective view of an articulated manipulator according to the thirteenth embodiment of the present invention.
FIG. 77B is a sectional view taken along the line 77B—77B of FIG. 77A.

In this manner, when the wiring resistance is greatly decreased and a bipolar transistor having a large driving force is used as the switching transistor of the control circuit, if a very thin shape memory alloy wire is used as the driving body, the shape memory alloy wire, not the electric heater, can be directly powered and heated. FIGS. 76A and 76B, and FIGS. 77A and 77B show the concept of articulated manipulators fabricated in accordance with this method. Actuator control chip arrays constituted by actuator control chips 393 connected with each other by wires 392 are mounted on an articulated structure 391, and first and second driving line terminal regions having the same circuit configuration as that shown in FIG. 41 are directly connected to two ends of each of a pair of very thin shape memory alloy wires 394. In FIG. 76A, the articulated manipulator is mounted on the outer circumferential surface of a pipe-shaped hard portion 396. In FIG. 77A, an articulated manipulator is housed in a pipe constituted by a soft portion 395, corresponding to the flex portion of an articulated portion 397, and a remaining hard portion 396.

FIG. 78 shows the control circuit of an articulated manipulator in which the respective articulated portions of the articulated manipulator are controlled not arbitrarily but sequentially. Referring to FIG. 78, reference symbols R denote resistors. Reference numerals 61-1 to 61-n denote depletion mode MOS-FETs; and 62-1 to 62-n, shape memory alloy (SMA) members. The resistors R divide input voltages and apply voltages corresponding to the divided voltage to the drains of the FETs 61-1 to 61-n. The FETs 61-1 to 61-n serve as switching elements for supplying power to the SMA members 62-1 to 62-n.

In the arrangement shown in FIG. 78, when an input voltage V is increased until a voltage $V_1$ is larger than a gate-source cutoff voltage $V_{GS}$, the FET 61-1 is turned on to supply a constant current to the SMA member 62-1. The input voltage V is divided by resistors R into voltages VGS(OFF), $V_2$, $V_3$, $V_4$, ..., and $V_n$ satisfying VGS(OFF) >$V_2$>$V_3$>$V_4$ ... >Vn and applied to other FETs 61-2 to 61-n to turn them off.

When the input voltage V is further increased, $V_2$>$V_{GS}$ (OFF) is established to turn on the FET 61-2 as well, so that the constant current is also supplied to the SMA member 62-2. When the above operation is repeated, finally $V_1$>$V_2$>$V_3$> ... >$V_n$>$V_{GS}$(OFF) is established, and power is supplied sequentially to the SMA members 62-1 to 62-n by the input voltage V.

In this embodiment, the switching operations of the FETs are used to control power supply to the shape memory alloy (SMA) members. However, the present invention is not limited to this, and a circuit configuration shown in FIG. 79 using Zener diodes as the switching elements can also be adopted to control power supply to the SMA members.

Referring to FIG. 79, reference numerals 61-1 to 65-n denote SMA members; and 63-1 to 63-n, Zener diodes. The Zener voltages of the Zener diodes 63-1 to 663-n are defined as $V_{ZD1}$, $V_{ZD2}$, $V_{ZD3}$, . . . , and $V_{ZDn}$ satisfying $V_{ZD1} < V_{ZD2} < VZD_3 < . . . < V_{ZDn}$. Reference symbol SD denotes a switching diode. The switching diode SD serves to apply a constant voltage to the SMA members 65-1 to 65-n.

In FIG. 79, an input voltage V is increased. When $V > V_{ZD1}$ is established, a Zener current is supplied to the Zener diode 53-1 to supply power to the SMA member 65-1. The input voltage V is further increased, and when $V > V_{ZD2}$ is established, a Zener current is supplied to the Zener diode 63-2 to supply power to the SMA member 65-2 as well.

When this operation is repeated, finally $V > V_{ZDn}$ is established, and all the SMA members 65-1 to 65-n are powered. When the input voltage V is increased, even if the Zener current flowing from a Zener diode having a low Zener voltage is increased, since a constant voltage is maintained by the switching diode SD, all the SMA members 65-1 to 65-n uniformly contract or expand. Therefore, the SMA members 65-1 to 65-n can be sequentially powered by the input voltage V.

In this embodiment, the zener voltages of the Zener didoes 63-1 to 63-n are sequentially defined as $V_{ZD1}$, $V_{ZD2}$ . . . and $V_{ZDn}$ satisfying $V_{ZD1} < V_{ZD2} < . . . < V_{ZDn}$. However, when this order is changed, a predetermined bending operation can be performed.

From the foregoing, when an articulated manipulator is to be sequentially operated, two SMA power supply control lines are sufficient.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A multi-degree-of-freedom manipulator comprising:

an elongated main body having, at least at part thereof, a plurality of flex portions provided therealong;

a plurality of actuators, respectively provided near said flex portions to correspond to said flex portions, for flexing said flex portions;

two common energy transmission paths, extending along said main body, for transmitting an energy to said plurality of actuators;

a plurality of selective energy supply means, respectively provided near said flex portions and respectively coupled with said plurality of actuators electrically in circuit between said two common energy transmission paths, for controlling the energy supplied from said two common energy transmission paths to said plurality of actuators, thereby respectively independently driving said plurality of actuators; and at least one common control signal transmission path independent of said two common energy transmission paths, for transmitting a control signal to said plurality of selective energy supply means, thereby causing said selective energy supply means to control said plurality of actuators.

2. A manipulator according to claim 1, wherein said common control signal transmission path has a pulse pattern signal transmission line for supplying a pulse pattern signal to said plurality of selective energy supply means and a clock signal transmission line for supplying a clock signal synchronized with the pulse pattern signal, and said selective energy supply means are controlled by synchronizing the pulse pattern signal with the clock signal.

3. A manipulator according to claim 1, wherein said elongated main body has a flexible tube, said flexible tube having a distal end portion which is to be flexed with a multi degree of freedom by said flex portions and which has an observation window and an illumination window, and which comprises an inserting portion of an endoscope.

4. A manipulator according to claim 1, wherein said elongated main body has a flexible body, said flexible body having a distal end portion which is to be flexed with a multi degree of freedom by said plurality of flex portions and which has a treatment member, and which comprises a treatment tool.

5. A multi-degree-of-freedom manipulator comprising:

an elongated main body having, at least at part thereof, a plurality of flex portions provided therealong;

a plurality of actuators, respectively provided near said flex portions to correspond to said flex portions, for flexing said flex portions;

two common energy transmission paths, extending along said main body, for transmitting an energy to said plurality of actuators;

a plurality of selective energy supply means, respectively provided near said flex portions and respectively coupled with said plurality of actuators electrically in circuit between said two common energy transmission paths, for controlling the energy supplied from said two common energy transmission paths to said plurality of actuators, thereby respectively independently driving said plurality of actuators; and wherein each of said two common energy transmission paths transmits a control signal for controlling the plurality of selective energy supply means, superposed on the energy, to cause said plurality of selective energy supply means to selectively control said plurality of actuators.

6. A multi-degree-of-freedom manipulator comprising:

an elongated main body having, at least at part thereof, a plurality of articulated portions arranged therealong and connecting portions for flexibly connecting adjacent ones of said articulated portions;

actuators each having two ends attached, respectively, to two of said plurality of articulated portions to span at least one of said connecting portions positioned between said both ends, for flexibly driving at least one of said two articulated portions through the spanned one of said connecting portions;

at least one actuator control chip array having a plurality of drive control electronic circuit chips, attached to respective ones of said plurality of articulated portions and flexible wiring for electrically connecting adjacent said plurality of drive control electronic circuit chips in series, said plurality of drive control electronic circuit chips being electrically coupled to said actuators, respectively; and means for supplying a driving energy to said actuators selected through said electronic circuit chips, wherein said articulated manipulator has at least one degree of freedom with respect to each of said actuator control electronic circuit chips.

7. A manipulator according to claim 6, wherein said means for supplying the driving energy to said actuators and said actuators are electrically coupled and are integrally formed by a semiconductor integrated circuit forming material.

8. A manipulator according to claim 6, wherein each of said actuators includes a shape memory alloy provided between adjacent ones of said articulated portions, a heater for heating the shape memory alloy, and said driving energy supplying means is electrically connected to said heater.

9. A manipulator according to claim 6, wherein each of said articulated portions has a sensor for detecting a drive state thereof, and said actuator control chip array has functions of driving and reading said sensor.

10. A manipulator according to claim 6, wherein said elongated main body has a flexible tube, said flexible tube having a distal end portion which can be flexed with a multi degree of freedom and which has an observation window and an illumination window, and which comprises an inserting portion of an endoscope.

11. A manipulator according to claim 6, wherein said elongated main body has a flexible body, said flexible body having a distal end portion which can be flexed with a multi degree of freedom and which has a treatment member, and which comprises a treatment tool.

12. The multi-degree-of-freedom manipulator according to claim 6, wherein each of said plurality of drive control electronic circuit chips is directly connected to its respective actuator.

* * * * *

UNITED STATES PATENT AND TRADEMARK OFFICE
CERTIFICATE OF CORRECTION

PATENT NO. : 5,624,380
DATED : Apr. 29, 1997
INVENTOR(S) : TAKAYAMA et al

It is certified that error appears in the above-indentified patent and that said Letters Patent is hereby corrected as shown below:

In the Title Page, under Section [30],

Foreign Application Priority Data before Japan 4-272370, change "Mar. 16, 1992" to --Sep. 16, 1992--;

Under Section [56] References Cited,

U.S. PATENT DOCUMENTS, after 5,060,632 10/1991, change "HIBNO et al" to

--HIBINO et al--.

Signed and Sealed this

Ninth Day of December, 1997

Attest:

BRUCE LEHMAN

*Attesting Officer*     *Commissioner of Patents and Trademarks*